United States Patent [19]
Streuli et al.

[11] Patent Number: 5,994,070
[45] Date of Patent: Nov. 30, 1999

[54] TRIO MOLECULES AND USES RELATED THERETO

[75] Inventors: Michel Streuli, Brookline, Mass.; Anne Debant, Padres le Lez, France; Carles Serra-Pagès, Boston, Mass.

[73] Assignee: Dana-Farber Cancer Institute, Boston, Mass.

[21] Appl. No.: 08/826,267

[22] Filed: Mar. 27, 1997

Related U.S. Application Data

[60] Provisional application No. 60/014,214, Mar. 27, 1996.
[51] Int. Cl.$^6$ .............................. C12N 5/00; C12N 15/00; C07H 21/04
[52] U.S. Cl. .......................... 435/6; 435/69.1; 435/320.1; 435/325; 536/23.5; 536/24.31
[58] Field of Search ........................... 435/6, 320.1, 325, 435/69.1; 536/23.5, 24.31; 800/2, DIG. 1; 514/44; 935/9, 66

[56] References Cited

U.S. PATENT DOCUMENTS 5,585,479  12/1996  Hoke et al. .............................. 536/24.5

OTHER PUBLICATIONS

Streuli et al., "Expression of the receptor–linked protein tyrosine phosphatase LAR: proteolytic cleavage and shedding of the CAM–like extracellular region," EMBO, vol. 11, No. 3, 897–907 (1992).
Serra–Pages et al., "The LAR transmembrane protein tyrosine phosphatase and a coiled–coil LAR–integrating protein co–localize at focal adhesions," EMBO, vol. 14, No. 12, 2827–2838 (1995); Copy of Genbank™ Search Using Nucleotide Sequence of trio.
CF Bennett (1996) Science 271:434.
K Theiler (1989) The House Mouse pp. 148–149.
JF Milligan et al. (1993) J Med Chem 36: 1923–1937.
MD Adams et al (1993) Nature 355: 632–634.

*Primary Examiner*—Bruce R. Campell
*Attorney, Agent, or Firm*—Lahive & Cockfield, LLP; Amy E. Mandragouras; Megan E. Williams

[57] ABSTRACT

Nucleic acids encoding TRIO proteins, the TRIO proteins themselves, and active portions thereof as described. In addition, antibodies immunoreactive with TRIO proteins, and preparations of such compositions are provided. Diagnostic and therapeutic assays and reagents for detecting and treating disorders involving, for example, aberrant expression (or loss thereof) of the TRIO protein are described. Assays are provided for identifying agents that modulate the biological function of TRIO proteins.

25 Claims, 27 Drawing Sheets

FIG. 2B
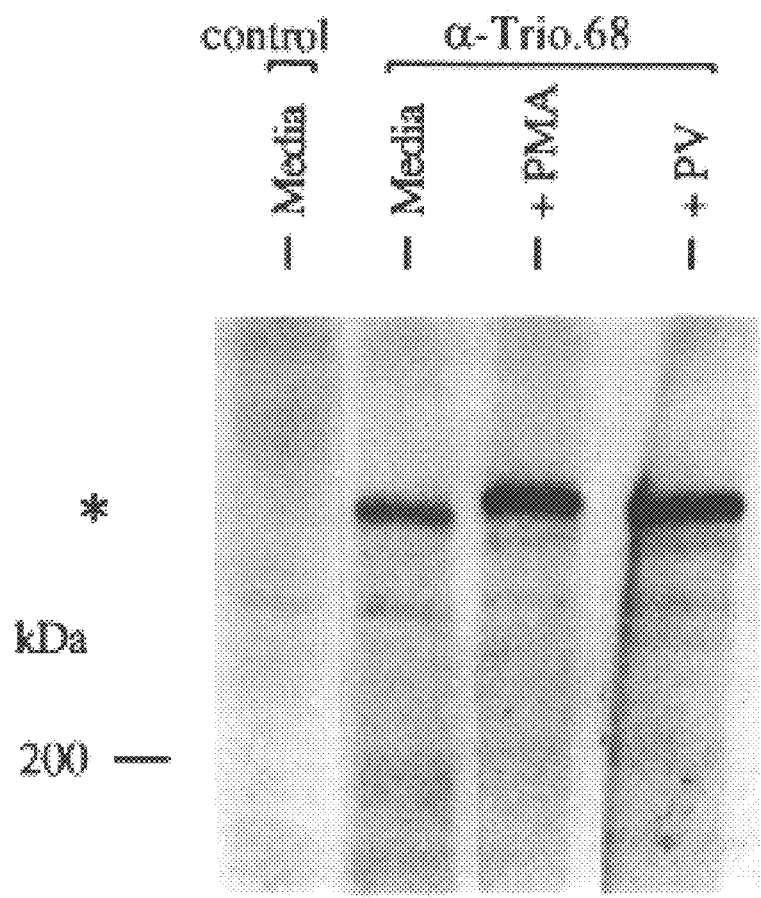
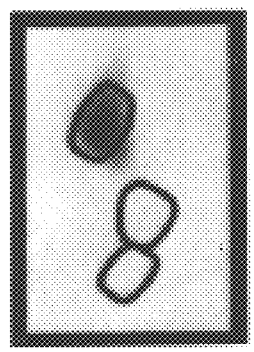

FIG. 4A

```
MKAMDVLPILKEKVAYLSGGRDKRGGPILTFPARSNHDRIRQEDLRRLISYLACIPSEEVCKRGFTVIVDMRGSKWDSIKPLLKILQE     150
SFPCCIHVALIIKPDNFWQKQRTNFGSSKFEFETNMVSLEGLTKVVDPSQLTPEFDGCLEYN
HEEWIEIRVAFEDYISNATHMLSRLEELQDILAKKELPQDLEGARMIEEHSQLKKVVIKAPIEDLDLEGQKLLQRIQSSESFPKKNS     300
GSGNADLQNLLPKVSTMLDRLHSTRQHLHQMWHVRKLKLDQCFQLRLFEQDAEKMFDWITHN
KGLFLNSYTEIGTSHPHAMELQTQHNHFAMNCMNVYVNINRIMSVANRLVESGHYASQQIRQIASQLEQEWKAFAAALDERSTLLDMS     450
SIFHQKAEKYMSNVDSWCKACGEVDLPSELQDLEDAIHHHQGIYEHITLAYSEVSQDGKSLL
DKLQRPLTPGSSDSLTASANYSKAVHHVLDVIHEVLHHQRHVRTIWQHRKVRLHQRLQLCVFQQEVQQVLDWIENHGEAFLSKHTGVG     600
KSLHRARALQKRHEDFEEVAQNTYTNADKLLEAAEQLAQTGECDPEEIYQAAHQLEDRIQDF
VRRVEQRKILLDMSVSFHTHVKELWTWLEELQKELLDDVYAESVEAVQDLIKRFGQQQQTTLQVTVNVIKEGEDLIQQLRDSAISSNK     750
TPHNSSINHIETVLQQLDEAQSQMEELFQERKIKLELFLHVRIFERDAIDIISDLESWNDEL
SQQMNDFDTEDLTIAEQRLQHHADKALTMNNLTFDVIHQGQDLLQYVNEVQASGVELLCDRDVDMATRVQDLLEFLHEKQQELDLAAE     900
QHRKHLEQCVQLRHLQAEVKQVLGWIRNGESMLNAGLITASSLQEAEQLQREHEQFQHAIEK
THQSALQVQQKAEAMLQANHYDMDMIRDCAEKVASHWQQLMLKMEDRLKLVNASVAFYKTSEQVCSVLESLEQEYKREEDWCGGADKL     1050
GPNSETDHVTPMISKHLEQKEAFLKACTLARRNADVFLKYLHRNSVNMPGMVTHIKAPEQQV
KNILNELFQRENRVLHYWTMRKRRLDQCQQYVVFERSAKQALEWIHDNGEFYLSTHTSTGSSIQHTQELLKEHEEFQITAKQTKERVK     1200
LLIQLADGFCEKGHAHAAEIKKCVTAVDKRYRDFSLRMEKYRTSLEKALGISSDSNKSSKSL
QLDIIPASIPGSEVKLRDAAHELNEEKRKSARRKEFIMAELIQTEKAYVRDLRECMDTYLWEMTSGVEEIPPGIVNKELIIFGNMQEI     1350
YEFHNNIFLKELEKYEQLPEDVGHCFVTWADKFQMYVTYCKNKPDSTQLILEHAGSYFDEIQ
QRHGLANSISSYLIKPVQRITKYQLLKELLTCCEEGKGEIKDGLEVMLSVPKRANDAMHLSMLEGFDENIESQGELILQESFQVWDP     1500
KTLIRKGRERHLFLFEMSLVFSKEVKDSSGRSKYLYKSKLFTSELGVTEHVEGDPCKFALWV
GRTPTSDNKIVLKASSIENKQDWIKHIREVIQERTIHLKGALKEPIHIPKTAPATRQKGRRDGEDLDSQGDGSSQPDTISIASRTSQN     1650
TLDSDKLSGGCELTVVIHDFTACNSNELTIRRGQTVEVLERPHDKPDWCLVRTTDRSPAAEG
LVPCGSLCIAHSRSSMEMEGIFNHKDSLSVSSNDASPPASVASLQPHMIGAQSSPGPKRPGNTLRKWLTSPVRRLSSGKADGHVKKLA     1800
HKHKKSREVRKSADAGSQKDSDDSAATPQDETVEERGRNEGLSSGTLSKSSSSGMQSCGEEE
```

FIG. 4B

```
GEEGADAVPLPPPMAIQQHSLLQPDSQDDKASSRLLVRPTSSETPSAAELVSAIEELVKSKMALEDRPSSLLVDQGDSSSPSFNPSDN
SLLSSSPIDEMEERKSSSLKRRHYVLQELVETERDYVRDLGYVVEGYMALMKEDGVPDDMK                        1950
GKDKIVFGNIHQIYDWHRDFFLGELEKCLEDPEKLGSLFVKHERRLHMYIAYCQNKPKSEHIVSEYIDTFFEDLKQRLGHRLQLTDLL
IKPVQRIMKYQLLLKDFLKYSKKASLDTSELERAVEVMCIVPRRCNDMMNVGRLQGFDGKIV                      2100
AQGKLLLQDTFLVTDQDAGLLPRCRERRIFLFEQIVIFSEPLDKKGFSMPGFLFKNSIKVSCLCLEENVENDPCKFALTSRTGDVVE
TFILHSSSPSVRQTWIHEINQILENQRNFLNALTSPIEYQRNHSGGGGGSGAAAGVGAAA                        2250
AAGPPVAAAATVAAPAAAAAPPARAGAGPPGSPSLSDTTPPCWSPLQPRARQRQTRCQSESSSSSNISTMLVTHDYTAVKEDEINVYQ
GEVVQILASNQQNMFLVFRAATDQCPAAEGWIPGFVLGHTSAVIVENPDGTLKKSTSWHTAL                      2400
RLRKKSEKKDKDGKREGKLENGYRKSREGLSNKVSVKLLNPNYIYDVPPEFVIPLSEVTCETGETVVLRCRVCGRPKASITWKGPEHN
TLNNDGHYSISYSDLGEATLKIVGVTTEDDGIYTCIAVNDMGSASSSASLRVLGPGMDGIMV                      2550
TWKDNFDSFYSEVAELGRGRFSVVKKCDQKGTKRAVATKFVNKKLMKRDQVTHELGILQSLQHPLLVGLLDTFETPTSYILVLEMADQ
GRLLDCVVRWGSLTEGKIRAHLGEVLEAVRYLHNCRIAHLDLKPENILVDESLAKPTIKLAD                      2700
FGDAVQLNTTYIHQLLGNPEFAAPEIILGNPVSLTSDTWSVGVLTYVLLSGVSPFLDDSVEETCLNICRLDFSFPDDYFKGVSQKAK
EFVCFLLQEDPAKRPSAALALQEQWLQAGNGRSTGVLDTSRLTSFIERRKHQNDVRPIRSIK                      2851
NFLQSRLLPRV                                                                        2861
```

FIG.4C

```
TRIO GEF-D1  1237    IMAELIQTEKAYVRDLRECMDTYLWEMTSGV  EEIPPGIVNKELIIFGNMQEIYE
TRIO GEF-D2  1914    VLQELVETERDYVRDLGYVVEGYMALMKE    DGVPDDMKGKDKIVFGNIHQIYD
dbl GEF      499     VLNELIQTERVYVRELYTVLLGYRAEMDNPEMFDLMPPLLRNKKDILFGNMAEIYE
ost GEF      446     VMNELLDTERAYVEELLCVLEGYAAEMDNPLMAHLISTGLQNKKNILFGNMEEIYH Consensus            V  EL  TEr  YVr  L   V   gY  aeM                nK       I FGNm  eIY
GEF Cons.            VL  e     te Yv  L   l                                if n         SCR2
                              SCR1

Trio GEF-D1          FHNNIFLKELEKYEQLPEDVGHCFVTWADKFQMYVTYCKNKPDSTQLILEHA
Trio GEF-D2          WHRDFFLGELEKCLEDPEKLGSLFVKHERRLHMYIAYCQNKPKSEHIVSEYI
dbl GEF              FHNDIFLSSLENCAHAPERVGPCFLERKDDFQMYAKYCQNKPRSETIWRKYS
ost GEF              FHNRIFLRELESCIDCPELVGRCFLERMEEFQIYEKYCQNKPRSESLWRQCS Consensus            fHn iFL  LE  c    PE  vG  cF           fqMY    YCqNKP Se
GEF Cons.            h    f   i                  F                   Y
```

FIG.4D

| | | |
|---|---|---|
| Trio GEF-D1 | G SYFDEIQQRHGLANSISSYLIKPVQRITKYQLLLKELLTCCE E GKGEIKDGLEVMLSVPKRAND | 1407 |
| Trio GEF-D2 | D TFFEDLKQRLGHRLQLTDLLIKPVQRIMKYQLLLKDFLKYSKKASLDTSELERAVEVMCIVPRRCND | 2085 |
| dbl GEF | ECAFFQECQRKLKHRLRLDSYLLKPVQRITKYQLLLKELLKYSKDCE GSALLKKALDAMLDLLKSVND | 674 |
| ost GEF | DCPFFQECQKKLDHKLSLDSYLLKPVQRITKYQLLLKEMLKYSKHCE GAEDLQEALSSILGILKAVND | 621 |
| Consensus | fF e q l h l l syL KPVQRItKYQLLLKe Lkysk e g L al l k ND | |
| GEF Cons. | l L Pv r y L L ELl t | |

SCR3

FIG. 4E

```
Trio PSK    2560   YSEVAELGRGRFSVVKKCDQKGTKRAVATKFVNKKLMKRDQVTH        ELGI
DAP PSK       13   YDTGEELGSGQFAVVKKCREKSTGLQYPAKFIKKRRTKSSRRGVSREDIEREVSI
dbMLCK PSK     8   YEFKEELGRGAFSIVYLGENKQTKQRYAIKVINKSELGKDYEKNL       KMEVDI
Consensus          Y     ELG G F V         KT    Y    K        K        E   I
PSK Cons.                            G G       V              K              E Trio PSK           LQSLQHPLLVGLLDTFETPTSYILVLEMADQGRLLDCVVRWGSLTE       GKIRA
DAP PSK            LKEIQHPNVITLHEVYENKTDVILILELVAGGELFDFLAEKESLTEEEATEFLKQILNGV
dbMLCK PSK         LKKVNHPNIIALKELFDTPEKLYLVMELVTGGELFDKIVEKGSYSEADAANLVKKIVSAV
Consensus          L    HP                   L    E    G L D           S    E
PSK Cons.
```

FIG. 4F

```
TRIO PSK      HLGEVCRIAHLDLKPENIL VDESLAKPTIKLADFGDAVQLNTTYIHQLLGNPEFAAPEI
DAP PSK       YYLHSLQIAHFDLKPENIMLLDRNVPKPRIKIIDFGNEFKNIF        GTPEFVAPEI
dbMLCK PSK    GYLHGLNIVHRDLKPENLL LKSKENHLEVAIADFGLSKIIGQTLVMQTACGTPSYVAPEV
Consensus                H DLKPEN                     DFG       G P    APE
PSK Cons.                  D K N                      D G                PE TRIO PSK      ILGNPVSLTSDTWSVGVLTYVLLSGVSPFLDDSVEETCLNICRLDFSFPDDYFKGVSQKAKEFVCFLL
DAP PSK       VNYEPLGLEADMWSIGVITYILLSGASPFLGDTKQETLANVSAVNYEFEDEYFSNTSALAKDFIRRLL
dbMLCK PSK    LNATGYDKEVDMWSIGVITYILLCGFPPFYGDTVPEIFEQIMEVNYEFPEEYWGGISKEAKDFIGKLL
Consensus       D WS GV TY LL G PF D       E                  F  Y    S   K F   LL
PSK Cons.         D    G TRIO PSK      QEDPAKRPSAALALQEQWLQA   2816
DAP PSK       VKDPKKRMTIQDSLQHPWIKP    269
dbMLCK PSK    VVDVSKRLNATNALNHPWLKS    267
Consensus       D  KR        L  WL
PSK Cons.         R
```

Control   HA

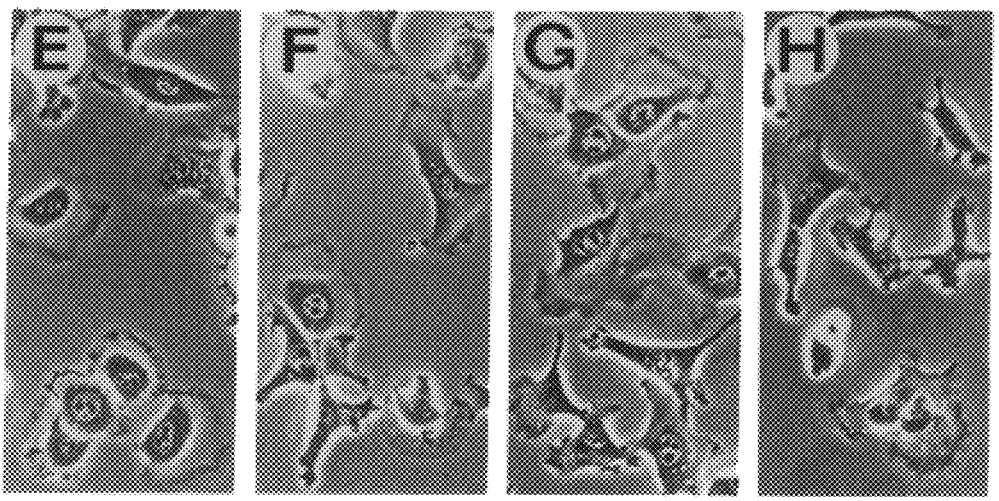

Trio Δ3

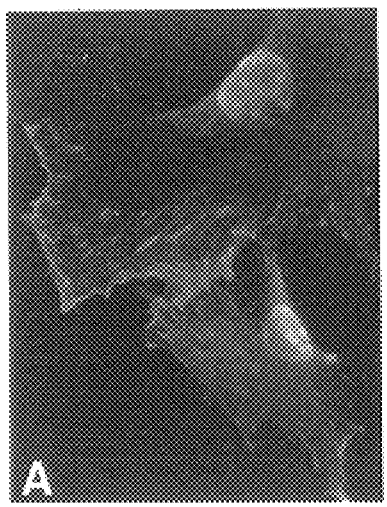
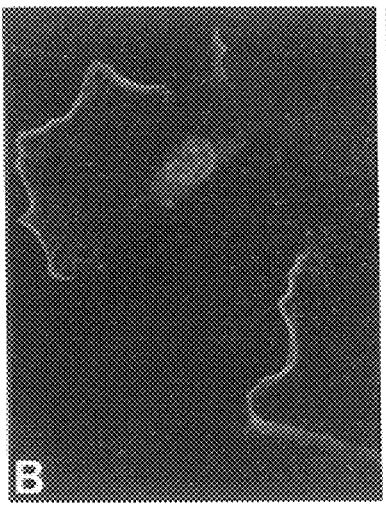
FIG. 8A  Ha
FIG. 8B  Trio Δ2
FIG. 8C  Trio Δ3

HA    FIG.9A 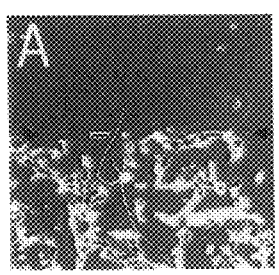    FIG.9B 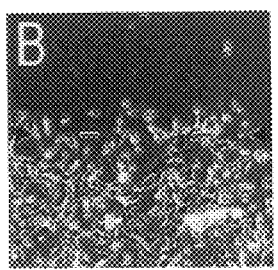    FIG.9C 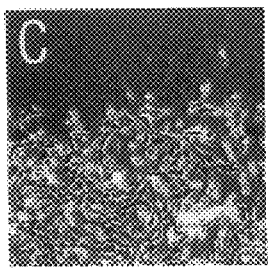    FIG.9D 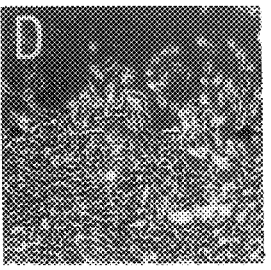

Trio Δ2

Trio Δ3

HA

Trio Δ2

Trio Δ3

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 8906 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 67..8647

(xi) SEQUENCE DESCRIPTION: SEQ ID NO:1:

```
GAGGCGGCCA AGGACCTGGC CGACATCGCG GCCTTCTTCC GATCCGGGTT TCGAAAAAAC          60

GATGAA ATG AAA GCT ATG GAT GTT TTA CCA ATT TTG AAG GAA AAA GTT           108
       Met Lys Ala Met Asp Val Leu Pro Ile Leu Lys Glu Lys Val
         1               5                  10

GCA TAC CTT TCA GGT GGG AGA GAT AAA CGT GGA GGT CCC ATT TTA ACG          156
Ala Tyr Leu Ser Gly Gly Arg Asp Lys Arg Gly Gly Pro Ile Leu Thr
 15                  20                  25                  30

TTT CCG GCC CGC AGC AAT CAT GAC AGA ATA CGA CAG GAG GAT CTC AGG          204
Phe Pro Ala Arg Ser Asn His Asp Arg Ile Arg Gln Glu Asp Leu Arg
                 35                  40                  45

AGA CTC ATT TCC TAT CTA GCC TGT ATT CCC AGC GAG GAG GTC TGC AAG          252
Arg Leu Ile Ser Tyr Leu Ala Cys Ile Pro Ser Glu Glu Val Cys Lys
             50                  55                  60

CGT GGC TTC ACG GTG ATC GTG GAC ATG CGT GGG TCC AAG TGG GAC TCC          300
Arg Gly Phe Thr Val Ile Val Asp Met Arg Gly Ser Lys Trp Asp Ser
         65                  70                  75

ATC AAG CCC CTT CTG AAG ATC CTG CAG GAG TCC TTC CCC TGC TGC ATC          348
Ile Lys Pro Leu Leu Lys Ile Leu Gln Glu Ser Phe Pro Cys Cys Ile
     80                  85                  90

CAT GTG GCC CTG ATC ATC AAG CCA GAC AAC TTC TGG CAG AAA CAG AGG          396
His Val Ala Leu Ile Ile Lys Pro Asp Asn Phe Trp Gln Lys Gln Arg
 95                 100                 105                 110

ACT AAT TTT GGC AGT TCT AAA TTT GAA TTT GAG ACA AAT ATG GTC TCT          444
Thr Asn Phe Gly Ser Ser Lys Phe Glu Phe Glu Thr Asn Met Val Ser
                115                 120                 125

TTA GAA GGC CTT ACC AAA GTA GTT GAT CCT TCT CAG CTA ACT CCT GAG          492
Leu Glu Gly Leu Thr Lys Val Val Asp Pro Ser Gln Leu Thr Pro Glu
            130                 135                 140

TTT GAT GGC TGC CTG GAA TAC AAC CAC GAA GAA TGG ATT GAA ATC AGA          540
Phe Asp Gly Cys Leu Glu Tyr Asn His Glu Glu Trp Ile Glu Ile Arg
        145                 150                 155

GTT GCT TTT GAA GAC TAC ATT AGC AAT GCC ACC CAC ATG CTG TCT CGG          588
Val Ala Phe Glu Asp Tyr Ile Ser Asn Ala Thr His Met Leu Ser Arg
    160                 165                 170

CTG GAG GAA CTT CAG GAC ATC CTA GCT AAG AAG GAG CTG CCT CAG GAT          636
Leu Glu Glu Leu Gln Asp Ile Leu Ala Lys Lys Glu Leu Pro Gln Asp
175                 180                 185                 190

TTA GAG GGG GCT CGG AAT ATG ATC GAG GAA CAT TCT CAG CTG AAG AAG          684
Leu Glu Gly Ala Arg Asn Met Ile Glu Glu His Ser Gln Leu Lys Lys
                195                 200                 205

AAG GTG ATT AAG GCC CCC ATC GAG GAC CTG GAT TTG GAG GGA CAG AAG          732
Lys Val Ile Lys Ala Pro Ile Glu Asp Leu Asp Leu Glu Gly Gln Lys
```

-continued

|  | 210 | | | | 215 | | | | 220 | | | |  |
|---|---|---|---|---|---|---|---|---|---|---|---|---|---|
| CTG | CTT | CAG | AGG | ATA | CAG | AGC | AGT | GAA | AGC | TTT | CCC | AAA | AAG | AAC | TCA | 780 |
| Leu | Leu | Gln | Arg | Ile | Gln | Ser | Ser | Glu | Ser | Phe | Pro | Lys | Lys | Asn | Ser | |
| | | 225 | | | | | 230 | | | | | 235 | | | | |

| GGC | TCA | GGC | AAT | GCG | GAC | CTG | CAG | AAC | CTC | TTG | CCC | AAG | GTG | TCC | ACC | 828 |
| Gly | Ser | Gly | Asn | Ala | Asp | Leu | Gln | Asn | Leu | Leu | Pro | Lys | Val | Ser | Thr | |
| | 240 | | | | | 245 | | | | | 250 | | | | | |

| ATG | CTG | GAC | CGG | CTG | CAC | TCG | ACA | CGG | CAG | CAT | CTG | CAC | CAG | ATG | TGG | 876 |
| Met | Leu | Asp | Arg | Leu | His | Ser | Thr | Arg | Gln | His | Leu | His | Gln | Met | Trp | |
| 255 | | | | | 260 | | | | | 265 | | | | | 270 | |

| CAT | GTG | AGG | AAG | CTG | AAG | CTG | GAC | CAG | TGC | TTC | CAG | CTG | AGG | CTG | TTT | 924 |
| His | Val | Arg | Lys | Leu | Lys | Leu | Asp | Gln | Cys | Phe | Gln | Leu | Arg | Leu | Phe | |
| | | | 275 | | | | | 280 | | | | | 285 | | | |

| GAA | CAG | GAT | GCT | GAG | AAG | ATG | TTT | GAC | TGG | ATC | ACA | CAC | AAC | AAA | GGC | 972 |
| Glu | Gln | Asp | Ala | Glu | Lys | Met | Phe | Asp | Trp | Ile | Thr | His | Asn | Lys | Gly | |
| | | 290 | | | | | 295 | | | | | 300 | | | | |

| CTG | TTT | CTA | AAC | AGC | TAC | ACA | GAG | ATT | GGG | ACC | AGC | CAC | CCT | CAT | GCC | 1020 |
| Leu | Phe | Leu | Asn | Ser | Tyr | Thr | Glu | Ile | Gly | Thr | Ser | His | Pro | His | Ala | |
| | | 305 | | | | | 310 | | | | | 315 | | | | |

| ATG | GAG | CTT | CAG | ACG | CAG | CAC | AAT | CAC | TTT | GCC | ATG | AAC | TGT | ATG | AAC | 1068 |
| Met | Glu | Leu | Gln | Thr | Gln | His | Asn | His | Phe | Ala | Met | Asn | Cys | Met | Asn | |
| | 320 | | | | | 325 | | | | | 330 | | | | | |

| GTG | TAT | GTA | AAT | ATA | AAC | CGC | ATC | ATG | TCG | GTG | GCC | AAT | CGT | CTG | GTG | 1116 |
| Val | Tyr | Val | Asn | Ile | Asn | Arg | Ile | Met | Ser | Val | Ala | Asn | Arg | Leu | Val | |
| 335 | | | | | 340 | | | | | 345 | | | | | 350 | |

| GAG | TCT | GGC | CAC | TAT | GCC | TCG | CAG | CAG | ATC | AGG | CAG | ATC | GCG | AGT | CAG | 1164 |
| Glu | Ser | Gly | His | Tyr | Ala | Ser | Gln | Gln | Ile | Arg | Gln | Ile | Ala | Ser | Gln | |
| | | | 355 | | | | | 360 | | | | | 365 | | | |

| CTG | GAG | CAG | GAG | TGG | AAG | GCG | TTT | GCG | GCA | GCC | CTG | GAT | GAG | CGG | AGC | 1212 |
| Leu | Glu | Gln | Glu | Trp | Lys | Ala | Phe | Ala | Ala | Ala | Leu | Asp | Glu | Arg | Ser | |
| | | 370 | | | | | 375 | | | | | 380 | | | | |

| ACC | TTG | CTG | GAC | ATG | TCC | TCC | ATT | TTC | CAC | CAG | AAG | GCC | GAA | AAG | TAT | 1260 |
| Thr | Leu | Leu | Asp | Met | Ser | Ser | Ile | Phe | His | Gln | Lys | Ala | Glu | Lys | Tyr | |
| | | 385 | | | | | 390 | | | | | 395 | | | | |

| ATG | AGC | AAC | GTG | GAT | TCA | TGG | TGT | AAA | GCT | TGC | GGT | GAG | GTA | GAC | CTT | 1308 |
| Met | Ser | Asn | Val | Asp | Ser | Trp | Cys | Lys | Ala | Cys | Gly | Glu | Val | Asp | Leu | |
| | 400 | | | | | 405 | | | | | 410 | | | | | |

| CCC | TCA | GAG | CTG | CAG | GAC | CTA | GAA | GAT | GCC | ATT | CAT | CAC | CAC | CAG | GGA | 1356 |
| Pro | Ser | Glu | Leu | Gln | Asp | Leu | Glu | Asp | Ala | Ile | His | His | His | Gln | Gly | |
| 415 | | | | | 420 | | | | | 425 | | | | | 430 | |

| ATA | TAT | GAA | CAT | ATC | ACT | CTT | GCT | TAT | TCT | GAG | GTC | AGC | CAA | GAT | GGG | 1404 |
| Ile | Tyr | Glu | His | Ile | Thr | Leu | Ala | Tyr | Ser | Glu | Val | Ser | Gln | Asp | Gly | |
| | | | 435 | | | | | 440 | | | | | 445 | | | |

| AAG | TCG | CTC | CTT | GAC | AAG | CTC | CAG | CGG | CCC | TTG | ACT | CCC | GGC | AGC | TCC | 1452 |
| Lys | Ser | Leu | Leu | Asp | Lys | Leu | Gln | Arg | Pro | Leu | Thr | Pro | Gly | Ser | Ser | |
| | | 450 | | | | | 455 | | | | | 460 | | | | |

| GAT | TCC | CTG | ACA | GCC | TCT | GCC | AAC | TAC | TCC | AAG | GCC | GTG | CAC | CAT | GTC | 1500 |
| Asp | Ser | Leu | Thr | Ala | Ser | Ala | Asn | Tyr | Ser | Lys | Ala | Val | His | His | Val | |
| | | 465 | | | | | 470 | | | | | 475 | | | | |

| CTG | GAT | GTC | ATC | CAC | GAG | GTG | CTG | CAC | CAC | CAG | CGG | CAC | GTG | AGA | ACA | 1548 |
| Leu | Asp | Val | Ile | His | Glu | Val | Leu | His | His | Gln | Arg | His | Val | Arg | Thr | |
| | 480 | | | | | 485 | | | | | 490 | | | | | |

| ATC | TGG | CAA | CAC | CGC | AAG | GTC | CGG | CTG | CAT | CAG | AGG | CTG | CAG | CTG | TGT | 1596 |
| Ile | Trp | Gln | His | Arg | Lys | Val | Arg | Leu | His | Gln | Arg | Leu | Gln | Leu | Cys | |
| 495 | | | | | 500 | | | | | 505 | | | | | 510 | |

| GTT | TTC | CAG | CAG | GAA | GTT | CAG | CAG | GTG | CTA | GAC | TGG | ATC | GAG | AAC | CAC | 1644 |
| Val | Phe | Gln | Gln | Glu | Val | Gln | Gln | Val | Leu | Asp | Trp | Ile | Glu | Asn | His | |
| | | | 515 | | | | | 520 | | | | | 525 | | | |

| GGA | GAA | GCA | TTT | CTG | AGC | AAA | CAT | ACA | GGT | GTG | GGG | AAA | TCT | CTT | CAT | 1692 |
| Gly | Glu | Ala | Phe | Leu | Ser | Lys | His | Thr | Gly | Val | Gly | Lys | Ser | Leu | His | |

-continued

```
             530                 535                 540
CGG GCC AGA GCA TTG CAG AAA CGT CAT GAA GAT TTT GAA GAA GTG GCA        1740
Arg Ala Arg Ala Leu Gln Lys Arg His Glu Asp Phe Glu Glu Val Ala
        545                 550                 555

CAG AAC ACA TAC ACC AAT GCG GAT AAA TTA CTG GAA GCA GCA GAA CAG        1788
Gln Asn Thr Tyr Thr Asn Ala Asp Lys Leu Leu Glu Ala Ala Glu Gln
    560                 565                 570

CTG GCT CAG ACT GGG GAA TGT GAC CCC GAA GAG ATT TAT CAG GCT GCC        1836
Leu Ala Gln Thr Gly Glu Cys Asp Pro Glu Glu Ile Tyr Gln Ala Ala
575                 580                 585                 590

CAT CAG CTG GAA GAC CGG ATT CAA GAT TTC GTT CGG CGT GTT GAG CAG        1884
His Gln Leu Glu Asp Arg Ile Gln Asp Phe Val Arg Arg Val Glu Gln
            595                 600                 605

CGA AAG ATC CTA CTG GAC ATG TCA GTG TCC TTT CAC ACC CAT GTG AAA        1932
Arg Lys Ile Leu Leu Asp Met Ser Val Ser Phe His Thr His Val Lys
        610                 615                 620

GAG CTG TGG ACG TGG CTG GAG GAG CTG CAG AAG GAG CTG CTG GAC GAC        1980
Glu Leu Trp Thr Trp Leu Glu Glu Leu Gln Lys Glu Leu Leu Asp Asp
    625                 630                 635

GTG TAT GCC GAG TCG GTG GAG GCC GTG CAG GAC CTC ATC AAG CGC TTT        2028
Val Tyr Ala Glu Ser Val Glu Ala Val Gln Asp Leu Ile Lys Arg Phe
640                 645                 650

GGC CAG CAG CAG CAG ACC ACC CTG CAG GTG ACT GTC AAC GTG ATC AAG        2076
Gly Gln Gln Gln Gln Thr Thr Leu Gln Val Thr Val Asn Val Ile Lys
655                 660                 665                 670

GAA GGG GAG GAC CTC ATC CAG CAG CTC AGG GAC TCT GCC ATC TCC AGT        2124
Glu Gly Glu Asp Leu Ile Gln Gln Leu Arg Asp Ser Ala Ile Ser Ser
                675                 680                 685

AAC AAG ACC CCC CAC AAC AGC TCC ATC AAC CAC ATT GAG ACG GTG CTG        2172
Asn Lys Thr Pro His Asn Ser Ser Ile Asn His Ile Glu Thr Val Leu
            690                 695                 700

CAG CAG CTG GAC GAG GCG CAG TCG CAG ATG GAG GAG CTC TTC CAG GAG        2220
Gln Gln Leu Asp Glu Ala Gln Ser Gln Met Glu Glu Leu Phe Gln Glu
        705                 710                 715

CGC AAG ATC AAG CTG GAG CTC TTC CTG CAC GTG CGC ATC TTC GAG AGG        2268
Arg Lys Ile Lys Leu Glu Leu Phe Leu His Val Arg Ile Phe Glu Arg
    720                 725                 730

GAC GCC ATC GAC ATT ATC TCA GAC CTC GAG TCT TGG AAT GAT GAG CTT        2316
Asp Ala Ile Asp Ile Ile Ser Asp Leu Glu Ser Trp Asn Asp Glu Leu
735                 740                 745                 750

TCT CAG CAA ATG AAT GAC TTC GAC ACA GAA GAT CTC ACG ATT GCA GAG        2364
Ser Gln Gln Met Asn Asp Phe Asp Thr Glu Asp Leu Thr Ile Ala Glu
                755                 760                 765

CAG CGC CTC CAG CAC CAT GCA GAC AAA GCC TTG ACC ATG AAC AAC TTG        2412
Gln Arg Leu Gln His His Ala Asp Lys Ala Leu Thr Met Asn Asn Leu
            770                 775                 780

ACT TTT GAC GTC ATC CAC CAA GGG CAA GAT CTT CTG CAG TAT GTC AAT        2460
Thr Phe Asp Val Ile His Gln Gly Gln Asp Leu Leu Gln Tyr Val Asn
        785                 790                 795

GAG GTC CAG GCC TCT GGT GTG GAG CTG CTG TGT GAT AGA GAT GTA GAC        2508
Glu Val Gln Ala Ser Gly Val Glu Leu Leu Cys Asp Arg Asp Val Asp
    800                 805                 810

ATG GCA ACT CGG GTC CAG GAC CTG CTG GAG TTT CTT CAT GAA AAA CAG        2556
Met Ala Thr Arg Val Gln Asp Leu Leu Glu Phe Leu His Glu Lys Gln
815                 820                 825                 830

CAG GAA TTG GAT TTA GCC GCA GAG CAG CAT CGG AAA CAC CTG GAG CAG        2604
Gln Glu Leu Asp Leu Ala Ala Glu Gln His Arg Lys His Leu Glu Gln
                835                 840                 845

TGC GTG CAG CTG CGC CAC CTG CAG GCA GAA GTG AAA CAG GTG CTG GGT        2652
Cys Val Gln Leu Arg His Leu Gln Ala Glu Val Lys Gln Val Leu Gly
```

-continued

```
                    850                 855                 860
TGG ATC CGC AAC GGA GAG TCC ATG TTA AAT GCC GGA CTT ATC ACA GCC      2700
Trp Ile Arg Asn Gly Glu Ser Met Leu Asn Ala Gly Leu Ile Thr Ala
            865                 870                 875

AGC TCG TTA CAA GAG GCA GAG CAG CTC CAG CGA GAG CAC GAG CAG TTC      2748
Ser Ser Leu Gln Glu Ala Glu Gln Leu Gln Arg Glu His Glu Gln Phe
        880                 885                 890

CAG CAT GCC ATT GAG AAA ACA CAT CAG AGC GCG CTG CAG GTG CAG CAG      2796
Gln His Ala Ile Glu Lys Thr His Gln Ser Ala Leu Gln Val Gln Gln
895                 900                 905                 910

AAG GCA GAA GCC ATG CTA CAG GCC AAC CAC TAC GAC ATG GAC ATG ATC      2844
Lys Ala Glu Ala Met Leu Gln Ala Asn His Tyr Asp Met Asp Met Ile
                915                 920                 925

CGG GAC TGC GCC GAG AAG GTG GCG TCT CAC TGG CAA CAG CTC ATG CTC      2892
Arg Asp Cys Ala Glu Lys Val Ala Ser His Trp Gln Gln Leu Met Leu
            930                 935                 940

AAG ATG GAA GAT CGC CTC AAG CTC GTC AAC GCC TCT GTC GCT TTC TAC      2940
Lys Met Glu Asp Arg Leu Lys Leu Val Asn Ala Ser Val Ala Phe Tyr
        945                 950                 955

AAA ACC TCA GAG CAG GTC TGC AGC GTC CTC GAG AGC CTG GAA CAG GAG      2988
Lys Thr Ser Glu Gln Val Cys Ser Val Leu Glu Ser Leu Glu Gln Glu
960                 965                 970

TAC AAG AGA GAA GAA GAC TGG TGT GGC GGG GCG GAT AAG CTG GGC CCA      3036
Tyr Lys Arg Glu Glu Asp Trp Cys Gly Gly Ala Asp Lys Leu Gly Pro
975                 980                 985                 990

AAC TCT GAG ACG GAC CAC GTG ACG CCC ATG ATC AGC AAG CAC CTG GAG      3084
Asn Ser Glu Thr Asp His Val Thr Pro Met Ile Ser Lys His Leu Glu
                995                 1000                1005

CAG AAG GAG GCA TTC CTG AAG GCT TGC ACC CTT GCT CGG AGG AAT GCA      3132
Gln Lys Glu Ala Phe Leu Lys Ala Cys Thr Leu Ala Arg Arg Asn Ala
            1010                1015                1020

GAC GTC TTC CTG AAA TAC CTG CAC AGG AAC AGC GTG AAC ATG CCA GGA      3180
Asp Val Phe Leu Lys Tyr Leu His Arg Asn Ser Val Asn Met Pro Gly
        1025                1030                1035

ATG GTG ACG CAC ATC AAA GCT CCT GAA CAG CAA GTG AAA AAT ATC TTG      3228
Met Val Thr His Ile Lys Ala Pro Glu Gln Gln Val Lys Asn Ile Leu
    1040                1045                1050

AAT GAA CTC TTC CAA CGG GAG AAC AGG GTA TTG CAT TAC TGG ACC ATG      3276
Asn Glu Leu Phe Gln Arg Glu Asn Arg Val Leu His Tyr Trp Thr Met
1055                1060                1065                1070

AGG AAG AGA CGG CTG GAC CAG TGT CAG CAG TAC GTG GTC TTT GAG AGG      3324
Arg Lys Arg Arg Leu Asp Gln Cys Gln Gln Tyr Val Val Phe Glu Arg
                1075                1080                1085

AGT GCC AAG CAG GCT TTG GAA TGG ATC CAT GAC AAT GGC GAG TTC TAC      3372
Ser Ala Lys Gln Ala Leu Glu Trp Ile His Asp Asn Gly Glu Phe Tyr
            1090                1095                1100

CTT TCC ACA CAC ACC TCC ACG GGC TCC AGT ATA CAG CAC ACC CAG GAG      3420
Leu Ser Thr His Thr Ser Thr Gly Ser Ser Ile Gln His Thr Gln Glu
        1105                1110                1115

CTC CTG AAA GAG CAC GAG GAG TTC CAG ATA ACT GCA AAG CAA ACC AAA      3468
Leu Leu Lys Glu His Glu Glu Phe Gln Ile Thr Ala Lys Gln Thr Lys
    1120                1125                1130

GAG AGA GTG AAG CTA TTG ATA CAG CTG GCT GAT GGC TTT TGT GAA AAA      3516
Glu Arg Val Lys Leu Leu Ile Gln Leu Ala Asp Gly Phe Cys Glu Lys
1135                1140                1145                1150

GGG CAT GCC CAT GCG GCA GAG ATA AAA AAA TGT GTT ACT GCT GTG GAT      3564
Gly His Ala His Ala Ala Glu Ile Lys Lys Cys Val Thr Ala Val Asp
                1155                1160                1165

AAG AGG TAC AGA GAT TTC TCT CTG CGG ATG GAG AAG TAC AGG ACC TCT      3612
Lys Arg Tyr Arg Asp Phe Ser Leu Arg Met Glu Lys Tyr Arg Thr Ser
```

-continued

|  |  |  |
|---|---|---|
| 1170 | 1175 | 1180 |

TTG GAA AAA GCC CTG GGG ATT TCT TCA GAT TCC AAC AAA TCG AGT AAA          3660
Leu Glu Lys Ala Leu Gly Ile Ser Ser Asp Ser Asn Lys Ser Ser Lys
         1185            1190            1195

AGT CTC CAG CTA GAT ATC ATT CCA GCC AGT ATC CCT GGC TCA GAG GTG          3708
Ser Leu Gln Leu Asp Ile Ile Pro Ala Ser Ile Pro Gly Ser Glu Val
1200            1205            1210

AAA CTT CGA GAT GCT GCT CAT GAA CTT AAT GAA GAG AAG CGG AAA TCT          3756
Lys Leu Arg Asp Ala Ala His Glu Leu Asn Glu Glu Lys Arg Lys Ser
1215            1220            1225            1230

GCC CGC AGG AAA GAG TTC ATA ATG GCT GAG CTC ATT CAA ACT GAA AAG          3804
Ala Arg Arg Lys Glu Phe Ile Met Ala Glu Leu Ile Gln Thr Glu Lys
         1235            1240            1245

GCT TAT GTA AGA GAC CTC CGG GAA TGT ATG GAT ACG TAC CTG TGG GAA          3852
Ala Tyr Val Arg Asp Leu Arg Glu Cys Met Asp Thr Tyr Leu Trp Glu
1250            1255            1260

ATG ACC AGT GGC GTG GAA GAG ATT CCA CCT GGC ATT GTA AAC AAA GAA          3900
Met Thr Ser Gly Val Glu Glu Ile Pro Pro Gly Ile Val Asn Lys Glu
         1265            1270            1275

CTC ATC ATC TTC GGA AAC ATG CAA GAA ATC TAC GAA TTT CAT AAT AAC          3948
Leu Ile Ile Phe Gly Asn Met Gln Glu Ile Tyr Glu Phe His Asn Asn
         1280            1285            1290

ATA TTC CTA AAG GAG CTG GAA AAA TAT GAA CAG TTG CCA GAG GAT GTT          3996
Ile Phe Leu Lys Glu Leu Glu Lys Tyr Glu Gln Leu Pro Glu Asp Val
1295            1300            1305            1310

GGA CAT TGT TTT GTT ACT TGG GCA GAC AAG TTT CAG ATG TAT GTC ACA          4044
Gly His Cys Phe Val Thr Trp Ala Asp Lys Phe Gln Met Tyr Val Thr
         1315            1320            1325

TAT TGC AAA AAT AAG CCT GAT TCT ACT CAG CTG ATA TTG GAA CAT GCA          4092
Tyr Cys Lys Asn Lys Pro Asp Ser Thr Gln Leu Ile Leu Glu His Ala
         1330            1335            1340

GGG TCC TAT TTT GAC GAG ATA CAG CAG CGA CAT GGA TTA GCC AAT TCC          4140
Gly Ser Tyr Phe Asp Glu Ile Gln Gln Arg His Gly Leu Ala Asn Ser
         1345            1350            1355

ATT TCT TCC TAC CTT ATT AAA CCA GTT CAG CGA ATA ACG AAA TAT CAG          4188
Ile Ser Ser Tyr Leu Ile Lys Pro Val Gln Arg Ile Thr Lys Tyr Gln
         1360            1365            1370

CTC CTT TTA AAA GAG CTG CTG ACG TGC TGT GAG GAA GGA AAG GGA GAG          4236
Leu Leu Leu Lys Glu Leu Leu Thr Cys Cys Glu Glu Gly Lys Gly Glu
1375            1380            1385            1390

ATT AAA GAT GGC CTG GAG GTG ATG CTC AGC GTG CCG AAG CGA GCC AAT          4284
Ile Lys Asp Gly Leu Glu Val Met Leu Ser Val Pro Lys Arg Ala Asn
         1395            1400            1405

GAC GCC ATG CAC CTC AGC ATG CTG GAA GGG TTT GAT GAA AAC ATT GAG          4332
Asp Ala Met His Leu Ser Met Leu Glu Gly Phe Asp Glu Asn Ile Glu
         1410            1415            1420

TCT CAG GGA GAA CTC ATC CTA CAG GAA TCC TTC CAA GTG TGG GAC CCA          4380
Ser Gln Gly Glu Leu Ile Leu Gln Glu Ser Phe Gln Val Trp Asp Pro
         1425            1430            1435

AAA ACC TTA ATT CGA AAG GGT CGA GAA CGG CAT CTC TTC CTT TTT GAA          4428
Lys Thr Leu Ile Arg Lys Gly Arg Glu Arg His Leu Phe Leu Phe Glu
         1440            1445            1450

ATG TCC TTA GTA TTT AGT AAA GAA GTG AAA GAT TCC AGT GGG AGA AGC          4476
Met Ser Leu Val Phe Ser Lys Glu Val Lys Asp Ser Ser Gly Arg Ser
1455            1460            1465            1470

AAG TAC CTT TAT AAA AGC AAA TTG TTT ACC TCA GAG TTG GGT GTC ACA          4524
Lys Tyr Leu Tyr Lys Ser Lys Leu Phe Thr Ser Glu Leu Gly Val Thr
         1475            1480            1485

GAA CAT GTT GAA GGA GAC CCT TGC AAA TTT GCA CTG TGG GTG GGG AGA          4572
Glu His Val Glu Gly Asp Pro Cys Lys Phe Ala Leu Trp Val Gly Arg

-continued

```
              1490               1495                1500
ACA CCA ACT TCA GAT AAT AAA ATT GTC CTT AAG GCT TCC AGC ATA GAG    4620
Thr Pro Thr Ser Asp Asn Lys Ile Val Leu Lys Ala Ser Ser Ile Glu
Thr Pro Thr Ser Asp Asn Lys Ile Val Leu Lys Ala Ser Ser Ile Glu
            1505                1510                1515

AAC AAG CAG GAC TGG ATA AAG CAT ATC CGC GAA GTC ATC CAG GAG CGG    4668
Asn Lys Gln Asp Trp Ile Lys His Ile Arg Glu Val Ile Gln Glu Arg
        1520                1525                1530

ACG ATC CAC CTG AAG GGA GCC CTG AAG GAG CCC ATT CAC ATC CCT AAG    4716
Thr Ile His Leu Lys Gly Ala Leu Lys Glu Pro Ile His Ile Pro Lys
1535                1540                1545                1550

ACC GCT CCC GCC ACA AGA CAG AAG GGA AGG AGG GAT GGA GAG GAT CTG    4764
Thr Ala Pro Ala Thr Arg Gln Lys Gly Arg Arg Asp Gly Glu Asp Leu
                1555                1560                1565

GAC AGC CAA GGA GAC GGC AGC AGC CAG CCT GAT ACG ATT TCC ATC GCC    4812
Asp Ser Gln Gly Asp Gly Ser Ser Gln Pro Asp Thr Ile Ser Ile Ala
                    1570                1575                1580

TCA CGG ACG TCT CAG AAC ACG CTG GAC AGC GAT AAG CTC TCT GGT GGC    4860
Ser Arg Thr Ser Gln Asn Thr Leu Asp Ser Asp Lys Leu Ser Gly Gly
                1585                1590                1595

TGT GAG CTG ACA GTG GTG ATC CAT GAC TTC ACC GCT TGC AAC AGC AAC    4908
Cys Glu Leu Thr Val Val Ile His Asp Phe Thr Ala Cys Asn Ser Asn
            1600                1605                1610

GAG CTG ACC ATC CGA CGG GGC CAG ACC GTG GAA GTT CTG GAG CGG CCG    4956
Glu Leu Thr Ile Arg Arg Gly Gln Thr Val Glu Val Leu Glu Arg Pro
1615                1620                1625                1630

CAT GAC AAG CCT GAC TGG TGT CTG GTG CGG ACC ACT GAC CGC TCC CCA    5004
His Asp Lys Pro Asp Trp Cys Leu Val Arg Thr Thr Asp Arg Ser Pro
                1635                1640                1645

GCG GCA GAA GGC CTG GTC CCC TGT GGT TCA CTG TGC ATC GCC CAC TCC    5052
Ala Ala Glu Gly Leu Val Pro Cys Gly Ser Leu Cys Ile Ala His Ser
                    1650                1655                1660

AGA AGT AGC ATG GAA ATG GAG GGC ATC TTC AAC CAC AAA GAC TCG CTC    5100
Arg Ser Ser Met Glu Met Glu Gly Ile Phe Asn His Lys Asp Ser Leu
                1665                1670                1675

TCC GTC TCC AGC AAT GAC GCC AGT CCA CCC GCA TCC GTG GCT TCC CTC    5148
Ser Val Ser Ser Asn Asp Ala Ser Pro Pro Ala Ser Val Ala Ser Leu
            1680                1685                1690

CAG CCC CAC ATG ATC GGG GCC CAG AGC TCG CCG GGC CCC AAG CGG CCG    5196
Gln Pro His Met Ile Gly Ala Gln Ser Ser Pro Gly Pro Lys Arg Pro
1695                1700                1705                1710

GGC AAC ACC CTG CGC AAG TGG CTC ACC AGC CCC GTG CGG CGG CTC AGC    5244
Gly Asn Thr Leu Arg Lys Trp Leu Thr Ser Pro Val Arg Arg Leu Ser
                1715                1720                1725

AGC GGC AAG GCC GAC GGG CAC GTG AAG AAG CTG GCG CAC AAG CAC AAG    5292
Ser Gly Lys Ala Asp Gly His Val Lys Lys Leu Ala His Lys His Lys
                    1730                1735                1740

AAG AGC CGC GAG GTC CGC AAG AGC GCC GAC GCC GGC TCG CAG AAG GAC    5340
Lys Ser Arg Glu Val Arg Lys Ser Ala Asp Ala Gly Ser Gln Lys Asp
                1745                1750                1755

TCC GAC GAC AGT GCG GCC ACC CCG CAG GAC GAG ACG GTC GAG GAG AGA    5388
Ser Asp Asp Ser Ala Ala Thr Pro Gln Asp Glu Thr Val Glu Glu Arg
                1760                1765                1770

GGC CGG AAC GAG GGC CTG AGC AGC GGT ACT CTC TCC AAA TCC TCC TCC    5436
Gly Arg Asn Glu Gly Leu Ser Ser Gly Thr Leu Ser Lys Ser Ser Ser
1775                1780                1785                1790

TCG GGG ATG CAG AGC TGT GGA GAA GAG GAA GGC GAG GAG GGG GCC GAC    5484
Ser Gly Met Gln Ser Cys Gly Glu Glu Glu Gly Glu Glu Gly Ala Asp
                1795                1800                1805

GCC GTG CCC CTG CCG CCA CCC ATG GCC ATC CAG CAG CAC AGC CTC CTC    5532
Ala Val Pro Leu Pro Pro Pro Met Ala Ile Gln Gln His Ser Leu Leu
```

-continued

|  |  |  |  |
|---|---|---|---|
| 1810 | 1815 | 1820 | |
| CAG CCA GAC TCA CAG GAT GAC AAG GCC TCT TCT CGG TTA TTA GTC CGC | | | 5580 |
| Gln Pro Asp Ser Gln Asp Asp Lys Ala Ser Ser Arg Leu Leu Val Arg | | | |
|  1825  1830  1835  | | | |
| CCC ACC AGC TCC GAA ACA CCG AGT GCA GCC GAG CTC GTC AGT GCA ATT | | | 5628 |
| Pro Thr Ser Ser Glu Thr Pro Ser Ala Ala Glu Leu Val Ser Ala Ile | | | |
|  1840  1845  1850 | | | |
| GAG GAA CTC GTG AAA AGC AAG ATG GCA CTG GAG GAT CGC CCC AGC TCA | | | 5676 |
| Glu Glu Leu Val Lys Ser Lys Met Ala Leu Glu Asp Arg Pro Ser Ser | | | |
| 1855  1860  1865  1870 | | | |
| CTC CTT GTT GAC CAG GGA GAT AGT AGC AGC CCT TCC TTC AAC CCT TCG | | | 5724 |
| Leu Leu Val Asp Gln Gly Asp Ser Ser Ser Pro Ser Phe Asn Pro Ser | | | |
|  1875  1880  1885 | | | |
| GAT AAT TCC CTT CTC TCT TCC TCC TCG CCC ATT GAT GAG ATG GAA GAA | | | 5772 |
| Asp Asn Ser Leu Leu Ser Ser Ser Ser Pro Ile Asp Glu Met Glu Glu | | | |
|  1890  1895  1900 | | | |
| AGG AAA TCC AGC TCT TTA AAG AGA AGA CAC TAC GTT TTG CAA GAA CTA | | | 5820 |
| Arg Lys Ser Ser Ser Leu Lys Arg Arg His Tyr Val Leu Gln Glu Leu | | | |
|  1905  1910  1915 | | | |
| GTG GAG ACA GAG CGT GAC TAT GTG CGG GAC CTT GGC TAT GTG GTT GAG | | | 5868 |
| Val Glu Thr Glu Arg Asp Tyr Val Arg Asp Leu Gly Tyr Val Val Glu | | | |
| 1920  1925  1930 | | | |
| GGC TAC ATG GCA CTT ATG AAA GAA GAT GGT GTT CCT GAT GAC ATG AAA | | | 5916 |
| Gly Tyr Met Ala Leu Met Lys Glu Asp Gly Val Pro Asp Asp Met Lys | | | |
| 1935  1940  1945  1950 | | | |
| GGA AAA GAC AAA ATT GTG TTC GGC AAC ATC CAT CAG ATT TAC GAC TGG | | | 5964 |
| Gly Lys Asp Lys Ile Val Phe Gly Asn Ile His Gln Ile Tyr Asp Trp | | | |
|  1955  1960  1965 | | | |
| CAC AGA GAC TTT TTT TTA GGA GAG TTA GAG AAG TGC CTT GAA GAT CCA | | | 6012 |
| His Arg Asp Phe Phe Leu Gly Glu Leu Glu Lys Cys Leu Glu Asp Pro | | | |
|  1970  1975  1980 | | | |
| GAA AAA CTA GGA TCC CTT TTT GTT AAA CAC GAG AGA AGG TTG CAC ATG | | | 6060 |
| Glu Lys Leu Gly Ser Leu Phe Val Lys His Glu Arg Arg Leu His Met | | | |
|  1985  1990  (1995) | | | |
| TAC ATA GCT TAT TGT CAA AAT AAA CCA AAG TCT GAG CAC ATT GTC TCA | | | 6108 |
| Tyr Ile Ala Tyr Cys Gln Asn Lys Pro Lys Ser Glu His Ile Val Ser | | | |
| 2000  2005  2010 | | | |
| GAA TAC ATT GAT ACC TTT TTT GAG GAC TTA AAG CAG CGT CTT GGC CAC | | | 6156 |
| Glu Tyr Ile Asp Thr Phe Phe Glu Asp Leu Lys Gln Arg Leu Gly His | | | |
| 2015  2020  2025  2030 | | | |
| AGG TTA CAG CTC ACA GAT CTG TTG ATC AAA CCA GTG CAG AGA ATC ATG | | | 6204 |
| Arg Leu Gln Leu Thr Asp Leu Leu Ile Lys Pro Val Gln Arg Ile Met | | | |
|  2035  2040  2045 | | | |
| AAG TAT CAG CTG TTA CTG AAG GAC TTC CTC AAG TAT TCC AAA AAG GCC | | | 6252 |
| Lys Tyr Gln Leu Leu Leu Lys Asp Phe Leu Lys Tyr Ser Lys Lys Ala | | | |
|  2050  2055  2060 | | | |
| AGC CTG GAT ACA TCA GAA TTA GAG AGA GCT GTG GAA GTC ATG TGC ATA | | | 6300 |
| Ser Leu Asp Thr Ser Glu Leu Glu Arg Ala Val Glu Val Met Cys Ile | | | |
|  2065  2070  2075 | | | |
| GTA CCC AGG CGG TGC AAC GAC ATG ATG AAC GTG GGG CGG CTG CAA GGA | | | 6348 |
| Val Pro Arg Arg Cys Asn Asp Met Met Asn Val Gly Arg Leu Gln Gly | | | |
| 2080  2085  2090 | | | |
| TTC GAC GGG AAA ATC GTT GCC CAG GGT AAA CTG CTC TTG CAG GAC ACA | | | 6396 |
| Phe Asp Gly Lys Ile Val Ala Gln Gly Lys Leu Leu Leu Gln Asp Thr | | | |
| 2095  2100  2105  2110 | | | |
| TTC TTG GTC ACA GAC CAA GAT GCA GGA CTT CTG CCT CGC TGC AGA GAG | | | 6444 |
| Phe Leu Val Thr Asp Gln Asp Ala Gly Leu Leu Pro Arg Cys Arg Glu | | | |
|  2115  2120  2125 | | | |
| AGG CGC ATC TTC CTC TTT GAG CAG ATC GTC ATA TTC AGC GAA CCA CTT | | | 6492 |
| Arg Arg Ile Phe Leu Phe Glu Gln Ile Val Ile Phe Ser Glu Pro Leu | | | |

|       |       |       |       |       |       |       |       |       |       |       |       |       |       |       |       |      |
|-------|-------|-------|-------|-------|-------|-------|-------|-------|-------|-------|-------|-------|-------|-------|-------|------|
|       |       | 2130  |       |       |       | 2135  |       |       |       | 2140  |       |       |       |       |       |      |
| GAT   | AAA   | AAG   | AAG   | GGC   | TTC   | TCC   | ATG   | CCG   | GGA   | TTC   | CTG   | TTT   | AAG   | AAC   | AGT   | 6540 |
| Asp   | Lys   | Lys   | Lys   | Gly   | Phe   | Ser   | Met   | Pro   | Gly   | Phe   | Leu   | Phe   | Lys   | Asn   | Ser   |      |
|       |       | 2145  |       |       |       | 2150  |       |       |       | 2155  |       |       |       |       |       |      |
| ATC   | AAG   | GTG   | AGT   | TGC   | CTT   | TGC   | CTG   | GAG   | GAA   | AAT   | GTG   | GAA   | AAT   | GAT   | CCC   | 6588 |
| Ile   | Lys   | Val   | Ser   | Cys   | Leu   | Cys   | Leu   | Glu   | Glu   | Asn   | Val   | Glu   | Asn   | Asp   | Pro   |      |
|       |       | 2160  |       |       |       | 2165  |       |       |       | 2170  |       |       |       |       |       |      |
| TGT   | AAA   | TTT   | GCT   | CTG   | ACA   | TCG   | AGG   | ACG   | GGT   | GAC   | GTG   | GTA   | GAG   | ACC   | TTC   | 6636 |
| Cys   | Lys   | Phe   | Ala   | Leu   | Thr   | Ser   | Arg   | Thr   | Gly   | Asp   | Val   | Val   | Glu   | Thr   | Phe   |      |
| 2175  |       |       |       | 2180  |       |       |       | 2185  |       |       |       | 2190  |       |       |       |      |
| ATT   | TTG   | CAT   | TCA   | TCT   | AGT   | CCA   | AGT   | GTC   | CGG   | CAA   | ACT   | TGG   | ATC   | CAT   | GAA   | 6684 |
| Ile   | Leu   | His   | Ser   | Ser   | Ser   | Pro   | Ser   | Val   | Arg   | Gln   | Thr   | Trp   | Ile   | His   | Glu   |      |
|       |       | 2195  |       |       |       | 2200  |       |       |       | 2205  |       |       |       |       |       |      |
| ATC   | AAC   | CAA   | ATT   | TTA   | GAA   | AAC   | CAG   | CGC   | AAT   | TTT   | TTA   | AAT   | GCC   | TTG   | ACA   | 6732 |
| Ile   | Asn   | Gln   | Ile   | Leu   | Glu   | Asn   | Gln   | Arg   | Asn   | Phe   | Leu   | Asn   | Ala   | Leu   | Thr   |      |
|       |       | 2210  |       |       |       | 2215  |       |       |       | 2220  |       |       |       |       |       |      |
| TCG   | CCA   | ATC   | GAG   | TAC   | CAG   | AGG   | AAC   | CAC   | AGC   | GGG   | GGC   | GGC   | GGC   | GGC   | GGC   | 6780 |
| Ser   | Pro   | Ile   | Glu   | Tyr   | Gln   | Arg   | Asn   | His   | Ser   | Gly   | Gly   | Gly   | Gly   | Gly   | Gly   |      |
|       |       | 2225  |       |       |       | 2230  |       |       |       | 2235  |       |       |       |       |       |      |
| GGC   | AGC   | GGG   | GCA   | GCG   | GCG   | GGG   | GTG   | GGG   | GCA   | GCG   | GCG   | GCG   | GCG   | GGG   | CCC   | 6828 |
| Gly   | Ser   | Gly   | Ala   | Ala   | Ala   | Gly   | Val   | Gly   | Ala   | Ala   | Ala   | Ala   | Ala   | Gly   | Pro   |      |
|       |       | 2240  |       |       |       | 2245  |       |       |       | 2250  |       |       |       |       |       |      |
| CCA   | GTG   | GCG   | GCA   | GCG   | GCC   | ACA   | GTG   | GCG   | GCC   | CCA   | GCA   | GCT   | GCG   | GCG   | GCG   | 6876 |
| Pro   | Val   | Ala   | Ala   | Ala   | Ala   | Thr   | Val   | Ala   | Ala   | Pro   | Ala   | Ala   | Ala   | Ala   | Ala   |      |
| 2255  |       |       |       | 2260  |       |       |       | 2265  |       |       |       | 2270  |       |       |       |      |
| CCC   | CCA   | GCA   | CGA   | GCA   | GGA   | GCC   | GGC   | CCT   | CCC   | GGA   | TCC   | CCC   | AGC   | CTG   | TCC   | 6924 |
| Pro   | Pro   | Ala   | Arg   | Ala   | Gly   | Ala   | Gly   | Pro   | Pro   | Gly   | Ser   | Pro   | Ser   | Leu   | Ser   |      |
|       |       | 2275  |       |       |       | 2280  |       |       |       | 2285  |       |       |       |       |       |      |
| GAC   | ACC   | ACC   | CCC   | CCG   | TGC   | TGG   | TCT   | CCT   | CTG   | CAG   | CCT   | CGA   | GCC   | AGG   | CAG   | 6972 |
| Asp   | Thr   | Thr   | Pro   | Pro   | Cys   | Trp   | Ser   | Pro   | Leu   | Gln   | Pro   | Arg   | Ala   | Arg   | Gln   |      |
|       |       | 2290  |       |       |       | 2295  |       |       |       | 2300  |       |       |       |       |       |      |
| AGG   | CAG   | ACA   | AGA   | TGT   | CAG   | AGT   | GAA   | AGC   | AGC   | AGC   | AGT   | AGC   | AAC   | ATC   | TCC   | 7020 |
| Arg   | Gln   | Thr   | Arg   | Cys   | Gln   | Ser   | Glu   | Ser   | Ser   | Ser   | Ser   | Ser   | Asn   | Ile   | Ser   |      |
|       |       | 2305  |       |       |       | 2310  |       |       |       | 2315  |       |       |       |       |       |      |
| ACC   | ATG   | TTG   | GTG   | ACA   | CAC   | GAT   | TAC   | ACG   | GCA   | GTG   | AAG   | GAG   | GAT   | GAG   | ATC   | 7068 |
| Thr   | Met   | Leu   | Val   | Thr   | His   | Asp   | Tyr   | Thr   | Ala   | Val   | Lys   | Glu   | Asp   | Glu   | Ile   |      |
|       |       | 2320  |       |       |       | 2325  |       |       |       | 2330  |       |       |       |       |       |      |
| AAC   | GTC   | TAC   | CAA   | GGA   | GAG   | GTC   | GTT   | CAA   | ATT   | CTG   | GCC   | AGC   | AAC   | CAG   | CAG   | 7116 |
| Asn   | Val   | Tyr   | Gln   | Gly   | Glu   | Val   | Val   | Gln   | Ile   | Leu   | Ala   | Ser   | Asn   | Gln   | Gln   |      |
| 2335  |       |       |       | 2340  |       |       |       | 2345  |       |       |       | 2350  |       |       |       |      |
| AAC   | ATG   | TTT   | CTG   | GTG   | TTC   | CGA   | GCC   | GCC   | ACT   | GAC   | CAG   | TGC   | CCC   | GCA   | GCT   | 7164 |
| Asn   | Met   | Phe   | Leu   | Val   | Phe   | Arg   | Ala   | Ala   | Thr   | Asp   | Gln   | Cys   | Pro   | Ala   | Ala   |      |
|       |       | 2355  |       |       |       | 2360  |       |       |       | 2365  |       |       |       |       |       |      |
| GAG   | GGC   | TGG   | ATT   | CCA   | GGC   | TTT   | GTC   | CTG   | GGC   | CAC   | ACC   | AGT   | GCA   | GTC   | ATC   | 7212 |
| Glu   | Gly   | Trp   | Ile   | Pro   | Gly   | Phe   | Val   | Leu   | Gly   | His   | Thr   | Ser   | Ala   | Val   | Ile   |      |
|       |       | 2370  |       |       |       | 2375  |       |       |       | 2380  |       |       |       |       |       |      |
| GTG   | GAG   | AAC   | CCG   | GAC   | GGG   | ACT   | CTC   | AAG   | AAG   | TCA   | ACA   | TCT   | TGG   | CAC   | ACA   | 7260 |
| Val   | Glu   | Asn   | Pro   | Asp   | Gly   | Thr   | Leu   | Lys   | Lys   | Ser   | Thr   | Ser   | Trp   | His   | Thr   |      |
|       |       | 2385  |       |       |       | 2390  |       |       |       | 2395  |       |       |       |       |       |      |
| GCA   | CTC   | CGT   | TTA   | AGG   | AAA   | AAA   | TCT   | GAG   | AAA   | AAA   | GAT   | AAA   | GAC   | GGC   | AAA   | 7308 |
| Ala   | Leu   | Arg   | Leu   | Arg   | Lys   | Lys   | Ser   | Glu   | Lys   | Lys   | Asp   | Lys   | Asp   | Gly   | Lys   |      |
|       |       | 2400  |       |       |       | 2405  |       |       |       | 2410  |       |       |       |       |       |      |
| AGG   | GAA   | GGC   | AAG   | TTA   | GAG   | AAC   | GGT   | TAT   | CGG   | AAG   | TCA   | CGG   | GAA   | GGA   | CTC   | 7356 |
| Arg   | Glu   | Gly   | Lys   | Leu   | Glu   | Asn   | Gly   | Tyr   | Arg   | Lys   | Ser   | Arg   | Glu   | Gly   | Leu   |      |
| 2415  |       |       |       | 2420  |       |       |       | 2425  |       |       |       | 2430  |       |       |       |      |
| AGC   | AAC   | AAG   | GTA   | TCT   | GTG   | AAG   | CTT   | CTC   | AAT   | CCC   | AAC   | TAC   | ATT   | TAT   | GAC   | 7404 |
| Ser   | Asn   | Lys   | Val   | Ser   | Val   | Lys   | Leu   | Leu   | Asn   | Pro   | Asn   | Tyr   | Ile   | Tyr   | Asp   |      |
|       |       | 2435  |       |       |       | 2440  |       |       |       | 2445  |       |       |       |       |       |      |
| GTT   | CCC   | CCA   | GAA   | TTC   | GTC   | ATT   | CCA   | TTG   | AGT   | GAG   | GTC   | ACG   | TGT   | GAG   | ACA   | 7452 |
| Val   | Pro   | Pro   | Glu   | Phe   | Val   | Ile   | Pro   | Leu   | Ser   | Glu   | Val   | Thr   | Cys   | Glu   | Thr   |      |

```
                    2450                2455                2460
GGG GAG ACC GTT GTT CTT AGA TGT CGA GTC TGT GGC CGC CCC AAA GCC       7500
Gly Glu Thr Val Val Leu Arg Cys Arg Val Cys Gly Arg Pro Lys Ala
            2465                2470                2475

TCA ATT ACC TGG AAG GGC CCT GAA CAC AAC ACC TTG AAC AAC GAT GGT       7548
Ser Ile Thr Trp Lys Gly Pro Glu His Asn Thr Leu Asn Asn Asp Gly
        2480                2485                2490

CAC TAC AGC ATC TCC TAC AGT GAC CTG GGA GAG GCC ACG CTG AAG ATT       7596
His Tyr Ser Ile Ser Tyr Ser Asp Leu Gly Glu Ala Thr Leu Lys Ile
2495                2500                2505                2510

GTG GGC GTG ACC ACG GAA GAT GAC GGC ATC TAC ACG TGC ATC GCT GTC       7644
Val Gly Val Thr Thr Glu Asp Asp Gly Ile Tyr Thr Cys Ile Ala Val
            2515                2520                2525

AAT GAC ATG GGT TCA GCC TCA TCA TCG GCC AGC CTG AGG GTC CTA GGT       7692
Asn Asp Met Gly Ser Ala Ser Ser Ser Ala Ser Leu Arg Val Leu Gly
        2530                2535                2540

CCA GGG ATG GAT GGG ATC ATG GTG ACC TGG AAA GAC AAC TTT GAC TCC       7740
Pro Gly Met Asp Gly Ile Met Val Thr Trp Lys Asp Asn Phe Asp Ser
            2545                2550                2555

TTC TAC AGT GAA GTG GCT GAG CTT GGC AGG GGC AGA TTC TCT GTC GTT       7788
Phe Tyr Ser Glu Val Ala Glu Leu Gly Arg Gly Arg Phe Ser Val Val
        2560                2565                2570

AAG AAA TGT GAT CAG AAA GGA ACC AAG CGA GCA GTG GCC ACT AAG TTT       7836
Lys Lys Cys Asp Gln Lys Gly Thr Lys Arg Ala Val Ala Thr Lys Phe
2575                2580                2585                2590

GTG AAC AAG AAG TTG ATG AAG CGC GAC CAG GTC ACC CAT GAG CTT GGC       7884
Val Asn Lys Lys Leu Met Lys Arg Asp Gln Val Thr His Glu Leu Gly
            2595                2600                2605

ATC CTG CAG AGC CTC CAG CAC CCC CTG CTT GTC GGC CTC CTC GAC ACC       7932
Ile Leu Gln Ser Leu Gln His Pro Leu Leu Val Gly Leu Leu Asp Thr
        2610                2615                2620

TTT GAG ACC CCC ACC AGC TAC ATC CTG GTC TTA GAA ATG GCT GAC CAG       7980
Phe Glu Thr Pro Thr Ser Tyr Ile Leu Val Leu Glu Met Ala Asp Gln
            2625                2630                2635

GGT CGC CTC CTG GAC TGC GTG GTG CGA TGG GGA AGC CTC ACT GAA GGG       8028
Gly Arg Leu Leu Asp Cys Val Val Arg Trp Gly Ser Leu Thr Glu Gly
        2640                2645                2650

AAG ATC AGG GCG CAC CTG GGG GAG GTT CTG GAA GCT GTC CGG TAC CTG       8076
Lys Ile Arg Ala His Leu Gly Glu Val Leu Glu Ala Val Arg Tyr Leu
2655                2660                2665                2670

CAC AAC TGC AGG ATA GCA CAC CTG GAC CTA AAG CCT GAG AAT ATC CTG       8124
His Asn Cys Arg Ile Ala His Leu Asp Leu Lys Pro Glu Asn Ile Leu
            2675                2680                2685

GTG GAT GAG AGT TTA GCC AAG CCA ACC ATC AAA CTG GCT GAC TTT GGA       8172
Val Asp Glu Ser Leu Ala Lys Pro Thr Ile Lys Leu Ala Asp Phe Gly
        2690                2695                2700

GAT GCT GTT CAG CTC AAC ACG ACC TAC TAC ATC CAC CAG TTA CTG GGG       8220
Asp Ala Val Gln Leu Asn Thr Thr Tyr Tyr Ile His Gln Leu Leu Gly
            2705                2710                2715

AAC CCT GAA TTC GCA GCC CCT GAA ATC ATC CTC GGG AAC CCT GTC TCC       8268
Asn Pro Glu Phe Ala Ala Pro Glu Ile Ile Leu Gly Asn Pro Val Ser
        2720                2725                2730

CTG ACC TCG GAT ACG TGG AGT GTT GGA GTG CTC ACA TAC GTA CTT CTT       8316
Leu Thr Ser Asp Thr Trp Ser Val Gly Val Leu Thr Tyr Val Leu Leu
2735                2740                2745                2750

AGT GGC GTG TCC CCC TTC CTG GAT GAC AGT GTG GAA GAG ACC TGC CTG       8364
Ser Gly Val Ser Pro Phe Leu Asp Asp Ser Val Glu Glu Thr Cys Leu
            2755                2760                2765

AAC ATT TGC CGC TTA GAC TTT AGC TTC CCA GAT GAC TAC TTT AAA GGA       8412
Asn Ile Cys Arg Leu Asp Phe Ser Phe Pro Asp Asp Tyr Phe Lys Gly
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     |     | 2770 |     |     |     | 2775 |     |     |     | 2780 |     |     |     |      |
| GTG | AGC | CAG | AAG | GCC | AAG | GAG | TTC | GTG | TGC | TTC | CTC | CTG | CAG | GAG | GAC  | 8460 |
| Val | Ser | Gln | Lys | Ala | Lys | Glu | Phe | Val | Cys | Phe | Leu | Leu | Gln | Glu | Asp  |
|     |     | 2785 |     |     |     | 2790 |     |     |     | 2795 |     |     |     |     |      |
| CCC | GCC | AAG | CGT | CCC | TCG | GCT | GCG | CTG | GCC | CTC | CAG | GAG | CAG | TGG | CTG  | 8508 |
| Pro | Ala | Lys | Arg | Pro | Ser | Ala | Ala | Leu | Ala | Leu | Gln | Glu | Gln | Trp | Leu  |
|     | 2800 |     |     |     | 2805 |     |     |     | 2810 |     |     |     |     |     |      |
| CAG | GCC | GGC | AAC | GGC | AGA | AGC | ACG | GGC | GTC | CTC | GAC | ACG | TCC | AGA | CTG  | 8556 |
| Gln | Ala | Gly | Asn | Gly | Arg | Ser | Thr | Gly | Val | Leu | Asp | Thr | Ser | Arg | Leu  |
| 2815 |     |     |     | 2820 |     |     |     | 2825 |     |     |     |     |     | 2830 |     |
| ACT | TCC | TTC | ATT | GAG | CGG | CGC | AAA | CAC | CAG | AAT | GAT | GTT | CGA | CCT | ATC  | 8604 |
| Thr | Ser | Phe | Ile | Glu | Arg | Arg | Lys | His | Gln | Asn | Asp | Val | Arg | Pro | Ile  |
|     |     |     | 2835 |     |     |     | 2840 |     |     |     |     | 2845 |     |     |      |
| CGT | AGC | ATT | AAA | AAC | TTT | CTG | CAG | AGC | AGG | CTT | CTG | CCT | AGA | G   |      | 8647 |
| Arg | Ser | Ile | Lys | Asn | Phe | Leu | Gln | Ser | Arg | Leu | Leu | Pro | Arg |     |      |
|     |     | 2850 |     |     |     | 2855 |     |     |     | 286 |     |     |     |     |      |

TTTGACCTAT CCAGAAGTTC TTTCTCATTC TCTTTCACCT GCCAATCAGC TGTTAATCTG 8707

AATTTTCAAG AGAAAACAAG CAAACATAAC TGATCAGCTG CCGGTATGTT CATCGTGTGA 8767

AATTGCATTC CAAGTGAGCT GTGCTCAGCA GTGCTTGGAC ACAGAGCTGC AAGCTGCGCT 8827

GGGGTGGAGG ACCGTCACTT ACACTCTGCC AAGGACGGAG GTCGCATTGC TGTATCACAG 8887

TATTTTTTAC GGATTTCTG 8906

(2) INFORMATION FOR SEQ ID NO:2:

(i) SEQUENCE CHARACTERISTICS:
        (A) LENGTH: 2860 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Ala Met Asp Val Leu Pro Ile Leu Lys Glu Lys Val Ala Tyr
  1               5                  10                  15

Leu Ser Gly Gly Arg Asp Lys Arg Gly Gly Pro Ile Leu Thr Phe Pro
             20                  25                  30

Ala Arg Ser Asn His Asp Arg Ile Arg Gln Glu Asp Leu Arg Arg Leu
         35                  40                  45

Ile Ser Tyr Leu Ala Cys Ile Pro Ser Glu Glu Val Cys Lys Arg Gly
 50                  55                  60

Phe Thr Val Ile Val Asp Met Arg Gly Ser Lys Trp Asp Ser Ile Lys
 65                  70                  75                  80

Pro Leu Leu Lys Ile Leu Gln Glu Ser Phe Pro Cys Cys Ile His Val
                 85                  90                  95

Ala Leu Ile Ile Lys Pro Asp Asn Phe Trp Gln Lys Gln Arg Thr Asn
            100                 105                 110

Phe Gly Ser Ser Lys Phe Glu Phe Glu Thr Asn Met Val Ser Leu Glu
        115                 120                 125

Gly Leu Thr Lys Val Val Asp Pro Ser Gln Leu Thr Pro Glu Phe Asp
    130                 135                 140

Gly Cys Leu Glu Tyr Asn His Glu Glu Trp Ile Glu Ile Arg Val Ala
145                 150                 155                 160

Phe Glu Asp Tyr Ile Ser Asn Ala Thr His Met Leu Ser Arg Leu Glu
                165                 170                 175

Glu Leu Gln Asp Ile Leu Ala Lys Lys Glu Leu Pro Gln Asp Leu Glu
            180                 185                 190
```

-continued

```
Gly Ala Arg Asn Met Ile Glu Glu His Ser Gln Leu Lys Lys Val
        195                 200                 205
Ile Lys Ala Pro Ile Glu Asp Leu Asp Leu Glu Gly Gln Lys Leu Leu
210                 215                 220
Gln Arg Ile Gln Ser Ser Glu Ser Phe Pro Lys Asn Ser Gly Ser
225                 230                 235                 240
Gly Asn Ala Asp Leu Gln Asn Leu Leu Pro Lys Val Ser Thr Met Leu
                245                 250                 255
Asp Arg Leu His Ser Thr Arg Gln His Leu His Gln Met Trp His Val
            260                 265                 270
Arg Lys Leu Lys Leu Asp Gln Cys Phe Gln Leu Arg Leu Phe Glu Gln
        275                 280                 285
Asp Ala Glu Lys Met Phe Asp Trp Ile Thr His Asn Lys Gly Leu Phe
    290                 295                 300
Leu Asn Ser Tyr Thr Glu Ile Gly Thr Ser His Pro His Ala Met Glu
305                 310                 315                 320
Leu Gln Thr Gln His Asn His Phe Ala Met Asn Cys Met Asn Val Tyr
                325                 330                 335
Val Asn Ile Asn Arg Ile Met Ser Val Ala Asn Arg Leu Val Glu Ser
            340                 345                 350
Gly His Tyr Ala Ser Gln Gln Ile Arg Gln Ile Ala Ser Gln Leu Glu
        355                 360                 365
Gln Glu Trp Lys Ala Phe Ala Ala Leu Asp Glu Arg Ser Thr Leu
    370                 375                 380
Leu Asp Met Ser Ser Ile Phe His Gln Lys Ala Glu Lys Tyr Met Ser
385                 390                 395                 400
Asn Val Asp Ser Trp Cys Lys Ala Cys Gly Glu Val Asp Leu Pro Ser
                405                 410                 415
Glu Leu Gln Asp Leu Glu Asp Ala Ile His His Gln Gly Ile Tyr
            420                 425                 430
Glu His Ile Thr Leu Ala Tyr Ser Glu Val Ser Gln Asp Gly Lys Ser
        435                 440                 445
Leu Leu Asp Lys Leu Gln Arg Pro Leu Thr Pro Gly Ser Ser Asp Ser
    450                 455                 460
Leu Thr Ala Ser Ala Asn Tyr Ser Lys Ala Val His Val Leu Asp
465                 470                 475                 480
Val Ile His Glu Val Leu His His Gln Arg His Val Arg Thr Ile Trp
                485                 490                 495
Gln His Arg Lys Val Arg Leu His Gln Arg Leu Gln Leu Cys Val Phe
            500                 505                 510
Gln Gln Glu Val Gln Val Leu Asp Trp Ile Glu Asn His Gly Glu
        515                 520                 525
Ala Phe Leu Ser Lys His Thr Gly Val Gly Lys Ser Leu His Arg Ala
    530                 535                 540
Arg Ala Leu Gln Lys Arg His Glu Asp Phe Glu Glu Val Ala Gln Asn
545                 550                 555                 560
Thr Tyr Thr Asn Ala Asp Lys Leu Leu Glu Ala Ala Glu Gln Leu Ala
                565                 570                 575
Gln Thr Gly Glu Cys Asp Pro Glu Glu Ile Tyr Gln Ala Ala His Gln
            580                 585                 590
Leu Glu Asp Arg Ile Gln Asp Phe Val Arg Val Glu Gln Arg Lys
        595                 600                 605
Ile Leu Leu Asp Met Ser Val Ser Phe His Thr His Val Lys Glu Leu
    610                 615                 620
```

-continued

Trp Thr Trp Leu Glu Glu Leu Gln Lys Glu Leu Leu Asp Asp Val Tyr
625             630              635              640

Ala Glu Ser Val Glu Ala Val Gln Asp Leu Ile Lys Arg Phe Gly Gln
            645              650              655

Gln Gln Gln Thr Thr Leu Gln Val Thr Val Asn Val Ile Lys Glu Gly
            660              665              670

Glu Asp Leu Ile Gln Gln Leu Arg Asp Ser Ala Ile Ser Ser Asn Lys
            675              680              685

Thr Pro His Asn Ser Ser Ile Asn His Ile Glu Thr Val Leu Gln Gln
690              695              700

Leu Asp Glu Ala Gln Ser Gln Met Glu Glu Leu Phe Gln Arg Lys
705             710              715              720

Ile Lys Leu Glu Leu Phe Leu His Val Arg Ile Phe Glu Arg Asp Ala
                725              730              735

Ile Asp Ile Ile Ser Asp Leu Glu Ser Trp Asn Asp Glu Leu Ser Gln
            740              745              750

Gln Met Asn Asp Phe Asp Thr Glu Asp Leu Thr Ile Ala Glu Gln Arg
            755              760              765

Leu Gln His His Ala Asp Lys Ala Leu Thr Met Asn Asn Leu Thr Phe
770              775              780

Asp Val Ile His Gln Gly Gln Asp Leu Leu Gln Tyr Val Asn Glu Val
785             790              795              800

Gln Ala Ser Gly Val Glu Leu Leu Cys Asp Arg Asp Val Asp Met Ala
            805              810              815

Thr Arg Val Gln Asp Leu Leu Glu Phe Leu His Glu Lys Gln Gln Glu
            820              825              830

Leu Asp Leu Ala Ala Glu Gln His Arg Lys His Leu Glu Gln Cys Val
835             840              845

Gln Leu Arg His Leu Gln Ala Glu Val Lys Gln Val Leu Gly Trp Ile
850             855              860

Arg Asn Gly Glu Ser Met Leu Asn Ala Gly Leu Ile Thr Ala Ser Ser
865             870              875              880

Leu Gln Glu Ala Glu Gln Leu Gln Arg Glu His Glu Gln Phe Gln His
            885              890              895

Ala Ile Glu Lys Thr His Gln Ser Ala Leu Gln Val Gln Gln Lys Ala
            900              905              910

Glu Ala Met Leu Gln Ala Asn His Tyr Asp Met Asp Met Ile Arg Asp
            915              920              925

Cys Ala Glu Lys Val Ala Ser His Trp Gln Gln Leu Met Leu Lys Met
930             935              940

Glu Asp Arg Leu Lys Leu Val Asn Ala Ser Val Ala Phe Tyr Lys Thr
945             950              955              960

Ser Glu Gln Val Cys Ser Val Leu Glu Ser Leu Glu Gln Glu Tyr Lys
            965              970              975

Arg Glu Glu Asp Trp Cys Gly Gly Ala Asp Lys Leu Gly Pro Asn Ser
            980              985              990

Glu Thr Asp His Val Thr Pro Met Ile Ser Lys His Leu Glu Gln Lys
            995              1000             1005

Glu Ala Phe Leu Lys Ala Cys Thr Leu Ala Arg Arg Asn Ala Asp Val
            1010             1015             1020

Phe Leu Lys Tyr Leu His Arg Asn Ser Val Asn Met Pro Gly Met Val
1025             1030             1035             1040

Thr His Ile Lys Ala Pro Glu Gln Gln Val Lys Asn Ile Leu Asn Glu

```
                    1045                1050                1055
Leu Phe Gln Arg Glu Asn Arg Val Leu His Tyr Trp Thr Met Arg Lys
                1060                1065                1070

Arg Arg Leu Asp Gln Cys Gln Gln Tyr Val Val Phe Glu Arg Ser Ala
            1075                1080                1085

Lys Gln Ala Leu Glu Trp Ile His Asp Asn Gly Glu Phe Tyr Leu Ser
        1090                1095                1100

Thr His Thr Ser Thr Gly Ser Ser Ile Gln His Thr Gln Glu Leu Leu
1105                1110                1115                1120

Lys Glu His Glu Glu Phe Gln Ile Thr Ala Lys Gln Thr Lys Glu Arg
                1125                1130                1135

Val Lys Leu Leu Ile Gln Leu Ala Asp Gly Phe Cys Glu Lys Gly His
            1140                1145                1150

Ala His Ala Ala Glu Ile Lys Lys Cys Val Thr Ala Val Asp Lys Arg
        1155                1160                1165

Tyr Arg Asp Phe Ser Leu Arg Met Glu Lys Tyr Arg Thr Ser Leu Glu
    1170                1175                1180

Lys Ala Leu Gly Ile Ser Ser Asp Ser Asn Lys Ser Ser Lys Ser Leu
1185                1190                1195                1200

Gln Leu Asp Ile Ile Pro Ala Ser Ile Pro Gly Ser Glu Val Lys Leu
                1205                1210                1215

Arg Asp Ala Ala His Glu Leu Asn Glu Glu Lys Arg Lys Ser Ala Arg
            1220                1225                1230

Arg Lys Glu Phe Ile Met Ala Glu Leu Ile Gln Thr Glu Lys Ala Tyr
        1235                1240                1245

Val Arg Asp Leu Arg Glu Cys Met Asp Thr Tyr Leu Trp Glu Met Thr
    1250                1255                1260

Ser Gly Val Glu Glu Ile Pro Pro Gly Ile Val Asn Lys Glu Leu Ile
1265                1270                1275                1280

Ile Phe Gly Asn Met Gln Glu Ile Tyr Glu Phe His Asn Asn Ile Phe
                1285                1290                1295

Leu Lys Glu Leu Glu Lys Tyr Glu Gln Leu Pro Glu Asp Val Gly His
            1300                1305                1310

Cys Phe Val Thr Trp Ala Asp Lys Phe Gln Met Tyr Val Thr Tyr Cys
        1315                1320                1325

Lys Asn Lys Pro Asp Ser Thr Gln Leu Ile Leu Glu His Ala Gly Ser
    1330                1335                1340

Tyr Phe Asp Glu Ile Gln Gln Arg His Gly Leu Ala Asn Ser Ile Ser
1345                1350                1355                1360

Ser Tyr Leu Ile Lys Pro Val Gln Arg Ile Thr Lys Tyr Gln Leu Leu
                1365                1370                1375

Leu Lys Glu Leu Leu Thr Cys Cys Glu Glu Gly Lys Gly Glu Ile Lys
            1380                1385                1390

Asp Gly Leu Glu Val Met Leu Ser Val Pro Lys Arg Ala Asn Asp Ala
        1395                1400                1405

Met His Leu Ser Met Leu Glu Gly Phe Asp Glu Asn Ile Glu Ser Gln
    1410                1415                1420

Gly Glu Leu Ile Leu Gln Glu Ser Phe Gln Val Trp Asp Pro Lys Thr
1425                1430                1435                1440

Leu Ile Arg Lys Gly Arg Glu Arg His Leu Phe Leu Phe Glu Met Ser
                1445                1450                1455

Leu Val Phe Ser Lys Glu Val Lys Asp Ser Ser Gly Arg Ser Lys Tyr
            1460                1465                1470
```

-continued

```
Leu Tyr Lys Ser Lys Leu Phe Thr Ser Glu Leu Gly Val Thr Glu His
         1475                1480                1485
Val Glu Gly Asp Pro Cys Lys Phe Ala Leu Trp Val Gly Arg Thr Pro
 1490                1495                1500
Thr Ser Asp Asn Lys Ile Val Leu Lys Ala Ser Ser Ile Glu Asn Lys
 1505                1510                1515                1520
Gln Asp Trp Ile Lys His Ile Arg Glu Val Ile Gln Glu Arg Thr Ile
              1525                1530                1535
His Leu Lys Gly Ala Leu Lys Glu Pro Ile His Ile Pro Lys Thr Ala
         1540                1545                1550
Pro Ala Thr Arg Gln Lys Gly Arg Arg Asp Gly Glu Asp Leu Asp Ser
 1555                1560                1565
Gln Gly Asp Gly Ser Ser Gln Pro Asp Thr Ile Ser Ile Ala Ser Arg
 1570                1575                1580
Thr Ser Gln Asn Thr Leu Asp Ser Asp Lys Leu Ser Gly Gly Cys Glu
 1585                1590                1595                1600
Leu Thr Val Val Ile His Asp Phe Thr Ala Cys Asn Ser Asn Glu Leu
              1605                1610                1615
Thr Ile Arg Arg Gly Gln Thr Val Glu Val Leu Glu Arg Pro His Asp
              1620                1625                1630
Lys Pro Asp Trp Cys Leu Val Arg Thr Thr Asp Arg Ser Pro Ala Ala
              1635                1640                1645
Glu Gly Leu Val Pro Cys Gly Ser Leu Cys Ile Ala His Ser Arg Ser
 1650                1655                1660
Ser Met Glu Met Glu Gly Ile Phe Asn His Lys Asp Ser Leu Ser Val
 1665                1670                1675                1680
Ser Ser Asn Asp Ala Ser Pro Pro Ala Ser Val Ala Ser Leu Gln Pro
              1685                1690                1695
His Met Ile Gly Ala Gln Ser Ser Pro Gly Pro Lys Arg Pro Gly Asn
              1700                1705                1710
Thr Leu Arg Lys Trp Leu Thr Ser Pro Val Arg Arg Leu Ser Ser Gly
              1715                1720                1725
Lys Ala Asp Gly His Val Lys Lys Leu Ala His Lys His Lys Lys Ser
         1730                1735                1740
Arg Glu Val Arg Lys Ser Ala Asp Ala Gly Ser Gln Lys Asp Ser Asp
 1745                1750                1755                1760
Asp Ser Ala Ala Thr Pro Gln Asp Glu Thr Val Glu Glu Arg Gly Arg
              1765                1770                1775
Asn Glu Gly Leu Ser Ser Gly Thr Leu Ser Lys Ser Ser Ser Ser Gly
              1780                1785                1790
Met Gln Ser Cys Gly Glu Glu Gly Glu Gly Ala Asp Ala Val
         1795                1800                1805
Pro Leu Pro Pro Pro Met Ala Ile Gln Gln His Ser Leu Leu Gln Pro
 1810                1815                1820
Asp Ser Gln Asp Asp Lys Ala Ser Ser Arg Leu Leu Val Arg Pro Thr
 1825                1830                1835                1840
Ser Ser Glu Thr Pro Ser Ala Ala Glu Leu Val Ser Ala Ile Glu Glu
              1845                1850                1855
Leu Val Lys Ser Lys Met Ala Leu Glu Asp Arg Pro Ser Ser Leu Leu
              1860                1865                1870
Val Asp Gln Gly Asp Ser Ser Ser Pro Ser Phe Asn Pro Ser Asp Asn
         1875                1880                1885
Ser Leu Leu Ser Ser Ser Ser Pro Ile Asp Glu Met Glu Glu Arg Lys
         1890                1895                1900
```

```
Ser Ser Ser Leu Lys Arg Arg His Tyr Val Leu Gln Glu Leu Val Glu
1905                1910                1915                1920

Thr Glu Arg Asp Tyr Val Arg Asp Leu Gly Tyr Val Glu Gly Tyr
            1925                1930                1935

Met Ala Leu Met Lys Glu Asp Gly Val Pro Asp Asp Met Lys Gly Lys
            1940                1945                1950

Asp Lys Ile Val Phe Gly Asn Ile His Gln Ile Tyr Asp Trp His Arg
            1955                1960                1965

Asp Phe Phe Leu Gly Glu Leu Glu Lys Cys Leu Glu Asp Pro Glu Lys
            1970                1975                1980

Leu Gly Ser Leu Phe Val Lys His Glu Arg Arg Leu His Met Tyr Ile
1985                1990                1995                2000

Ala Tyr Cys Gln Asn Lys Pro Lys Ser Glu His Ile Val Ser Glu Tyr
            2005                2010                2015

Ile Asp Thr Phe Phe Glu Asp Leu Lys Gln Arg Leu Gly His Arg Leu
            2020                2025                2030

Gln Leu Thr Asp Leu Leu Ile Lys Pro Val Gln Arg Ile Met Lys Tyr
            2035                2040                2045

Gln Leu Leu Leu Lys Asp Phe Leu Lys Tyr Ser Lys Lys Ala Ser Leu
            2050                2055                2060

Asp Thr Ser Glu Leu Glu Arg Ala Val Glu Val Met Cys Ile Val Pro
2065                2070                2075                2080

Arg Arg Cys Asn Asp Met Met Asn Val Gly Arg Leu Gln Gly Phe Asp
            2085                2090                2095

Gly Lys Ile Val Ala Gln Gly Lys Leu Leu Leu Gln Asp Thr Phe Leu
            2100                2105                2110

Val Thr Asp Gln Asp Ala Gly Leu Leu Pro Arg Cys Arg Glu Arg Arg
            2115                2120                2125

Ile Phe Leu Phe Glu Gln Ile Val Ile Phe Ser Glu Pro Leu Asp Lys
            2130                2135                2140

Lys Lys Gly Phe Ser Met Pro Gly Phe Leu Phe Lys Asn Ser Ile Lys
2145                2150                2155                2160

Val Ser Cys Leu Cys Leu Glu Glu Asn Val Glu Asn Asp Pro Cys Lys
            2165                2170                2175

Phe Ala Leu Thr Ser Arg Thr Gly Asp Val Val Glu Thr Phe Ile Leu
            2180                2185                2190

His Ser Ser Pro Ser Val Arg Gln Thr Trp Ile His Glu Ile Asn
            2195                2200                2205

Gln Ile Leu Glu Asn Gln Arg Asn Phe Leu Asn Ala Leu Thr Ser Pro
            2210                2215                2220

Ile Glu Tyr Gln Arg Asn His Ser Gly Gly Gly Gly Gly Gly Gly Ser
2225                2230                2235                2240

Gly Ala Ala Ala Gly Val Gly Ala Ala Ala Ala Gly Pro Pro Val
            2245                2250                2255

Ala Ala Ala Ala Thr Val Ala Ala Pro Ala Ala Ala Ala Pro Pro
            2260                2265                2270

Ala Arg Ala Gly Ala Gly Pro Pro Gly Ser Pro Ser Leu Ser Asp Thr
            2275                2280                2285

Thr Pro Pro Cys Trp Ser Pro Leu Gln Pro Arg Ala Arg Gln Arg Gln
            2290                2295                2300

Thr Arg Cys Gln Ser Glu Ser Ser Ser Ser Asn Ile Ser Thr Met
2305                2310                2315                2320

Leu Val Thr His Asp Tyr Thr Ala Val Lys Glu Asp Glu Ile Asn Val
```

-continued

```
                2325                2330                2335
Tyr Gln Gly Glu Val Val Gln Ile Leu Ala Ser Asn Gln Gln Asn Met
                2340                2345                2350
Phe Leu Val Phe Arg Ala Ala Thr Asp Gln Cys Pro Ala Ala Glu Gly
                2355                2360                2365
Trp Ile Pro Gly Phe Val Leu Gly His Thr Ser Ala Val Ile Val Glu
                2370                2375                2380
Asn Pro Asp Gly Thr Leu Lys Lys Ser Thr Ser Trp His Thr Ala Leu
2385                2390                2395                2400
Arg Leu Arg Lys Lys Ser Glu Lys Asp Lys Asp Gly Lys Arg Glu
                2405                2410                2415
Gly Lys Leu Glu Asn Gly Tyr Arg Lys Ser Arg Glu Gly Leu Ser Asn
                2420                2425                2430
Lys Val Ser Val Lys Leu Leu Asn Pro Asn Tyr Ile Tyr Asp Val Pro
                2435                2440                2445
Pro Glu Phe Val Ile Pro Leu Ser Glu Val Thr Cys Glu Thr Gly Glu
                2450                2455                2460
Thr Val Val Leu Arg Cys Arg Val Cys Gly Arg Pro Lys Ala Ser Ile
2465                2470                2475                2480
Thr Trp Lys Gly Pro Glu His Asn Thr Leu Asn Asn Asp Gly His Tyr
                2485                2490                2495
Ser Ile Ser Tyr Ser Asp Leu Gly Glu Ala Thr Leu Lys Ile Val Gly
                2500                2505                2510
Val Thr Thr Glu Asp Asp Gly Ile Tyr Thr Cys Ile Ala Val Asn Asp
                2515                2520                2525
Met Gly Ser Ala Ser Ser Ala Ser Leu Arg Val Leu Gly Pro Gly
                2530                2535                2540
Met Asp Gly Ile Met Val Thr Trp Lys Asp Asn Phe Asp Ser Phe Tyr
2545                2550                2555                2560
Ser Glu Val Ala Glu Leu Gly Arg Gly Arg Phe Ser Val Val Lys Lys
                2565                2570                2575
Cys Asp Gln Lys Gly Thr Lys Arg Ala Val Ala Thr Lys Phe Val Asn
                2580                2585                2590
Lys Lys Leu Met Lys Arg Asp Gln Val Thr His Glu Leu Gly Ile Leu
                2595                2600                2605
Gln Ser Leu Gln His Pro Leu Leu Val Gly Leu Leu Asp Thr Phe Glu
                2610                2615                2620
Thr Pro Thr Ser Tyr Ile Leu Val Leu Glu Met Ala Asp Gln Gly Arg
2625                2630                2635                2640
Leu Leu Asp Cys Val Val Arg Trp Gly Ser Leu Thr Glu Gly Lys Ile
                2645                2650                2655
Arg Ala His Leu Gly Glu Val Leu Glu Ala Val Arg Tyr Leu His Asn
                2660                2665                2670
Cys Arg Ile Ala His Leu Asp Leu Lys Pro Glu Asn Ile Leu Val Asp
                2675                2680                2685
Glu Ser Leu Ala Lys Pro Thr Ile Lys Leu Ala Asp Phe Gly Asp Ala
                2690                2695                2700
Val Gln Leu Asn Thr Thr Tyr Tyr Ile His Gln Leu Leu Gly Asn Pro
2705                2710                2715                2720
Glu Phe Ala Ala Pro Glu Ile Ile Leu Gly Asn Pro Val Ser Leu Thr
                2725                2730                2735
Ser Asp Thr Trp Ser Val Gly Val Leu Thr Tyr Val Leu Leu Ser Gly
                2740                2745                2750
```

```
Val Ser Pro Phe Leu Asp Asp Ser Val Glu Glu Thr Cys Leu Asn Ile
    2755                2760                2765

Cys Arg Leu Asp Phe Ser Phe Pro Asp Asp Tyr Phe Lys Gly Val Ser
    2770            2775                2780

Gln Lys Ala Lys Glu Phe Val Cys Phe Leu Leu Gln Glu Asp Pro Ala
2785            2790            2795                    2800

Lys Arg Pro Ser Ala Ala Leu Ala Leu Gln Glu Gln Trp Leu Gln Ala
            2805            2810                    2815

Gly Asn Gly Arg Ser Thr Gly Val Leu Asp Thr Ser Arg Leu Thr Ser
            2820                2825                2830

Phe Ile Glu Arg Arg Lys His Gln Asn Asp Val Arg Pro Ile Arg Ser
        2835            2840                2845

Ile Lys Asn Phe Leu Gln Ser Arg Leu Leu Pro Arg
    2850                2855            2860
```

TRIO MOLECULES AND USES RELATED THERETO

This application claims the benefit of U.S. Provisional Application No. 60/014,214 filed Mar. 27, 1996.

GOVERNMENT FUNDING

Work described herein was supported, in part, by grant CA55547 awarded by the National Institutes of Health. The U.S. government therefore may have certain rights in this invention.

BACKGROUND OF THE INVENTION

In response to environmental signals, a cell changes both its shape and its degree of attachment to a substratum. Changes in cell motility are brought about, in part, by rearrangements of the actin cytoskeleton. Changes in actin are associated with changes in cell morphology, growth, adhesion, and motility (Hall, A. (1994) *Annu. Rev. Cell Biol.* 10, 31–54; Boguski, M. S. and McCormick, F. (1993) *Nature* 366, 643–654; Vojtek, A. B. and Cooper, J. A. (1995) *Cell* 82, 527–529; Takai, Y., et al. (1995) *TIBS* 227–231.). In long bundles, F-actin supports filipodia, finger-like protrusions of the plasma membrane; as a meshwork, F-actin supports sheet-like protrusions of lamellipodia, called ruffles; in bundles coupled to attachment plaques, F-actin stress fibers exert force against a substratum (Zigmone (1996) *Curr. Opin. Cell Biol.* 8:66). This remodeling requires actin polymerization and depolymerization, which is orchestrated in part by members of the rho family of small GTPases (GTP-binding proteins), including rhoA, rac1, and cdc42 (Boguski and McCormick, (1993). *Nature,* 366:643–654; Hall, (1994). *Annu. Rev. Cell Biol.,* 10:31–54; Ridley, (1995). *Curr. Opon. Gen. Dev.,* 5:24–30; Zigmond, (1996). *Curr. Opin. Cell Biol.,* 8:66–73). When active forms of the ras-like GTP-binding proteins are injected into cells, each of the family members induces unique morphological changes that involve rearrangement of F-actin. For example, in fibroblasts cdc42 regulates actin polymerization and focal complexes necessary for filopodia formation; rac mediates actin polymerization and focal complex assembly within lamellipodia and membrane ruffles; and rho induces actin stress fiber and focal adhesion (FA) complex formation (Nishiyama et al., (1994). *Mol Cell. Biol.,* 14:2447–2456; Ridley, (1994). *BioEssays,* 16:321–327; Ridley and Hall, (1994). *EMBO J.,* 13:2600–2610; Nobes and Hall, (1995). *Cell,* 81:53–62; Nobes et al., (1995). *J. Cell Science,* 108:225–233; Ridley et al., (1995). *Mol. Cell. Biol.,* 15:1110–1122). In addition to these specific changes, rho family members share some of the same functions and there is cross-talk among members (Zigmone, supra). A hierarchical relationship exists among cdc42, rac, and rho, whereby cdc42 regulates rac activity and rac regulates rho activity, suggesting that these proteins may orchestrate the spatial and temporal changes in the actin cytoskeleton necessary for complex processes such as cell motility and cytokinesis (Ridley and Hall, (1992). *Cell,* 70:389–399; Chant and Stowers, (1995). *Cell,* 81:1–4; Nobes and Hall, (1995). *Cell,* 81:53–62; Lauffenburger and Horwitz, (1996). *Cell,* 84:359–369). Rho-like GTPases also play an essential role in cell cycle progression (Olson et al., (1995). *Science,* 269:1270–1272; Ridley, (1995). *Curr. Opin. Gen. Dev.,* 5:24–30), ras-mediated cell transformation (Khosravi-Far et al., (1995). *Mol. Cell. Biol.,* 15:6443–6453; Qiu et al., (1995). *Proc. Natl. Acad. Sci. USA,* 92:11781–11785), transcriptional regulation (Hill et al., (1995). *Cell,* 81:1159–1170), growth factor-induced arachidonic acid release and calcium influx (Peppelenbosch et al., (1995). *Cell,* 81:849–856; Peppelenbosch et al., (1996). *J Biol. Chem.,* 271:7883–7886), and possibly HIV-1 replication (Lu et al., (1996). *Curr. Biol.,* 6:1677–1684).

Rho-like GTPases function as molecular switches that are active when bound to GTP and inactive when bound to GDP (Boguski and McCormick, (1993)). *Nature,* 366:643–654). The activation state is positively regulated by guanine nucleotide exchange factors (GEFs) which promote the exchange of GDP for GTP, and negatively regulated by GTPase activating proteins (GAPs) (Boguski and McCormick, (1993). *Nature,* 366:643–654; Lamarche and Hall, (1994). TIG, 10:446–440; Overbeck et al., (1995). *Mol. Repro. Dev.,* 42:468–476; Cerione and Zheng, (1996). *Curr. Opin. Cell Biol.,* 8:216–222). In addition to GEFs and GAPs, the activation status of rho-like GTPases is controlled by GDP dissociation inhibitors and GDP dissociation stimulators (Boguski and McCormick, (1993). *Nature,* 366:643–654). About 20 GEFs for rho-like GTPases have been identified by sequence comparison (the Dbl homology (DH) GEF family), and a majority of these were shown to have GEF activity in vitro (Cerione and Zheng, (1996). *Curr. Opin. Cell Biol.,* 8:216–222). Most of the DH GEFs were originally isolated as oncogenes including Dbl (Ron et al., 1988. *EMBO J.,* 7:2465–2473; Hart et al., 1991. *Nature,* 354:311–314; Hart et al., (1994). *J. Biol. Chem.,* 269:62–65), Ost (Horii et al., (1994). *EMBO J.,* 13:4776–4786), and the invasion-inducing Tiam-1 oncogene (Habets et al., (1994). *Cell,* 77:537–549; Michiels et al., (1995). *Nature,* 375:338–340; van Leeuwen et al., (1995). *Oncogene,* 11:2215–2221). Upstream regulators of the rho/rac GEFs include growth factor receptors with protein tyrosine kinase activity (e.g., the insulin, EGF, and PDGF receptors), and seven transmembrane domain receptors coupled to heterotrimeric G proteins (e.g., the lysophosphatidic acid (LPA), bombesin, and bradykinin receptors) (Cerione and Zheng, (1996). *Curr. Opin. Cell Biol.,* 8:216–222). In addition, growth factor-mediated activation of rho/rac GEF may in some cases involve phosphatidylinositol (PI)-3 kinase (Nobes et al., (1995). *J. Cell Science,* 108:225–233; Tsakiridis et al., (1996). *J. Biol. Chem.,* 271:19664–19667).

A number of studies indicate that activated rho-like GTPases function as regulators of kinases. Rac and cdc42 were shown to activate members of the family of p21-activated serine/threonine kinases (PAKs) (Manser et al., (1994). *Nature,* 367:40–46; Bagrodia et al., (1995). *J. Biol. Chem.,* 47:27995–27998; Knaus et al., (1995). *Science,* 269:221–223; Martin et al., (1995). *E.M.B.O. J.,* 14:1970–1978; Frost et al., (1996). *Mol. Cell. Biol.,* 16:3707–3713; Jakobi et al., (1996). *J. Biol. Chem.,* 271:6206–6211). These kinases are homologous to the yeast STE20 kinase, which is involved in regulating a yeast MAP kinase cascade controlling mating pheromone response, polarity establishment, and filamentous growth of diploids (Ottilie et al., (1995). *EMBO J.,* 14:5908–5918; Simon et al., (1995). *Nature,* 376:702–705; Stevenson et al., (1995). *Genes Dev.,* 9:2949–2963). Rac and cdc42 also activate the mitogen-activated kinase (MAPK) family members Jun N-terminal kinase (JNK, also known as stress activated protein kinase (SAPK)) and p38 MAPK (Coso et al., (1995). *Cell,* 81:1137–1146.; Minden et al., (1995). *Cell,* 81:1147–1157; Pombo et al., (1995). *Nature,* 377:750–754; Vojtek and Cooper, (1995). *Cell,* 82:527–529; Zhang et al., (1995). *J. Biol. Chem.,* 270:23934–23936), in addition activating the 70 kDa S6 kinase (Chou and Blenis, (1996). *Cell,*

85:573–583). Rho activates protein kinase N (PKN) (Amano et al., (1996). *J. Biol. Chem.,* 271:20246–20249; Watanabe et al., (1996). *Science,* 271:645–648), p160$^{ROCK}$ kinase (Ishizaki et al., (1996). *EMBO J.,* 15:1885–1893), and rho-kinase (Matsui et al., (1996). *EMBO J.,* 15:2208–2216.). Rho-kinase was shown to phosphorylate the myosin light chain (MLC) (Amano et al., (1996). *J. Biol. Chem.,* 271:20246–20249) and the myosin-binding subunit (MBS) of the myosin phosphatase, which results in the inactivation of myosin phosphatase and increased MLC phosphorylation (Kimura et al., (1996). *Science,* 273:245–248). Rho-kinase phosphorylates myosin light chain (MLC) and phosphorylation, which results in contraction of smooth muscle and interaction of actin and myosin in non-muscle cells (Chrzanowska-Wodnicka and Burridge, (1996). *J. Cell Biol.,* 133:1403–1415). Rho-like GTPases have also been shown to regulate PI 4-phosphate 5-kinase (PIP 5-kinase) (Chong et al., (1994). *Cell,* 79:507–513), PI 3-kinase (Zheng et al., (1994). *J. Biol. Chem.,* 269:18727–18730; Tolias et al., (1995). *J. Biol. Chem.,* 270:17656–17659; Bokoch et al., (1996). *Biochem. J.,* 315:775–779), and phospholipase D (Malcolm et al., (1994). *J. Biol. Chem.,* 269:25951–25954; Balboa and Insel, (1995). *J. Biol. Chem.,* 270:29843–29847; Kwak et al., (1995). *J. Biol. Chem.,* 270:27093–27098). Localized increases in PIP$_2$ levels has been suggested to control actin polymerization and FA formation (Chong et al., (1994). *Cell,* 79:507–513; Hartwig et al., (1995). *Cell,* 82:643–653; Gilmore and Burridge, (1996). *Nature,* 381:531–534).

In addition to regulating kinases rho-like GTPases are involved in the regulation of other proteins, including the multicomponent NADPH oxidase (Diekmann et al., (1994). *Science,* 265:531–533; Knaus et al., (1995). Regulation of human leukocyte p21-activated kinases through G protein-coupled receptors. *Science,* 269:221–223), tubulin (Best et al., (1996). *J. Biol. Chem.,* 271:3756–3762), and POR1 which is involved in membrane ruffling (Van Aelst et al., (1996). *EMBO J.,* 15:3778–3786).

Proteins with GEF activity have also been implicated in cellular transformation. For example, several members of the Dbl family, which may function as GEFs for the rho-like proteins, have oncogenic activity (Adams et al., (1992) *Oncogene* 7:611; Miki et al (1993) *Nature* 362:462). Activated rac1 cooperates with a membrane-targeted form of raf (raf-CAAX) in oncogenic transformation (Qiu et al. (1995) *Nature* 374:457). In addition, rac and rho are essential for ras transformation of cells (Qiu, R. et al. (1995) *Nature* 374, 457–459; Khosravi-Far, R., et al. (1995) *Mol. Cell. Biol.* 15, 6443–6453). Cdc42, rho, and rac all appear to stimulate c-fos transcription (Hill, C. S., et al. (1995) *Cell* 81, 1159–1170), as well as cell cycle progression through G1 and subsequent DNA synthesis (Olson, M., et al. (1995) *Science* 269, 1270–1272). Rac is also involved in the activation of the NADPH oxidase complex in neutrophils (Segal and Abo (1993) *Trends Biochem. Sci.* 18:43).

Another protein thought to play a role in rearrangement of the actin cytoskeleton is the leukocyte common antigen related (LAR) transmembrane protein tyrosine phosphatase (PTPase). LAR is widely expressed and is comprised of a cell-adhesion-like extracellular region and two intracellular PTPase domains (Streuli, M., et al. (1992) *EMBO J.* 11, 897–907; Yu, Q., et al. (1992) *Oncogene* 7, 1051–1057; Fischer, E. H., et al. (1991) *Science* 253, 401–406; Mourey, R. J. and Dixon, J. E. (1994) *Curr. Op. Gen. Dev.* 4, 31–39). A role for LAR in regulating cell-matrix interactions was proposed, based on the colocalization of LAR with a coiled-coil protein, termed LAR interacting protein.1 (LIP.1) at the ends of FAs (Serra-Pagés, C., et al. (1995) *EMBO J.* 14, 2827–2838). In addition LAR expression has been observed at regions of association between cells and basement membrane in various tissues (Streuli, M., et al. (1992) *EMBO J.* 11, 897–907).

Thus, certain biological functions such as growth, differentiation, and migration are tightly regulated by these signal transduction pathways within cells. Disregulation of normal activation pathways removes this tight control resulting in disease states, such as transformation. The development of agents capable of modulating ras-like GTP-binding proteins is clearly desirable, given the salient role of these molecules in regulating numerous aspects of cellular activation.

SUMMARY OF THE INVENTION

The present invention is based, at least in part, on the discovery of novel molecules, referred to herein as "TRIO" nucleic acid and polypeptide molecules. The TRIO molecules of the present invention are useful as modulating agents in regulating a variety of cellular processes. TRIO is a 2,861 amino acid phosphoprotein containing two DH GEF domains each with an adjacent pleckstrin homology (PH) domain and SH3 domain, a protein serine/threonine kinase (PSK) domain with an adjacent Ig-like domain. and four spectrin-like repeats. The N-terminal TRIO GEF domain has rac 1-specific activity and the C-terminal GEF domain has rhoA-specific activity in vitro (Debant et al., (1996). *Proc. Natl. Acad. Sci., USA,* 93:5466–5471). PH domains are found adjacent to all functional Dbl-like GEF domains, as well as in numerous other signal transduction proteins, and are likely to play a role in membrane localization and/or protein-protein interactions (Musacchio et al., (1993). *TIBS,* 18:343–348; Pitcher et al., (1995). *J. Biol. Chem.,* 270:11707–11710; Cerione and Zheng, (1996). *Curr. Opin. Cell Biol.,* 8:216–222; Lemmon et al., (1996). *Cell,* 85:621–624). SH3 domains are protein-protein interaction domains found in diverse signaling proteins (Cohen et al., (1995). *Cell,* 80:237–248). Spectrin repeats are ~100 amino acid long and found in a number of proteins, including the actin binding proteins spectrin, fodrin, a-actinin, and dystrophin, but their function remains unclear (Dhermy, 1991. *Biol. Cell,* 71:249–254). The TRIO PSK domain has the highest degree of sequence similarity with calcium/calmodulin-dependent PSKs, although it is not yet known whether TRIO PSK activity requires calmodulin as TRIO kinase activity has not been established (Debant et al., (1996). *Proc. Natl. Acad. Sci., USA,* 93:5466–5471). The large size and complex structure of TRIO, with three enzymatic domains and multiple candidate protein-protein interaction domains, is unique, and suggests that TRIO is a central organizer of multiple signaling pathways. Both TRIO GEF domains are functional in vivo and that expression of these two GEF domains differentially affect the organization of the actin cytoskeleton and cell growth. Cells expressing the rac 1-specific TRIO GEF domain exhibit increased membrane ruffling and enhanced cell spreading kinetics, and exhibit anchorage-independent growth. In contrast, cells expressing the rhoA-specific GEF domain possess increased actin stress fibers and focal adhesions, and exhibit increased locomotion.

In one aspect, the invention features isolated TRIO nucleic acid molecules. In a preferred embodiment of the invention the subject TRIO nucleic acid is vertebrate. In one embodiment, the nucleic acid of the present invention is mammalian, or is capable of hybridizing to a mammalian TRIO gene or to the complement of a mammalian TRIO gene. In preferred embodiments, a TRIO nucleic acid molecule is mouse or human.

In a further embodiment, the claimed nucleic acid hybridizes with the coding sequence designated in SEQ ID No: 1 or to the complement to the coding sequence designated in SEQ ID No: 1. In a preferred embodiment, the hybridization is conducted under stringent conditions.

In a particularly preferred embodiment, an isolated TRIO nucleic acid molecule has a nucleotide sequence shown in SEQ ID NO:1 or a sequence complementary to that shown in SEQ ID NO:1.

In another embodiment of the invention, a TRIO nucleic acid comprises a nucleotide sequence homologous to the sequence shown in SEQ ID NO:1. In one embodiment, a TRIO nucleic acid sequence is at least about 60% homologous to the nucleotide sequence shown in SEQ ID NO:1 or its complement. In another embodiment, a TRIO nucleic acid sequence is at least about 70% homologous to the nucleotide sequence shown in SEQ ID NO:1 or its complement. In yet another embodiment, a TRIO nucleic acid is at least about 80% homologous to the nucleotide sequence shown in SEQ ID NO:1 or its complement. In a preferred embodiment, a TRIO nucleic acid molecule is at least 90% homologous to the nucleotide sequence shown in SEQ ID NO:1 or its complement. In yet another embodiment, a TRIO nucleic acid molecule is at least 95–98% homologous to the nucleic acid sequence shown in SEQ ID NO:1 or its complement.

In another embodiment, a nucleic acid molecule of the present invention encodes a TRIO polypeptide. In another embodiment, a TRIO nucleic acid encodes a polypeptide which comprises an amino acid sequence about 60% homologous to the polypeptide of SEQ ID NO:2. In yet another embodiment, a TRIO nucleic acid encodes a polypeptide comprising an amino acid sequence at least about 70% homologous to the sequence shown in SEQ ID NO:2. In a preferred embodiment, a TRIO nucleic acid encodes a polypeptide comprising an amino acid sequence at least about 80% homologous to the sequence of SEQ ID NO:2. In another preferred embodiment, a TRIO nucleic acid encodes a polypeptide of at least about 90% homology to the sequence of SEQ ID NO. 2. In another preferred embodiment, a TRIO nucleic acid encodes a polypeptide at least about 95–98% homologous to the polypeptide of SEQ ID NO.:2. In a particularly preferred embodiment, a TRIO nucleic acid encodes the polypeptide of SEQ ID NO. 2.

In preferred embodiments, one of the subject TRIO nucleic acid molecules of the present invention is capable of encoding a polypeptide with a TRIO bioactivity.

The disclosed molecules can be non-coding, (e.g. probe, antisense or ribozyme molecules) or can encode a functional TRIO polypeptide (e.g. a polypeptide which specifically modulates, e.g., by acting as either an agonist or antagonist, at least one bioactivity of the human TRIO polypeptide). In a preferred embodiment, a TRIO nucleic acid molecule includes the entire coding region of SEQ ID NO:1.

The invention also provides probes and primers composed of substantially purified oligonucleotides, which correspond to a region of nucleotide sequence which hybridizes to at least about 6 consecutive nucleotides of the sequence set forth in SEQ ID No: 1, the complement of SEQ ID No:1, or naturally occurring mutants thereof. In preferred embodiments, an oligonucleotide of the present invention specifically detects a TRIO nucleic acid. In preferred embodiments, the probe/primer further includes a label which is capable of being detected.

For expression, the subject TRIO nucleic acids can include a transcriptional regulatory sequence, e.g. at least one of a transcriptional promoter (for constitutive expression or inducible expression) or transcriptional enhancer sequence operatively linked to the TRIO gene sequence. Such regulatory sequences in conjunction with a TRIO nucleic acid molecules can be useful vectors for gene expression. In other embodiments, the transcriptional regulatory sequence can be operatively linked to a heterologous coding sequence.

The invention also provides expression vectors. In one embodiment, an expression vector contains a TRIO nucleic acid molecule operatively linked to a transcriptional regulatory sequence. In preferred embodiments, an expression vector of the present invention is capable of replicating in a cell.

This invention also pertains to host cells transfected with expression vectors whether prokaryotic or eukaryotic and in vitro (e.g. cell culture) and in vivo (e.g. transgenic) methods for producing TRIO proteins by employing expression vectors.

The present invention also provides for a recombinant transfection system containing a TRIO nucleic acid which is operatively linked to a transcriptional regulatory sequence which allows for transcription in eukaryotic cells and a gene delivery composition which allows for cells to be transfected with the TRIO gene.

In another aspect, the invention features isolated TRIO polypeptides, preferably substantially pure preparations e.g. of plasma purified or recombinantly produced TRIO polypeptides. In one embodiment, the polypeptide is identical to or similar to a TRIO protein represented in SEQ ID No. 2. Related members of the vertebrate and particularly the mammalian TRIO family are also within the scope of the invention. In one embodiment, the polypeptide comprises an amino acid sequence at least about 60% homologous to a TRIO protein represented in SEQ ID No. 2. In yet another embodiment, an isolated TRIO polypeptide of the present invention comprises an amino acid sequence at least about 70% homologous to the amino acid sequence shown in SEQ ID NO:2. In a preferred embodiment, a TRIO polypeptide is at least about 80% homologous to the amino acid sequence shown in SEQ ID NO:2. In a particularly preferred embodiment, a TRIO polypeptide is at least about 90% homologous to the amino acid sequence shown in SEQ ID NO:2. In another preferred embodiment a TRIO polypeptide comprises an amino acid sequence at least about 95–98% homologous to the amino acid sequence shown in SEQ ID NO:2.

In preferred embodiments, a polypeptide of the present invention has a TRIO bioactivity. In another preferred embodiment, a TRIO polypeptide has a TRIO bioactivity and contains at least one structural TRIO domain.

Fragments of a TRIO polypeptide which posses a TRIO activity are also provided for. Preferred fragments will encode one or more of a rac1 GEF domain, a rhoA GEF domain, one or more pleckstrin homology (PH) domains, a protein serine/threonine kinase (PSK) domain, an immunoglobulin-like domain, and one or more spectrin-like domains, or any combination of these domains.

The TRIO polypeptide can comprise a full length protein, such as represented in SEQ ID No. 2, or it can comprise a fragment corresponding to one or more particular motifs/domains, or to various, selected sizes, e.g., at least about 5, 10, 25, 50, 100, 150 or 200 amino acids in length. Other referred peptide fragment sizes are at least about 10 kD, preferably about 50 kD, more preferably about 100 kD, and most preferably about 200 kD. In particularly preferred embodiments, the TRIO polypeptide of the present invention is at least about 330 kD.

In one embodiment, a TRIO polypeptide is encoded by a TRIO nucleic acid as described herein. In a preferred embodiment, a TRIO poplypeptide is encoded by the nucleic acid shown in SEQ ID NO:1.

The subject TRIO proteins also include modified proteins, e.g., such as proteins modified to resist post-translational modification, as for example, due to mutations which alter modification sites (such as tyrosine, threonine, serine or aspargine residues), or which prevent glycosylation of the protein, or which prevent interaction of the protein with intracellular proteins.

Another aspect of the invention features chimeric molecules (e.g. fusion proteins) including a TRIO protein. For example, the TRIO protein can be provided as a recombinant fusion protein which includes a second polypeptide portion, e.g., a second polypeptide having an amino acid sequence unrelated (heterologous) to the TRIO polypeptide. In a preferred embodiment, a fusion protein of the present invention contains a detectable label or a matrix binding domain.

Yet another aspect of the present invention features an immunogen comprising a TRIO polypeptide in an immunogenic preparation, the immunogen being capable of eliciting an immune response specific for a TRIO polypeptide, e.g. a humoral response, an antibody response and/or cellular response.

In preferred embodiments, the immunogen comprises an antigenic determinant, e.g. a unique determinant, from the protein represented by SEQ ID No. 2.

A still further aspect of the present invention features antibodies and antibody preparations specifically reactive with an epitope of the TRIO protein. In preferred embodiments, the antibody specifically binds to an epitope represented in SEQ ID No: 2.

Yet another aspect of the present invention concerns a method for modulating the growth, differentiation, migration and/or survival of a cell by modulating TRIO bioactivity, (e.g., by potentiating or disrupting certain protein-protein interactions). In general, whether carried out in vivo, in vitro, or in situ, the method comprises treating the cell with an effective amount of a TRIO modulating agent so as to alter, relative to the cell in the absence of treatment, at least one of (i) rate of growth, (ii) differentiation, (iii) survival, or (iv) migration of the cell.

Accordingly, methods discussed herein can be carried out with TRIO modulating agents as described herein, such as, nucleic acids, peptides, and peptidomimetics, or modulating agents identified in drug screens which have a TRIO bioactivity, for example, which agonize or antagonize the effects of a TRIO protein. Other TRIO modulating agents include antisense constructs for inhibiting expression of TRIO proteins, and dominant negative mutants of TRIO proteins which competitively inhibit protein interactions of the wild-type TRIO protein.

In yet another aspect, the invention provides assays, e.g., for screening tests to identify modulating agents which modulate TRIO. For example, modulating agents which are inhibitors, or alternatively, potentiators of an interaction between a TRIO protein and, for example, an intracellular protein which binds to the TRIO protein. An exemplary method includes the steps of (i) combining a TRIO polypeptide or bioactive fragments thereof, a TRIO target molecule, and a test modulating agent, e.g., under conditions where, but for the test modulating agent, the TRIO protein and target molecule are able to interact; and (ii) detecting the formation of a complex which includes the TRIO protein and the target polypeptide either by directly quantitating the complex, or by measuring a bioactivity of the TRIO protein. A statistically significant change, such as a decrease, in the interaction of the TRIO- and target molecule in the presence of a test modulating agent (relative to what is detected in the absence of the test modulating agent) is indicative of a modulation (e.g., inhibition or potentiation of the interaction between the TRIO protein and the target molecule).

A further aspect of the present invention provides a method of determining if a subject is at risk for a disorder characterized by, e.g., unwanted cell proliferation or migration. The subject method involves detecting at least one of (i) aberrant modification or mutation of a gene encoding a TRIO protein, (ii) mis-regulation, and (iii) aberrant post-translational modification of a TRIO gene. In one embodiment, detecting the genetic lesion includes ascertaining the existence of at least one of: a deletion of one or more nucleotides from a TRIO gene; an addition of one or more nucleotides to the gene; a substitution of one or more nucleotides of the gene; a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of TRIO protein. In a preferred embodiment, a TRIO probe of the present invention is combined with the nucleic acid of a cell and hybridization of the probe to the nucleic acid is determined. Failure of the probe to hybridize or a reduction of hybridization signal are indicative of a mutation to a TRIO gene.

The invention also features transgenic non-human animals which include a heterologous form of a TRIO gene or antisense form of a TRIO gene, so that expression of TRIO is enhanced or induced, or which misexpress an endogenous TRIO gene (e.g., an animal in which expression of one or more of the subject TRIO proteins is disrupted, prevented or suppressed).

Other features and advantages of the invention will be apparent from the following detailed description and claims.

BRIEF DESCRIPTION OF THE DRAWINGS

FIGS. 2A–2B show the biochemical characterization of TRIO. Panel A shows SDS-PAGE analysis of a-TRIO.56, a-TRIO.68 mAb, and isotype matched control mAb immunoprecipitated protein from [$^{35}$S]methionine labeled human breast adenocarcinoma MCF7 cell lysates. Molecular mass standards in kilodaltons (kDa) are shown at the left of the figure. The position of the >250 kDa TRIO protein is indicated by an asterisk (*). Panel B shows SDS-PAGE analysis of a-TRIO.68 mAb and isotype-matched control mAb immunoprecipitated protein from [$^{32}$P]

orthophosphate-labeled HeLa cell lysates. On the bottom of the figure is shown the phosphoamino acid analysis of the $^{32}$P-labeled protein immunoprecipitated by the a-TRIO.68 mAb from medium-treated cells. The positions of the control, non-radiolabeled phosphorylated aa phosphoserine (P-Ser), phosphothreonine (P-Thr) and phosphotyrosine (P-Tyr) are indicated by ovals.

Figure 3:
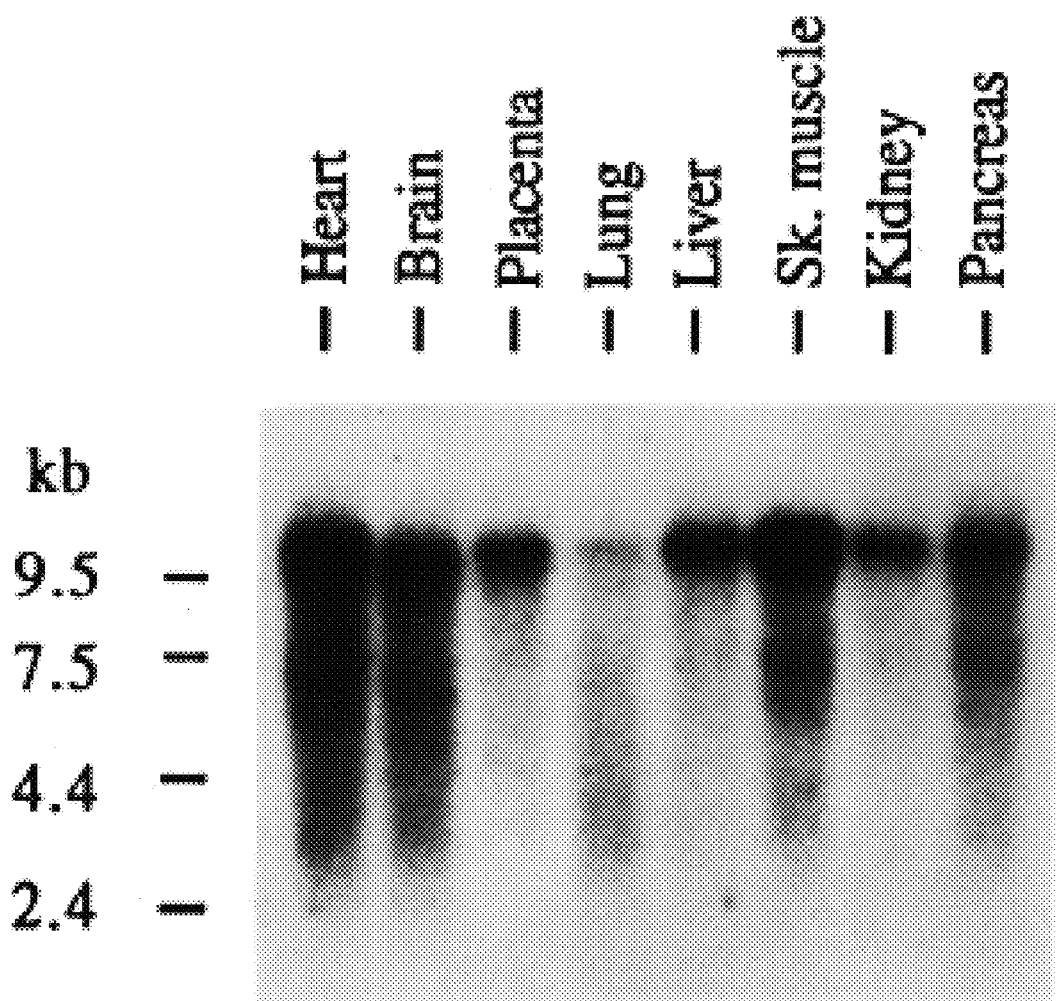
Figure 4G:
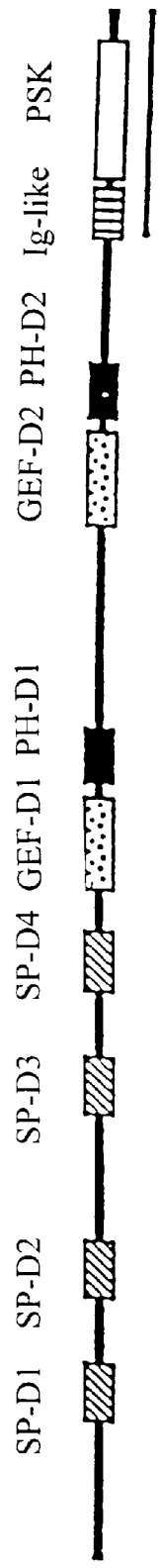

FIG. 3 shows TRIO mRNA expression by Northern blot analysis of 2 mg of poly(A)+ RNA isolated from the human tissues indicated at the top of the figure using a radiolabeled TRIO cDNA probe. Size markers in kilobases (kb) are shown at the left of the figure.

FIGS. 4A–4G show the multiple domains of TRIO. Panel A shows the TRIO 2,861 aa sequence deduced from cDNA cloning is shown using the standard one letter aa code. Numbers at the right indicate amino acid residues. Shown in panel B, the two TRIO GEF domains (TRIO GEF-D1 and -D2) are aligned with the dbl GEF and ost GEF domain sequences. Consensus invariant amino acids are in upper case and consensus amino acids present in dbl and ost and one of the two TRIO GEF sequences are in lower case. Numbers indicate amino acid residues used for the alignment. In panel C the TRIO PSK domain sequence is aligned with the kinase domains of DAP PSK and Dictyostelium MLCK. Consensus invariant amino acids are in upper case. Panel D shows the overall structure of TRIO is schematically shown with the relative length and positions of the four TRIO spectrin (SP)-like domains, two GEF domains, two pleckstrin homology (PH) domains, Ig-like domain, and the PSK domain. The horizontal line below the TRIO schematic indicates the relative length and position of the Cl.1G0 peptide.

FIGS. 5A–5D illustrates that TRIO GEF domains have distinct substrate specificity for rac and rho in vitro. At the top of the figure (panel A) is schematically shown the region of TRIO containing the two GEF domains, and below are shown the extent of the TRIO deletion mutants, TRIOD2 (GEF-D1) and TRIOD3 (GEF-D2). Panel B shows the activity of COS cell lysates containing TRIOD2 (solid bars) or TRIOD3 (striped bars) to catalyze the release of [$^3$H]GDP from rac1, rhoA, cdc42, or ras. The activity is expressed as the percent [$^3$H]GDP released from each GTP binding protein after 20 min. Kinetics of rac1 (panel C) and rhoA (panel D) GEF activity present in COS lysates containing TRIOD2 (closed circles), TRIOD3 (open circles), or vector-only control (open squares). The activity is presented as the relative amount of bound [$^3$H]GDP remaining at various time points to the amount bound at time 0.

Figure 6:
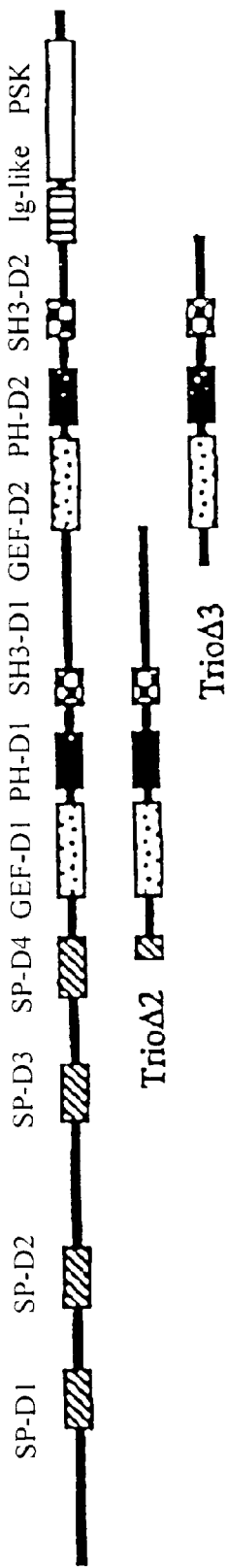

FIG. 6 shows the extent of the deletions in mutants TRIO-rac GEF and TRIO-rho GEF. TRIO is a multidomain protein. The structure of TRIO is schematically shown. SP-D, spectrin-like domain; GEF-D, guanine nucleotide exchange factor domain; PH-D, pleckstrin homology domain; SH3-D, src-homology 3 domain; Ig, immunoglobulin; PSK, protein serine/threonine kinase.

FIGS. 7A–7L Expression of TRIO-racGEF and TRIO-rhoGEF enhances NIH 3T3 cell spreading. Shown are phase-contrast microphotographs of NIH 3T3:control cells (panels A–D), NIH 3T3:TTRIO-racGEF cells (E–H), and NIH 3T3:TRIO-rhoGEF (I–L) 70 min (A, E, and I), 140 min (B, F, and J), 200 min (C, G, and K), and 270 min (D, H, and L) after plating cells onto tissue culture dishes in media containing 10% FCS. By 70 min>90% of all three cell types had adhered to the dishes as determined by number of the cells remaining in suspension compared to the cells attached to the plates.

FIGS. 8A–8C. Expression of TRIO-racGEF and TRIO-rhoGEF alters cell morphology. Shown are triple exposure immunofluorescence photographs of the (A) NIH 3T3:control (vector only) cells, (B) NIH 3T3:TRIO-racGEF cells, and (C) NIH 3T3:TRIO-rhoGEF cells. Cells were stained for actin (green), P-Tyr (red), and DNA (blue) as described in Materials and Methods. Cells were grown in media containing 10% FCS. Bar represents 20 mm.

FIGS. 9A–9L. Expression of TRIO-rhoGEF enhances cell locomotion. Shown are photographs of NIH 3T3:control cells (panels A–D), NIH 3T3:TRIO-racGEF cells (E–H), and NIH 3T3:TRIO-rhoGEF cells (I–L), 0 h (A, E, and I), 6.5 h (B, F, and J), 12 h (C, G, and K), and 23 h (D, H, and L) after the cell monolayers were wounded. Arrows and dots indicate the origin of the wound at time 0 h.

FIGS. 10A–10I. TRIO-racGEF expression affects NIH 3T3 cell morphology in a temperature-dependent manner. Panels A–C, NIH 3T3:control cells; D–F, NIH 3T3:TRIO-racGEF cells; and G–I, NIH 3T3:TRIO-rhoGEF cells are shown just prior to cooling (A, D, and G), after 30 min at room temperature (~21° C.) (B, E, and H), and 13.5 h (C, F, and I) after being returned to 37° C. following cooling to room temperature.

DETAILED DESCRIPTION OF THE INVENTION

The rho family of GTPases, including rho, rac, and cdc42, are molecular switches that regulate diverse cellular processes, including growth control and reorganization of the actin cytoskeleton in response to extracellular signals. These GTPases are positively regulated by guanine nucleotide exchange factors (GEFs) and are inactivated by GTPase activating proteins. The multidomain TRIO protein contains two GEF domains, the N-terminal of which has rac 1-specific GEF activity, while the C-terminal TRIO GEF domain has rhoA-specific GEF activity in vitro.

Exemplary TRIO domains include the rac 1 GEF comprising amino acids 1237–1407 of SEQ ID NO:2; the rho A GEF comprising amino acids 1914–2085 of SEQ ID NO:2; the pleckstrin homology domains comprising amino acids 1435–1534 and 2113–2214; the serine/threonine kinase domain comprising amino acids 2560–2816 of SEQ ID NO:2; and the Ig-like domain comprising amino acids 2448–2541 of SEQ ID NO:2.

Like the critical GEF domains, the other TRIO domains likely play a role in the function of the TRIO protein or TRIO equivalents. PH domains are found adjacent to all functional rho/rac GEF domains, as well as in a number of other signal transduction proteins, and are expected to play a role in protein-protein interactions and/or membrane localization (Musacchio, A., et al. (1993) TIBS 18, 343–348, Pitcher, J. A., et al. (1995) *J. Biol. Chem.* 270, 11707–11710). Preferred TRIO PH domains are represented by amino acids 1435–1534 and 2113–2214 of SEQ ID No:2.

At the TRIO C-terminal end there is a PSK domain, indicating a kinase activity for TRIO (Hanks, S. K. and Quinn, A. M. (1991) *Meth. Enzymol.* 200, 38–62). Of the 15 invariant or nearly invariant amino acids present in PSKs (Hanks and Quinn supra), all are conserved in TRIO (FIG. 4C). The PSK domain is most similar to calcium/calmodulin-dependent kinases, which similarly contain associated Ig-like domains, suggesting that calmodulin may play a role in the activation of TRIO. A preferred TRIO kinase domain is represented by amino acids 2560–2816 of SEQ ID No: 2.

Adjacent to the kinase domain there is an Ig-like domain. The Ig-like domain may also play a role in protein-protein interactions. Other intracellular proteins, including smooth muscle MLCK (Olson, N. J., et al. (1990) Proc. Natl. Acad. Sci. USA 87, 2284–2288) and the C. elegans twitchin kinase (Benian, G. M., et al. (1989) Nature 342, 45–50), also contain Ig-like domains. A preferred TRIO Ig-like domain is represented by amino acids 2448–2541 of SEQ ID No: 2.

Spectrin repeats are approximately 106 amino acids in length and found in a number of proteins, including the actin binding proteins spectrin, fodrin, a-actinin, and dystrophin (Dhermy, D. (1991) Biol. Cell 71, 249–254). These domains may be involved in connecting functional domains and/or mediate protein-protein interactions, and may direct the targeting of TRIO to the cytoskeleton and/or plasma membrane. Preferred TRIO spectrin domains are represented by amino acids 252–359, 479–585, 819–925, and 1050–1157 of SEQ ID NO: 2.

In one embodiment, the TRIO protein of the present invention binds to a transmembrane PTPase. In a preferred embodiment, the TRIO polypeptide binds to LAR, preferably to the LAR PTPase domain. TRIO may function to allosterically regulate the phosphatase activity of LAR and/or serve as a substrate for LAR phosphatase activity.

In preferred embodiments, the TRIO polypeptide of the present invention migrates with an apparent molecular weight of 300–350 kd by SDS PAGE analysis. In a particularly preferred embodiment TRIO has an apparent molecular weight of 330 kD. In another preferred embodiment, TRIO is post-translationally modified. For example, a phosphorylated form of the protein has been detected; TRIO appears to be phosphorylated only on serine residues. Other modifications of TRIO may be in the form of, for example, phosphorylation, ubiquitinylation, acylation, prenylation, or the like. Post-translational modification of the TRIOs may result in the localization observed, and may also contribute to protein-protein interactions, or in changes to an intrinsic enzymatic activity of the TRIO, or in changes to the stability of the protein (e.g., its half-life). It will be understood that certain post-translational modifications, e.g., phosphorylation and the like, can increase the apparent molecular weight of the TRIO protein relative to the unmodified polypeptide chain. Expression of individual TRIO GEF domains in NIH 3T3 cells differentially affects cell morphology, cell motility, and cell growth. Cells expressing the rac-specific TRIO GEF domain exhibit pronounced membrane ruffles and faster cell spreading kinetics, whereas cells expressing the TRIO rho-specific GEF domain display more actin stress fibers and focal adhesion complexes. Moreover, cells expressing the TRIO rho-specific GEF domain exhibit increased locomotive motility. Expression of the TRIO rac-specific GEF domain, but not the rho-specific domain, confers anchorage-independent growth, suggesting that TRIO is potential protooncogene.

The large size and complex structure of TRIO, with three enzymatic domains and multiple candidate protein-protein interaction domains, is unique, and suggests that TRIO is a central organizer of multiple signaling pathways, as well as actin remodeling and cell growth.

This invention pertains to a novel molecule, TRIO, which participates a variety of cellular processes. TRIO nucleic acid and protein molecules are useful as modulating agents to affect growth, differentiation, migration, and survival in a cell.

I. Nucleic Acids

As described below, one aspect of the invention pertains to isolated TRIO nucleic acids and/or equivalents of such nucleic acids. The term "equivalent" is understood to include nucleotide sequences encoding functionally equivalent TRIO polypeptides or functionally equivalent peptides having an activity of a vertebrate TRIO protein such as described herein. Equivalent nucleotide sequences will include sequences that differ by one or more nucleotide substitutions, additions or deletions, such as allelic variants; and will, therefore, include sequences that differ from the nucleotide sequence of the TRIO gene shown in SEQ ID No:1 due to the degeneracy of the genetic code.

One embodiment of the present invention features an isolated TRIO nucleic acid molecule. In a preferred embodiment, the TRIO nucleic acid molecule of the present invention is isolated from a vertebrate organism. More preferred TRIO nucleic acids are mammalian. Particularly preferred TRIO nucleic acids are human or mouse in origin.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject mammalian TRIO polypeptides preferably includes no more than 10 kilobases (kb) of nucleic acid sequence which naturally immediately flanks the mammalian TRIO gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments alone, without associating with other components and which are not naturally occurring as fragments and would not be found in the natural state. The term "isolated" is also used herein to refer to polypeptides which are isolated from other cellular proteins and is meant to encompass both purified and recombinant polypeptides.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

A particularly preferred TRIO nucleic acid is shown in SEQ ID NO:1. The term TRIO nucleic acid is also meant to include nucleotide sequences which are homologous to the sequence shown in SEQ ID NO:1 or a sequence which is complementary to that shown in SEQ ID NO:1.

"Complementary" sequences as used herein refer to sequences which have sufficient complementarity to be able to hybridize to a nucleotide sequence of the invention, forming a stable duplex.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same or a similar base or amino acid, then the molecules are homologous, similar, or identical at that position. Thus, the degree of homology between sequences is a function of the number of matching or homologous positions shared by the sequences. An "unrelated" or "non-homologous" sequence shares less than 40% identity, though preferably less than 25% identity, with one of the mammalian TRIO sequences of the present invention.

Thus, nucleic acids having a sequence that differs from the nucleotide sequences shown in SEQ ID No:1 due to degeneracy in the genetic code are also within the scope of the invention. Such nucleic acids encode functionally equivalent peptides (i.e., a peptide having a bioactivity of a mammalian TRIO polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a mammalian TRIO polypeptide. However, it is expected that DNA sequence polymorphisms that do lead to changes in the amino acid sequences of the subject TRIO polypeptides will exist among mammals. One skilled in the art will appreciate that these variations in one or more nucleotides (e.g., up to about 3–5% of the nucleotides) of the nucleic acids encoding polypeptides having an activity of a mammalian TRIO polypeptide may exist among individuals of a given species due to natural allelic variation.

In one embodiment, a TRIO nucleic acid comprises a nucleotide sequence at least about 60% homologous to the nucleotide sequence shown in SEQ ID NO:1 or its complement. In a preferred embodiment, a TRIO nucleic acid comprises a nucleotide sequence at least about 70% homologous to the nucleic acid sequence shown in SEQ. ID. NO. 1. In other embodiments, a TRIO nucleic acid comprises a nucleotide sequence at least about 80% homologous to the nucleic acid sequence shown in SEQ ID NO:1. In a preferred embodiment, a TRIO nucleic acid comprises a nucleotide sequence at least about 90% homologous to the nucleic acid sequence shown in SEQ ID NO: 1. In another preferred embodiment, a TRIO nucleic acid comprises a nucleotide sequence at least about 95–98% homologous to the nucleic acid sequence shown in SEQ ID NO: 1. In particularly preferred embodiments a TRIO nucleic acid sequence is identical to the nucleotide sequence of SEQ ID No: 1.

In preferred embodiments, a TRIO nucleic acid molecule comprises a coding sequence encoding one or more TRIO domains.

For example, in preferred embodiments a TRIO nucleic acid comprises nucleotides 3775–4287 of SEQ ID NO:1. In another embodiment a TRIO nucleic acid molecule comprises nucleotides 4372–4668 of SEQ ID NO:1.In yet another embodiment a TRIO nucleic acid molecule comprises nucleotides 5806–6321 of SEQ ID NO:1. In a further embodiment a TRIO nucleic acid comprises all or a portion of nucleotides 6403–6708 of SEQ ID NO:1. In yet another embodiment a TRIO nucleic acid fragment comprises all or a portion of nucleotides 7408–7689 of SEQ ID NO:1. In yet another embodiment a TRIO nucleic acid fragment comprises all or a portion of nucleotides 7744–8514 of SEQ ID NO:1.

In other embodiments a TRIO nucleic acid comprises a portion of a nucleotide sequence which encodes a TRIO domain. For example, in certain embodiments a TRIO nuceic acid comprises all or a portion of nucleotides 7990–8514 of SEQ ID NO:1. In another embodiment a TRIO nucleic acid molecule comprises nucleotides 3775–3954 of SEQ ID NO:1. In yet another embodiment a TRIO nucleic acid molecule comprises nucleotides 4284–4287 of SEQ ID NO:1. In a further embodiment a TRIO nucleic acid comprises all or a portion of nucleotides 4372–4549 of SEQ ID NO:1. In yet another embodiment a TRIO nucleic acid fragment comprises all or a portion of nucleotides 6403–6708 of SEQ ID NO:1.

The terms protein, polypeptide, and peptide are used interchangably herein. As used herein, proteins which have a "bioactivity" or "biological activity" of a TRIO protein include those proteins which are capable of mimicing at least one or more of the biological/biochemical activities of a naturally occurring TRIO protein. Exemplary TRIO bioactivities include the ability to activate rac and/or rho GTPases. In preferred embodiments a TRIO polypeptide can mediate actin remodeling in a cell. As such TRIO molecules can influence focal contact formation and can modulate the ability of a cell to migrate, e.g., form metastases. Other TRIO bioactivities include phosphorylation of substrates on serine and/or threonine residues. In preferred embodiments the kinase activity of the subject TRIO molecules is regulated by calmodulin. Other bioactivities of TRIO include the ability to alter the transcriptional rate of a gene such as by enzymatically regulating other cellular proteins, e.g. as a GEF or a protein kinase. For example, in preferred embodiments a TRIO molecule is capable of modulating the transcription of cfos. In other embodiments, the subject TRIO polypeptides are capable of influencing cellular transformation. Other TRIO bioactivities will be apparent to the skilled artisan based on TRIO domains and the cellular pathways in which TRIO has been shown to function.

In addition, a polypeptide has bioactivity if it is a specific agonist or antagonist (competitor) of a naturally-occurring form of a mammalian TRIO protein. In one embodiment a TRIO protein of the present invention has a TRIO bioactivity if it is capable of modulating migration in a cell. Other bioactivities of the subject TRIO proteins are described herein or will be reasonably apparent to those skilled in the art.

A TRIO nucleic acid molecucle can include an open reading frame encoding one of the mammalian TRIO polypeptides of the present invention, including both exon and (optionally) intron sequences. A "recombinant gene" refers to a nucleic acid encoding a mammalian TRIO polypeptide and comprising mammalian TRIO-encoding exon sequences, although it may optionally include intron sequences which are either derived from a chromosomal mammalian TRIO gene or from an unrelated chromosomal gene. Exemplary recombinant genes encoding the subject mammalian TRIO polypeptides are represented in the appended Sequence Listing. The term "intron" refers to a DNA sequence present in a given mammalian TRIO gene which is not spliced into mature mRNA or translated into protein and is generally found between exons.

In certain embodiments, the subject TRIO nucleic acid molecules include the 5' and 3' untranslated sequences which flank the gene, i.e., noncoding sequences, which do not encode amino acids of a TRIO polypeptide. In a preferred embodiment, a TRIO nucleic acid molecule contains the coding region of SEQ ID NO:1.

Transcriptional regulatory sequences can control tissue specific expression of genes. "Transcriptional regulatory sequence" is a term used throughout the specification to refer to DNA sequences, such as initiation signals, enhancers, and promoters, which induce or control transcription of protein coding sequences with which they are operatively linked. In preferred embodiments, transcription of one of the recombinant mammalian TRIO genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of TRIO proteins.

Another aspect of the invention provides a nucleic acid which hybridizes under stringent conditions to a nucleic acid represented by SEQ ID No:1 or its complement. Appropriate stringency conditions which promote DNA hybridization, for example, 50% formamide in 6.0×sodium chloride/sodium citrate (SSC) at about 42° C., followed by a wash of 1% SDS in 2.0×SSC at 50° C. and 65° C., are known to those skilled in the art or can be found in Current Protocols in Molecular Biology, John Wiley & Sons, New York (1989), 6.3.1–6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a particularly preferred embodiment, a TRIO nucleic acid of the present invention will hybridize to SEQ ID No: 1 under stringent conditions.

As used herein, the term "specifically hybridizes" or "specifically detects" refers to the ability of a nucleic acid molecule of the invention to hybridize to at least approximately 6, 12, 20, 30, 50, 100, 150, 200, or 300 consecutive nucleotides of a vertebrate, preferably mammalian, TRIO gene, such as a TRIO sequence designated in SEQ ID No:1, or a sequence complementary thereto, or naturally occurring mutants thereof, such that it shows more than 10 times more hybridization, preferably more than 100 times more hybridization, and even more preferably more than 100 times more hybridization than it does to to a cellular nucleic acid (e.g., mRNA or genomic DNA) encoding a protein other than a vertebrate, preferably mammalian, TRIO protein as defined herein. In a particularly preferred embodiment a TRIO nucleic acid fragment specifically detects a TRIO nucleic acid.

In a further embodiment a TRIO nucleic acid sequence encodes a vertebrate TRIO polypeptide. In a preferred embodiment the TRIO nucleic acid encodes a mammalian TRIO polypeptide. In other preferred embodiments a TRIO nucleic acid encodes a human or mouse TRIO polypeptide.

Preferred nucleic acids of the present invention encode a TRIO polypeptide which includes a polypeptide sequence corresponding to all or a portion of amino acid residues of SEQ ID No:2, e.g., at least about 2, 5, 10, 25, 50, 100, 150 or 200 amino acid residues of that region. Genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "nucleic acid sequence encoding a vertebrate TRIO polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same bioactivity.

In one embodiment, a TRIO nucleic acid encodes a polypeptide sequence comprising an amino acid sequence at least about 60% homologous to the amino acid sequence shown in SEQ ID NO: 2. In a preferred embodiment, a TRIO nucleic acid encodes a polypeptide comprising an amino acid sequence at least about 70% homologous to the sequence shown in SEQ ID NO: 2. In a preferred embodiment, a TRIO nucleic acid encodes a polypeptide comprising an amino acid sequence at least about 80% homologous to the sequence shown in SEQ ID NO: 2. In another preferred embodiment, a TRIO nucleic acid encodes a sequence at least about 90% homologous to the sequence shown in SEQ ID NO: 2. In another preferred embodiment, a TRIO nucleic acid encodes a polypeptide comprising an amino acid sequence at least about 95–98% homologous to the sequence shown in SEQ ID NO: 2. In a particularly preferred embodiment, the subject TRIO nucleic acid molecule encodes the polypeptide comprising the amino acid sequence shown in SEQ ID NO. 2.

In preferred embodiments a TRIO nucleic acid encodes a polypeptide comprising one or more TRIO domain.

The subject TRIO nucleic acid molecules allow for the generation of nucleic acid fragments (e.g., probes and primers) designed for use in identifying and/or cloning TRIO homologs in other cell types, e.g. from other tissues, as well as TRIO homologs from other mammalian organisms. For instance, the present invention also provides a nucleic acid fragment that can be used as a primer. The fragment can comprise a substantially purified oligonucleotide containing a region of nucleotide sequence that hybridizes under stringent conditions to at least approximately 12, preferably 25, more preferably 40, 50 or 75 consecutive nucleotides of sense or anti-sense sequence of SEQ ID No:1, or naturally occurring mutants thereof. For instance, primers based on the nucleic acid represented in SEQ ID No:1 can be used in PCR reactions to clone TRIO homologs from other mammalian organisms.

In another embodiment a TRIO nucleic acid fragment is an oligonucleotide probe which specifically detects a TRIO nucleic acid.

In preferred embodiments, the probe further contains a label group and can be detected, e.g. the label group can be a radioisotope, fluorescent compound, enzyme, biotin, or enzyme co-factor. Probes based on the subject TRIO sequences can also be used to detect transcripts or genomic sequences encoding the same or homologous proteins.

As discussed in more detail below, the probes of the present invention can also be used as a part of a diagnostic test kit for identifying cells or tissue which misexpress a TRIO protein, such as by measuring a level of a TRIO-encoding nucleic acid in a sample of cells from a patient; e.g. detecting TRIO mRNA levels or determining whether a genomic TRIO gene has been mutated or deleted. Briefly, nucleotide probes can be generated from the subject TRIO genes which facilitate histological screening of intact tissue and tissue samples for the presence (or absence) of TRIO-encoding transcripts. Similar to the diagnostic uses of anti-TRIO antibodies (described in detail below), the use of probes directed to TRIO messages, or to genomic TRIO sequences, can be used for both predictive and therapeutic evaluation of allelic mutations which might be manifest in certain disorders. Used in conjunction with immunoassays as described herein, the oligonucleotide probes can help facilitate the determination of the molecular basis for a disorder which may involve some abnormality associated with expression (or lack thereof) of a TRIO protein. For instance, variation in polypeptide synthesis can be differentiated from a mutation in a coding sequence.

Another aspect of the invention relates to the use of isolated TRIO nucleic acids in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject TRIO proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

Antisense Constructs

An antisense construct of the present invention can be delivered, for example, as an expression plasmid which, when transcribed in the cell, produces RNA which is complementary to at least a unique portion of the cellular mRNA which encodes a mammalian TRIO protein. Alternatively, the antisense construct is an oligonucleotide probe which is generated ex vivo and which, when introduced into the cell causes inhibition of expression by hybridizing with the mRNA and/or genomic sequences of a mammalian TRIO gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668.

Antisense approaches involve the design of oligonucleotides (either DNA or RNA) that are complementary to TRIO mRNA. The antisense oligonucleotides will bind to the TRIO mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. (1994). Nature 372:333). Therefore, oligonucleotides complementary to either the 5' or 3' untranslated, non-coding regions of a TRIO gene can be used in an antisense approach to inhibit translation of endogenous TRIO mRNA. Oligonucleotides complementary to the 5' untranslated region of the mRNA should include the complement of the AUG start codon. Antisense oligonucleotides complementary to mRNA coding regions are less efficient inhibitors of translation but can be used in accordance with the invention. Whether designed to hybridize to the 5', 3' or coding region of TRIO mRNA, antisense nucleic acids should be at least about six nucleotides in length, and are preferably oligonucleotides ranging from 6 to about 50 nucleotides in length. In certain embodiments, the oligonucleotide is at least about 10 nucleotides, at least about 17 nucleotides, at least about 25 nucleotides, or at least about 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Results obtained using the antisense oligonucleotide can be compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as: peptides (e.g., for targeting host cell receptors in vivo); or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988); or the blood-brain barrier (see, e.g., PCT Publication No. WO89/10134, published Apr. 25, 1988); hybridization-triggered cleavage agents; (See, e.g., Krol et al., 1988, BioTechniques 6:958–976); and/or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

While antisense nucleotides complementary to the TRIO coding region sequence can be used, those complementary to the transcribed untranslated region are most preferred.

The antisense molecules can be delivered to cells which express the TRIO in vivo or in vitro. A number of methods have been developed for delivering antisense DNA or RNA to cells; e.g., antisense molecules can be injected directly into the tissue site, or modified antisense molecules designed to target the desired cells (e.g., antisense linked to peptides or antibodies that specifically bind receptors or antigens expressed on the target cell surface) can be administered systematically.

A preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous TRIO transcripts and thereby prevent translation of the TRIO mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, yeast artificial chromosome, YAC, or viral vector can be used to prepare the recombinant DNA construct which can be introduced directly into the tissue site; e.g., the choroid plexus or hypothalamus. Alternatively, viral vectors can be used which selectively infect the desired tissue (e.g., for brain, herpesvirus vectors may be used), in which case administration may be accomplished by another route (e.g., systemically).

Ribozyme molecules designed to catalytically cleave TRIO mRNA transcripts can also be used to prevent translation of TRIO mRNA and expression of TRIO. (See, e.g., PCT International Publication WO90/11364, published Oct. 4, 1990; Sarver et al., 1990, Science 247:1222–1225). While ribozymes that cleave mRNA at site specific recognition sequences can be used to destroy TRIO mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are numerous potential hammerhead ribozyme cleavage sites within the nucleotide sequence of TRIO cDNA. Preferably, the ribozyme is engineered so that the cleavage recognition site is located near the 5' end of the TRIO specific mRNA; i.e., to increase efficiency and minimize the intracellular accumulation of non-functional mRNA transcripts.

Ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in TRIO mRNA.

As in the antisense approach, the ribozymes can be composed of modified oligonucleotides (e.g. for improved stability, targeting, etc.) and should be delivered to cells which express the TRIO in vivo e.g., T cells. A preferred method of delivery involves using a DNA construct "encoding" the ribozyme under the control of a strong constitutive promoter such as the pol III or pol II promoter, so that transfected cells will produce sufficient quantities of the ribozyme to destroy endogenous TRIO and inhibit transla-tion. Because ribozymes unlike antisense molecules, are catalytic, a lower intracellular concentration is required for efficiency.

Endogenous TRIO gene expression can also be reduced by inactivating or "knocking out" the TRIO gene or its promoter using targeted homologous recombination. (e.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional TRIO (or a completely unrelated DNA sequence) flanked by DNA homologous to the endogenous TRIO gene (either the coding regions or regulatory regions of the TRIO gene) can be used, with or without a selectable marker and/or a negative selectable marker, to transfect cells that express TRIO in vivo. Insertion of the DNA construct, via targeted homologous recombination, results in inactivation of the TRIO gene. Such approaches are particularly suited in the generation of animal offspring with an inactive TRIO (e.g., see Thomas & Capecchi 1987 and Thompson 1989, supra). However this approach can be adapted for use in humans provided appropriate delivery means are used.

Alternatively, endogenous TRIO gene expression can be reduced by targeting deoxyribonucleotide sequences complementary to the regulatory region of the TRIO gene (i.e., the TRIO promoter and/or enhancers) to form triple helical structures that prevent transcription of the TRIO gene in target cells in the body. (See generally, Helene, C. 1991, Anticancer Drug Des., 6(6):569–84; Helene, C., et al., (1992), Ann, N.Y. Accad. Sci., 660:27–36; and Maher, L. J., (1992), Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Sources of Nucleic Acids

TRIO nucleic acids can be obtained from mRNA present in any of a number of eukaryotic cells. It should also be possible to obtain nucleic acids encoding mammalian TRIO polypeptides of the present invention from genomic DNA from both adults and embryos. For example, a gene encoding a TRIO protein can be cloned from either a cDNA or a genomic library in accordance with protocols described herein, as well as those generally known to persons skilled in the art. Examples of tissues and/or libraries suitable for isolation of the subject nucleic acids include T cells, among others. A cDNA encoding a TRIO protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a mammalian TRIO protein can also be cloned using established polymerase chain reaction techniques in accordance with the nucleotide sequence information provided by the invention. The nucleic acid of the invention can be DNA or RNA. A preferred nucleic acid is a cDNA represented by a sequence shown in SEQ ID No:1.

Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Any of the subject nucleic acids can also be obtained by chemical synthesis. For example, nucleic acids of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448–7451), etc. Other techniques for chemically synthesizing oligodeoxyribonucleotides and oligoribonucleotides well known in the art such as for example solid phase phosphoramidite chemical synthesis.

Modifications to Nucleic Acids

Modifications to nucleic acid molecules of the invention can be introduced as a means of increasing intracellular stability and half-life. Modifications include but are not limited to the addition of flanking sequences of ribonucleotides or deoxyribonucleotides to the 5' and/or 3' ends of the molecule or the use of phosphorothioate or 2'O-methyl rather than phosphodiesterase linkages within the oligodeoxyribonucleotide backbone.

The subject nucleic acids may also contain modified bases. For example, a nucleic acid may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine,7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

A modified nucleic acid of the present invention may also include at least one modified sugar moiety selected from the group including but not limited to arabinose, 2-fluoroarabinose, xylulose, and hexose.

In yet another embodiment, the subject nucleic acid may include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Expression Vectors and Host Cells

The present invention also provides for vectors containing the subject nucleic acid molecules. As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions.

This invention also provides expression vectors containing a nucleic acid encoding a TRIO polypeptide, operatively linked to at least one transcriptional regulatory sequence. "Operatively linked" is intended to mean that the nucleotide sequence is linked to a regulatory sequence in a manner which allows expression of the nucleotide sequence. Transcriptional regulatory sequences are art-recognized and are selected to direct expression of the subject mammalian TRIO proteins. Exemplary regulatory sequences are described in Goeddel; Gene Expression Technology: Methods in Enzymology 185, Academic Press, San Diego, Calif. (1990).

In a preferred embodiment the expression vector of the present invention is capable of replicating in a cell. In one embodiment, the expression vector includes a recombinant gene encoding a peptide having TRIO bioactivity. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject mammalian TRIO proteins. Thus, another aspect of the invention features expression vectors for in vivo or in vitro transfection and expression of a mammalian TRIO polypeptide in particular cell types so as to reconstitute the function of, or alternatively, abrogate the function of TRIO in a tissue. This could be desirable when treating a disorder, for example, resulting from the misexpression of TRIO in a tissue.

In addition to viral transfer methods, such as those described above, non-viral methods can also be employed to cause expression of a subject TRIO polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject TRIO polypeptide gene by the targeted cell. Exemplary targeting means of this type include liposomal derived systems, poly-lysine conjugates, and artificial viral envelopes.

The recombinant TRIO genes can be produced by ligating nucleic acid encoding a TRIO protein, or a portion thereof, into a vector suitable for expression in either prokaryotic cells, eukaryotic cells, or both. Expression vectors for production of recombinant forms of the subject TRIO polypeptides include plasmids and other vectors. For instance, suitable vectors for the expression of a TRIO polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, a TRIO polypeptide is produced recombinantly utilizing an expression vector generated by sub-cloning the coding sequence of one of the TRIO genes represented in SEQ ID No:1.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant TRIO polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In some cases it will be desirable to express only a portion of a TRIO protein. The subject vectors can also include fragments of a TRIO nucleic acid encoding a fragment of a TRIO protein.

The subject vectors can be used to transfect a host cell in order to express a recombinant form of the subject TRIO polypeptides. The host cell may be any prokaryotic or eukaryotic cell. Thus, a nucleotide sequence derived from the cloning of mammalian TRIO proteins, encoding all or a selected portion of the full-length protein, can be used to produce a recombinant form of a mammalian TRIO polypeptide in a cell.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The present invention further pertains to methods of producing the subject TRIO polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant TRIO polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant TRIO polypeptide is a fusion protein containing a domain which facilitates its purification, such as GST fusion protein or poly(His) fusion protein.

In other embodiments transgenic animals, described in more detail below can be used to produce recombinant proteins.

The present invention also provides for a recombinant transfection system, including a TRIO gene construct operatively linked to a transcriptional regulatory sequence and a gene delivery composition for delivering the gene construct to a cell so that the cell expresses the TRIO protein.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a mammalian TRIO polypeptide or, in the case of anti-sense expression from the transferred gene, the expression of a naturally-occurring form of the TRIO protein is disrupted.

A "delivery composition" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors).

II. Polypeptides

The present invention further pertains to isolated and/or recombinant forms of a TRIO polypeptide. The terms "protein", "polypeptide" and "peptide" are used interchangably herein.

The term "recombinant protein" refers to a polypeptide of the present invention which is produced by recombinant DNA techniques, wherein generally, DNA encoding a mammalian TRIO polypeptide is inserted into a suitable expression vector which is in turn used to transform a host cell to produce the heterologous protein, as described above. Moreover, the phrase "derived from", with respect to a recombinant TRIO gene, is meant to include within the meaning of "recombinant protein" those proteins having an amino acid sequence of a native TRIO protein, or a similar amino acid sequence which is generated by mutations including substitutions and deletions (including truncation) of a naturally occurring form of the protein.

The present invention also makes available isolated TRIO polypeptides which are isolated from, or otherwise substantially free from other cellular proteins, especially other factors which may normally be associated with the TRIO polypeptide. The term "substantially free of other cellular proteins" (also referred to herein as "contaminating proteins") or "substantially pure or purified preparations" are defined as encompassing preparations of TRIO polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least about 80% by dry weight, more preferably in the range of 95–99% by weight, and most preferably at least about 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" are not meant to encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified TRIO preparations will lack any contaminating proteins from the same animal from which TRIO is normally produced, as can be accomplished by recombinant expression of, for example, a human TRIO protein in a non-human cell.

In a particularly preferred embodiment a TRIO protein includes the amino acid sequence shown in SEQ ID No:2. In particularly preferred embodiments, a TRIO protein has a TRIO bioactivity.

The present invention also provides for TRIO proteins which have amino acid sequences evolutionarily related to the TRIO proteins represented in SEQ ID No: 2. In a preferred embodiment, a TRIO protein of the present invention is a mammalian TRIO protein. The term "evolutionarily related to", with respect to amino acid sequences of mammalian TRIO proteins, refers to both polypeptides having amino acid sequences which have arisen naturally, and also to mutational variants of mammalian TRIO polypeptides which are derived, for example, by combinatorial mutagenesis. Such evolutionarily derived TRIO polypeptides preferred by the present invention comprise an amino acid sequence at least about 60% homologous with the amino acid sequence shown in SEQ ID No: 2. In other embodiments, a TRIO polypeptide comprises an amino acid sequence at least about 70% homologous with the amino acid sequence shown in SEQ ID No: 2. In a preferred embodiment, a TRIO polypeptide comprises an amino acid sequence at least about 80% homologous with the amino acid sequence shown in SEQ ID No: 2. In another preferred embodiment, a TRIO polypeptide comprises an amino acid sequence at least about 90% homologous with the amino acid sequence shown in SEQ ID No: 2. In another preferred embodiment, a TRIO peptide comprises an amino acid sequence at least about 95–98% homologous with the amino acid sequence shown in SEQ ID NO: 2.

In certain embodiments, it will be advantageous to alter a TRIO polypeptide to provide homologs of one of the subject TRIO polypeptides which have only certain TRIO bioactivities. Such homologs would function in some capacity of either a TRIO agonist (mimetic) or a TRIO antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of TRIO proteins.

Homologs of each of the subject TRIO proteins can be generated by mutagenesis, such as by discrete point mutation(s), or by truncation. For instance, mutation can give rise to homologs which retain substantially the same, or merely a subset, of the biological activity of the TRIO polypeptide from which it was derived. Alternatively, antagonistic forms of the protein can be generated which are able to inhibit the function of the naturally occurring form of the protein, such as by competitively binding to a TRIO binding protein. In addition, agonistic forms of the protein may be generated which are constitutively active. Thus, the mammalian TRIO protein and homologs thereof provided by the subject invention may be either positive or negative regulators of apoptosis.

The recombinant TRIO polypeptides of the present invention also include homologs of the wild type TRIO proteins, such as versions of those protein which are resistant to proteolytic cleavage, as for example, due to mutations which alter ubiquitination or other enzymatic targeting associated with the protein. For example, the subject proteins can also be glycosylated. A "glycosylated" TRIO polypeptide is an TRIO polypeptide having a covalent linkage with a glycosyl group (e.g. a derivatized with a carbohydrate). An unglycosylated TRIO polypeptide can be generated by expression in a system which is defective for glycosylation, such as a bacterial cell. Alternatively, an existing glycosylation site can be mutated to preclude carbohydrate attachment. Likewise, new glycosylation sites, such as for N-linked or O-linked glycosylation, can be added by recombinant techniques.

TRIO polypeptides may also be chemically modified to create TRIO derivatives by forming covalent or aggregate conjugates with other chemical moieties, such as lipids, phosphate, acetyl groups and the like. Covalent derivatives of TRIO proteins can be prepared by linking the chemical moieties to functional groups on amino acid sidechains of the protein or at the N-terminus or at the C-terminus of the polypeptide.

Modification of the structure of the subject mammalian TRIO polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the TRIO polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, WH Freeman and Co.: 1981). Whether a change in the amino acid sequence of a peptide results in a functional TRIO homolog (e.g. functional in the sense that the resulting polypeptide mimics or antagonizes the wild-type form) can be readily determined by assessing the ability of the variant peptide to produce a response in cells in a fashion similar to the wild-type protein as discussed herein, or competitively inhibit such a response. Polypeptides in which more than one replacement has taken place can readily be tested in the same manner.

In another embodiment, a TRIO polypeptide is encoded by a TRIO nucleic acid as defined herein. In a preferred embodiment, a TRIO polypeptide has a TRIO bioactivity.

Full length proteins or fragments corresponding to one or more particular motifs and/or domains or to arbitrary sizes, for example, at least about 5, 10, 25, 50, 75, 100, 125, 150 amino acids in length are within the scope of the present invention. For example, isolated TRIO polypeptides can include all or a portion of an amino acid sequence corresponding to a TRIO polypeptide represented in or homologous to SEQ ID No:2. Isolated peptidyl portions of TRIO proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a TRIO polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") TRIO protein.

In preferred embodiments, a TRIO polypeptide comprises one or more TRIO domain.

In certain preferred embodiments, the invention features a purified or recombinant TRIO polypeptide having a molecular weight of approximately 330 kD. It will be understood that certain post-translational modifications can increase the apparent molecular weight of the TRIO protein relative to the unmodified polypeptide chain.

This invention further provides a method for generating sets of combinatorial mutants of the subject TRIO proteins as well as truncation mutants, and is especially useful for identifying potential variant sequences (e.g. homologs) that modulate a TRIO bioactivity. The purpose of screening such combinatorial libraries is to generate, for example, novel TRIO homologs which can act as either agonists or antagonist, or alternatively, possess novel activities all together. To illustrate, combinatorially-derived homologs can be generated to have an increased potency relative to a naturally occurring form of the protein.

Likewise, TRIO homologs can be generated by the present combinatorial approach to selectively inhibit (antagonize) an authentic TRIO. Moreover, manipulation of certain domains of TRIO by the present method can provide domains more suitable for use in fusion proteins.

In one embodiment, a library of TRIO variants is generated by combinatorial mutagenesis at the nucleic acid level, and is encoded by a variegated gene library. For instance, a mixture of synthetic oligonucleotides can be enzymatically ligated into gene sequences such that the degenerate set of potential TRIO sequences are expressible as individual polypeptides, or alternatively, as a set of larger fusion proteins (e.g. for phage display) containing the set of TRIO sequences.

There are many ways by which such libraries of potential TRIO homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential TRIO sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for a TRIO clone in order to generate a population of TRIO fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a TRIO coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of TRIO homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates isolation of the vector encoding the gene whose product was detected. Each of the illustrative assays described below are amenable to high through-put analysis as necessary to screen large numbers of degenerate TRIO sequences created by combinatorial mutagenesis techniques.

In one embodiment, cell based assays can be exploited to analyze the TRIO library. For instance, the library of expression vectors can be transfected into a cell line, preferably a cell line that does not normally express TRIO. The transfected cells are then monitored for changes in the organization of the actin cytoskeleton, eg. stress fiber formation or membrane ruffling. Alternatively, changes in cellular motility can be monitored.

Combinatorial mutagenesis has a potential to generate very large libraries of mutant proteins, e.g., in the order of $10^{26}$ molecules. Combinatorial libraries of this size can be screened using a variety of techniques, e.g., recrusive ensemble mutagenesis (REM) (Arkin and Yourvan, (1992), PNAS U.S.A. 89:7811–7815; Yourvan et al., (1992), Parallel Problem Solving from Nature, 2., In Maenner and Manderick, eds., Elsevir Publishing Co., Amsterdam, pp. 401–410; Delgrave et al., (1993), Protein Engineering 6(3):327–331).

The invention also provides for reduction of the mammalian TRIO proteins to generate mimetics, e.g. peptide or non-peptide agents, which are able to disrupt binding of a mammalian TRIO polypeptide of the present invention with binding proteins or interactors. Thus, such mutagenic techniques as described above are also useful to map the determinants of the TRIO proteins which participate in protein-protein interactions. Such interactions can be involved in, for example, binding of the subject mammalian TRIO polypeptide to proteins which may function upstream (including both activators and repressors of its activity) or downstream of the TRIO polypeptide, whether they are positively or negatively regulated by it. To illustrate, the critical residues of a subject TRIO polypeptide which are involved in molecular recognition of interactor proteins upstream or downstream of a TRIO (such as, for example LAR) can be determined and used to generate TRIO-derived peptidomimetics which competitively inhibit binding of the authentic TRIO protein to that moiety. By employing, for example, scanning mutagenesis to map the amino acid residues of each of the subject TRIO proteins which are involved in binding other extracellular proteins, peptidomimetic modulating agents can be generated which mimic those residues of the TRIO protein which facilitate the interaction. Such mimetics may then be used to interfere with the normal function of a TRIO protein. For example, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trns 1:1231), and β-aminoalcohols (Gordon et al. (1985) Biochem Biophys Res Commun 126:419; and Dann et al. (1986) Biochem Biophys Res Commun 134:71).

In another embodiment, the coding sequences for the polypeptide can be incorporated as a part of a fusion gene including a nucleotide sequence encoding a different polypeptide to generate a fusion protein or chimeric protein.

A "chimeric protein" or "fusion protein" is a fusion of a first amino acid sequence encoding one of the subject mammalian TRIO polypeptides with a second amino acid sequence defining a domain (e.g. polypeptide portion) foreign to and not substantially homologous with any domain of one of the mammalian TRIO proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-TRIO-Y, wherein TRIO represents a portion of the protein which is derived from one of the mammalian TRIO proteins, and X and Y are independently absent or represent amino acid sequences which are not related to one of the mammalian TRIO sequences in an organism, including naturally occurring mutants.

Fusion proteins can also facilitate the expression of proteins, and accordingly, can be used in the expression of the mammalian TRIO polypeptides of the present invention. For example, TRIO polypeptides can be generated as glutathione-S-transferase (GST-fusion) proteins. Such GST-fusion proteins can enable easy purification of the TRIO polypeptide, as for example by the use of glutathione-derivatized matrices (see, for example, Current Protocols in Molecular Biology, eds. Ausubel et al. (New York: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) J. Chromatography 411:177; and Janknecht et al. PNAS 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: (1992)).

In preferred embodiments, fusion proteins of the present invention contain a detectable label or a matrix binding domain.

The preparation of fusion proteins is often desirable when producing an immunogenic fragment of a TRIO protein. For example, the VP6 capsid protein of rotavirus can be used as an immunologic carrier protein for portions of the TRIO polypeptide, either in the monomeric form or in the form of a viral particle. The nucleic acid sequences corresponding to the portion of a subject TRIO protein to which antibodies are to be raised can be incorporated into a fusion gene construct which includes coding sequences for a late vaccinia virus structural protein to produce a set of recombinant viruses expressing fusion proteins comprising TRIO epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a TRIO protein and the poliovirus capsid protein can be created to enhance immunogenicity of the set of polypeptide antigens (see, for example, EP Publication No: 0259149; and Evans et al. (1989) Nature 339:385; Huang et al. (1988) J. Virol. 62:3855; and Schlienger et al. (1992) J. Virol. 66:2).

The Multiple Antigen Peptide system for peptide-based immunization can also be utilized to generate an immunogen, wherein a desired portion of a TRIO polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of TRIO proteins can also be expressed and presented by bacterial cells.

III. Antibodies

Another aspect of the invention pertains to an antibody specifically reactive with a mammalian TRIO protein. For example, by using immunogens derived from a TRIO protein, e.g. based on the cDNA sequences, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a mammalian TRIO polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a TRIO protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a TRIO protein of a mammal, e.g. antigenic determinants of a protein represented by SEQ ID No:2.

Following immunization of an animal with an antigenic preparation of a TRIO polypeptide, anti-TRIO antisera can be obtained and, if desired, polyclonal anti-TRIO antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a mammalian TRIO polypeptide of the present invention and monoclonal antibodies isolated from a culture comprising such hybridoma cells.

The term antibody as used herein is intended to include fragments thereof which are also specifically reactive with one of the subject mammalian TRIO polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a TRIO protein conferred by at least one CDR region of the antibody.

Antibodies which specifically bind TRIO epitopes can also be used in immunohistochemical staining of tissue samples in order to evaluate the abundance and pattern of expression of each of the subject TRIO polypeptides. Anti-TRIO antibodies can be used diagnostically in immuno-precipitation and immuno-blotting to detect and evaluate TRIO protein levels in tissue as part of a clinical testing procedure. Likewise, the ability to monitor TRIO protein levels in an individual can allow determination of the efficacy of a given treatment regimen for an individual afflicted with such a disorder. Diagnostic assays using anti-TRIO antibodies can include, for example, immunoassays designed to aid in early diagnosis of a degenerative disorder, particularly ones which are manifest at birth. Diagnostic assays using anti-TRIO polypeptide antibodies can also include immunoassays designed to aid in early diagnosis and phenotyping neoplastic or hyperplastic disorders.

Another application of anti-TRIO antibodies of the present invention is in the immunological screening of cDNA libraries constructed in expression vectors such as λ gt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a TRIO protein, e.g. other orthologs of a particular TRIO protein or other paralogs from the same species, can then be detected with antibodies, as, for example, reacting nitrocellulose filters lifted from infected plates with anti-TRIO antibodies. Positive phage detected by this assay can then be isolated from the infected plate. Thus, the presence of TRIO homologs can be detected and cloned from other animals, as can alternate isoforms (including splicing variants) from humans.

In certain embodiments, it will be desirable to attach a label group to the subject antibodies to facilitate detection. One means for labeling an anti- TRIO protein specific antibody is via linkage to an enzyme and use in an enzyme immunoassay (EIA) (Voller, "The Enzyme Linked Immunosorbent Assay (ELISA)", Diagnostic Horizons 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) Enzyme Immunoassay, CRC Press, Boca Raton, Fla., 1980; Ishikawa, et al., (eds.) Enzyme Immunoassay, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, TRIOse phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a $\gamma$ counter or a scintillation counter or by autoradiography.

It is also possible to label the antibody with a fluorescent compound. When the fluorescently labeled antibody is exposed to light of the proper wave length, its presence can then be detected. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

IV. Methods of Treating Disease

There are a wide variety of pathological conditions for which TRIO modulating agents of the present invention can be used in treatment. As used herein the term "modulating agent" refers to any of the subject polypeptides or nucleic acid molecules, such as gene therapy constructs, antisense molecules, peptidomimetics. In addition, a TRIO modulating agent can be a modulating agent identified in one of the drug assays provided herein. The term "modulation" encompases both increasing and decreasing TRIO activity. In certain embodiments it will be desirable to inhibit or reduce TRIO activity, such as with the subject antisense techniques. In other embodiments, it will be desirable to increase or augment TRIO activity in a cell, for example using the subject gene therepy techniques.

The subject TRIO modulating agents can be used, inter alia, to effect changes in the actin cytoskeleton. As such, the subject agents are useful in the modulation of wound healing morphogenic migrations, and/or tumor metastasis.

The subject TRIO therapeutics will be useful in regulating the activation of phagocytes, such as neutrophils and monocytes, and thus, in regulating the immune response to infectious agents. Moreover, it is expected that TRIO therapeutics will be useful in the treatment of diseases in which the immune response is impaired, such as chronic granulomatous disease.

Compounds of the present invention may influence cellular mitogenesis, DNA synthesis, cell division and differentiation. For example, as described herein, TRIO has been implicated in the activation of the JNK pathway. Certain cytokines and stresses to cells, such as DNA damage, appear to preferentially activate the JNK/SAPK pathway, leading to apoptosis. Therefore, regulators of the stress-activated JNK/p38 pathway, such as TRIO, are important in determining whether a cell survives or undergoes apoptosis. As used herein, apoptosis refers to the form of cell death that comprises: progressive contraction of cell volume with the preservation of the integrity of cytoplasmic organelles; condensation of chromatin, as viewed by light or electron microscopy; and DNA cleavage, as electrophoresis or labeling of DNA fragments using terminal deoxytransferase (TDT). Cell death occurs when the membrane integrity of the cell is lost and cell lysis occurs. Apoptosis differs from necrosis, in which cells swell and eventually rupture. With the identification of the nucleic acid encoding TRIO, the expression of TRIO can be regulated, thereby regulating the JNK pathway. In this manner, entry of cells into the apoptotic program can be regulated. Moreover, it has been reported that susceptibility to apoptosis can influence both net tumor growth (Arends and Harrison (1994) *Molecular Biology in Histopathology* (ed.) J. Crocker. Chapter 8 pp. 151–170. John Wiley & Sons Ltd.) and the response to anti-cancer therapies (Chu (1994) J. Biol. Chem. 269:787).

TRIO is also recognized as being involved in the activation of oncogenes, such as c-fos. In addition, as described in the appended examples, TRIO has been demonstrated to induce transformation of cells. In a preferred embodiment, the TRIO therapeutic of the present invention is used to treat a cancer cell, either in vitro or in vivo, in order to render reduce the tumorigenicity. Moreover, the importance of TRIO in controlling actin remodeling, indicates that TRIO therapeutics will be useful in the treatment of metastatic tumor cells in order to control their invasive capabilities.

In addition to proliferative disorders, TRIO therapeutics can be used for the treatment of differentiative disorders which result from, for example, de-differentiation of tissue which may (optionally) be accompanied by abortive reentry into mitosis, e.g. apoptosis. Such degenerative disorders include chronic neurodegenerative diseases of the nervous system, including Alzheimer's disease, Parkinson's disease, Huntington's chorea, amylotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

In such embodiments of the subject method, the cultured cells can be contacted with a TRIO therapeutic in order to induce differentiation (e.g. of a stem cell), or to maintain the integrity of a culture of terminally-differentiated cells by preventing loss of differentiation. Accordingly, the manipulating the activities of the JNKs, with the subject TRIO therapeutic may be useful in modulating the differentiation state of a cell, or at least to potentiate the activity of a maintenance factor such as CNTF, NGF or the like.

Cytoskeletal Changes

The changes in the organization of the actin cytoskeletal induced by TRIO-racGEF (e.g., enhanced membrane ruffling) or TRIO-rhoGEF (e.g., increased stress fiber formation and FA formation) in NIH 3T3 cells is consistent with the TRIO GEF-D1 domain having rac1-specific GEF activity and the TRIO GEF-D2 domain having rhoA activity. Previously it was demonstrated that injection of constitutively activated forms of rac1 into Swiss 3T3 cells induces membrane ruffling, whereas injection of rhoA induces stress fiber formation and FA formation (ref). In the stably expressing TRIO-racGEF and TRIO-rhoGEF deletion mutants the changes in the actin cytoskeleton are readily evident.

Since the subject TRIO modulating agents can either increase or decrease TRIO activity, the agents will be useful for both stimulating or suppressing responses.

V. Pharmaceutical Preparations

The subject modulating agents can be administered to a subject at therapeutically effective doses to treat or ameliorate a disorder benefiting from the modulation of TRIO. The data obtained from cell culture assays and animal studies can be used in formulating a range of dosage for use in humans. The dosage of such modulating agents lies preferably within a range of circulating or tissue concentrations that include the ED50 with little or no toxicity. The dosage may vary within this range depending upon the dosage form employed and the route of administration utilized. For any modulating agent used in the method of the invention, the therapeutically effective dose can be estimated initially from cell culture assays. A dose may be formulated in animal models to achieve a circulating plasma concentration range that includes the IC50 (i.e., the concentration of the test modulating agent which achieves a half-maximal inhibition of symptoms) as determined in cell culture. Such information can be used to more accurately determine useful doses in humans. Levels in plasma may be measured, for example, by high performance liquid chromatography.

In clinical settings, the gene delivery systems for the therapeutic TRIO gene can be introduced into a patient by any of a number of methods, each of which is familiar in the art. For example, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A mammalian TRIO gene, such as represented in SEQ ID NO:1, or a sequence homologous thereto can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g., retroviral vectors, the pharmaceutical preparation can comprise one or more cells which produce the gene delivery system.

Pharmaceutical preparations for use in accordance with the present invention may also be formulated in conventional manner using one or more physiologically acceptable carriers or excipients. Thus, the modulating agents and their physiologically acceptable salts and solvates may be formulated for administration by, for example, injection, inhalation or insufflation (either through the mouth or the nose) or oral, buccal, parenteral or rectal administration.

For such therapy, the modulating agents of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical preparations may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active modulating agent.

For administration by inhalation, the preparations for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the modulating agent and a suitable powder base such as lactose or starch.

The modulating agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The modulating agents may also be formulated in rectal compositions such as suppositories or retention enemas, e.g., containing conventional suppository bases such as cocoa butter or other glycerides.

In addition to the formulations described previously, the modulating agents may also be formulated as a depot preparation. Such long acting formulations may be administered by implantation (for example subcutaneously or intramuscularly) or by intramuscular injection. Thus, for example, the modulating agents may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

The compositions may, if desired, be presented in a pack or dispenser device, or as a kit with instructions. The composition may contain one or more unit dosage forms containing the active ingredient. The pack may for example comprise metal or plastic foil, such as a blister pack. The pack or dispenser device may be accompanied by instructions for administration.

VI. Diagnostic and Prognostic Assays

The present method provides a method for determining if a subject is at risk for a disorder characterized by aberrant cell proliferation or migration. In preferred embodiments, the methods can be characterized as comprising detecting, in a sample of cells from the subject, the presence or absence of a genetic lesion characterized by at least one of (i) an alteration affecting the integrity of a gene encoding a TRIO-protein, or (ii) the mis-expression of the TRIO gene. To illustrate, such genetic lesions can be detected by ascertaining the existence of at least one of (i) a deletion of one or more nucleotides from a TRIO gene, (ii) an addition of one or more nucleotides to a TRIO gene, (iii) a substitution of one or more nucleotides of a TRIO gene, (iv) a gross chromosomal rearrangement of a TRIO gene, (v) a gross alteration in the level of a messenger RNA transcript of a TRIO gene, (vii) aberrant modification of a TRIO gene, such as of the methylation pattern of the genomic DNA, (vii) the presence of a non-wild type splicing pattern of a messenger RNA transcript of a TRIO gene, (viii) a non-wild type level of a TRIO-protein, (ix) allelic loss of a TRIO gene, and (x) inappropriate post-translational modification of a TRIO-protein. As set out below, the present invention provides a large number of assay techniques for detecting lesions in a TRIO gene, and importantly, provides the ability to discern between different molecular causes underlying TRIO-dependent aberrant cell growth, proliferation, migration and/or differentiation.

In an exemplary embodiment, a nucleic acid composition is provided which contains an oligonucleotide probe previously described. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) PNAS 91:360–364), the latter of which can be particularly useful for detecting point mutations in the TRIO gene (see Abravaya et al. (1995) Nuc Acid Res 23:675–682). In an illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a TRIO gene under conditions such that hybridization and amplification of the TRIO-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. U.S.A. 87:1874–1878), transcriptional amplification system (Kwoh, D. Y. et al., 1989, Proc. Natl. Acad. Sci. U.S.A. 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In another embodiment of the subject assay, mutations in a TRIO gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the TRIO gene and detect mutations by comparing the sequence of the sample TRIO with the corresponding wild-type (control) sequence. Exemplary sequencing reactions include those based on techniques developed by Maxim and Gilbert (Proc. Natl Acad Sci U.S.A. (1977) 74:560) or Sanger (Sanger et al (1977) Proc. Nat. Acad. Sci 74:5463). Any of a variety of automated sequencing procedures may be utilized when performing the subject assays (Biotechniques (1995) 19:448), including by sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one skilled in the art that, for certain embodiments, the occurence of only one, two or three of the nucleic acid bases need be determined in the sequencing reaction. For instance, A-tract sequencing where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) Science 230:1242). In general, the art technique of "mismatch cleavage" starts by providing heteroduplexes formed by hybridizing (labelled) RNA or DNA containing the wild-type TRIO sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl Acad Sci USA 85:4397; Saleeba et al (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in TRIO cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a TRIO sequence, e.g., a wild-type TRIO sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in TRIO genes. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125–144; and Hayashi (1992) Genet Anal Tech Appl 9:73–79). Single-stranded DNA fragments of sample and control TRIO nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al (1989) Proc. Natl Acad. Sci U.S.A. 86:6230). Such allele specific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci U.S.A. 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a TRIO gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., (1992), PCR in situ hybridization: protocols and applications, Raven Press, New York).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant TRIO proteins, which are discussed, above, may also be used in disease diagnostics and prognostics. Such diagnostic methods, may be used to detect abnormalities in the level of TRIO protein expression, or abnormalities in the structure and/or tissue, cellular, or subcellular location of TRIO protein. Structural differences may include, for example, differences in the size, electronegativity, or antigenicity of the mutant TRIO protein relative to the normal TRIO protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of TRIO proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the TRIO protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

Moreover, any of the above methods for detecting alterations in a TRIO gene or gene product can be used to monitor the course of treatment or therapy.

VII. Drug Screening Assays

The present invention also provides for assays which can be used to screen for modulating agents, including TRIO homologs, which are either agonists or antagonists of the normal cellular function of the subject TRIO polypeptides, or of their role in the pathogenesis of cellular differentiation and/or proliferation and related disorders related. A variety of assay formats can be used for the subject assays.

In many drug screening programs which test libraries of modulating agents and natural extracts, high throughput assays are desirable in order to maximize the number of modulating agents surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test modulating agent. Moreover, the effects of cellular toxicity and/or bioavailability of the test modulating agent can be generally ignored in the in vitro system, the assay instead being focused primarily on the effect of the drug on the molecular target as may be manifest in an alteration of binding affinity with upstream or downstream elements.

In an exemplary screening assay of the present invention, the modulating agent of interest is contacted with proteins which may function upstream (including both activators and repressors of its activity) or to proteins or nucleic acids which may function downstream of the TRIO polypeptide, whether they are positively or negatively regulated by it. To the mixture of the modulating agent and the upstream or downstream element is then added a composition containing a TRIO polypeptide. Detection and quantification of the interaction of TRIO with it's upstream or downstream elements provide a means for determining a modulating agent's efficacy at inhibiting (or potentiating) complex formation between TRIO and the TRIO-binding elements. The term "interact" as used herein is meant to include detectable interactions between molecules, such as can be detected using, for example, a yeast two hybrid assay. The term interact is also meant to include "binding" interactions between molecules. Interactions may be protein-protein or protein-nucleic acid in nature.

The efficacy of the modulating agent can be assessed by generating dose response curves from data obtained using various concentrations of the test modulating agent. Moreover, a control assay can also be performed to provide a baseline for comparison. In the control assay, isolated and purified TRIO polypeptide is added to a composition containing the TRIO-binding element, and the formation of a complex is quantitated in the absence of the test modulating agent.

Complex formation between the TRIO polypeptide and a TRIO binding element may be detected by a variety of techniques. Modulation of the formation of complexes can be quantitated using, for example, detectably labeled proteins such as radiolabeled, fluorescently labeled, or enzymatically labeled TRIO polypeptides, by immunoassay, or by chromatographic detection.

Typically, it will be desirable to immobilize either TRIO or its binding protein to facilitate separation of complexes from uncomplexed forms of one or both of the proteins, as well as to accommodate automation of the assay. Binding of TRIO to an upstream or downstream element, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/TRIO (GST/TRIO) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test modulating agent, and the mixture incubated under conditions conducive to complex formation, e.g., at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of TRIO-binding protein found in the bead fraction quantitated from the gel using standard electrophoretic techniques such as described in the appended examples.

Other techniques for immobilizing proteins on matrices are also available for use in the subject assay. For instance, either TRIO or its cognate binding protein can be immobilized utilizing conjugation of biotin and streptavidin. For instance, biotinylated TRIO molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with TRIO but which do not interfere with binding of upstream or downstream elements can be derivatized to the wells of the plate, and TRIO trapped in the wells by antibody conjugation. As above, preparations of a TRIO-binding protein and a test modulating agent are incubated in the TRIO-presenting wells of the plate, and the amount of complex trapped in the well can be quantitated. Exemplary methods for detecting such complexes, in addition to those described above for the GST-immobilized complexes, include immunodetection of complexes using antibodies reactive with the TRIO binding element, or which are reactive with TRIO protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the TRIO-BP. To illustrate, the TRIO-BP can be chemically cross-linked or genetically fused with horseradish peroxidase, and the amount of polypeptide trapped in the complex can be assessed with a chromogenic substrate of the enzyme, e.g. 3,3'-diaminobenzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-TRIO antibodies, can be used. Alternatively, the protein to be detected in the complex can be "epitope tagged" in the form of a fusion protein which includes, in addition to the TRIO sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

In addition to cell-free assays, such as described above, the readily available source of mammalian TRIO proteins provided by the present invention also facilitates the generation of cell-based assays for identifying small molecule agonists/antagonists and the like. For example, cells can be caused to overexpress a recombinant TRIO protein in the presence and absence of a test modulating agent of interest, with the assay scoring for modulation in TRIO responses by the target cell mediated by the test agent. As with the cell-free assays, modulating agents which produce a statistically significant change in TRIO-dependent responses (either inhibition or potentiation) can be identified. In an illustrative embodiment, the expression or activity of a TRIO is modulated in cells and the effects of modulating agents of interest on the readout of interest (such as apoptosis) are measured. For example, the expression of genes which are up- or down-regulated in response to a T cell receptor-mediated signal cascade can be assayed. In preferred embodiments, the regulatory regions of such genes, e.g., the 5' flanking promoter and enhancer regions, are operatively linked to a marker (such as luciferase) which encodes a gene product that can be readily detected.

Monitoring the influence of modulating agents on cells may be applied not only in basic drug screening, but also in clinical trials. In such clinical trials, the expression of a panel of genes may be used as a "read out" of a particular drug's therapeutic effect.

In another aspect of the invention, the subject TRIO polypeptides can be used to generate a "two hybrid" assay (see, for example, U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind to or interact with TRIO ("TRIO-binding proteins" or "TRIO-bp"). Such TRIO-binding proteins would likely be regulators of TRIO bioactivity.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a TRIO polypeptide. The second hybrid protein encodes a transcriptional activation domain fused in frame to a sample gene from a cDNA library. If the bait and sample hybrid proteins are able to interact, e.g., form a TRIO-dependent complex, they bring into close proximity the DNA binding domain and the activation domain of the transcriptional activator. This proximity is sufficient to cause transcription of a reporter gene which is operatively linked to a transcriptional regulatory site responsive to the transcriptional activator, and expression of the reporter gene can be detected and used to score for the interaction of the TRIO and sample proteins.

VIII. Transgenic Animals

The present invention also provides for transgenic animals in which expression of a genomic sequence or cDNA encoding a finctional TRIO polypeptide is enhanced, induced, disrupted, prevented or suppressed. The transgenic animals produced in accordance with the present invention will include exogenous genetic material. As set out above, the exogenous genetic material will, in certain embodiments, be a DNA sequence which results in the production of a TRIO protein (either agonistic or antagonistic), an antisense transcript, or a TRIO mutant. Further, in such embodiments, the sequence will be attached to a transcriptional control element, e.g., a promoter, which preferably allows the expression of the transgene product in a specific type of cell.

As used herein, the term "transgene" means a nucleic acid sequence (whether encoding or antisense to one of the mammalian TRIO polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the mammalian TRIO proteins, e.g., either agonistic or antagonistic forms. However, transgenic animals in which the recombinant TRIO gene is silent are also provided for, as for example, the FLP or CRE recombinase dependent constructs described below. Moreover, "transgenic animal" also includes those recombinant animals in which gene disruption of one or more TRIO genes is caused by human intervention, including both recombination and antisense techniques.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that one of the recombinant mammalian TRIO genes is present and/or expressed or disrupted in some tissues but not others.

These systems may be used in a variety of applications. For example, the cell- and animal-based model systems may be used to further characterize TRIO genes and proteins. In addition, such assays may be utilized as part of screening strategies designed to identify modulating agents which are capable of ameliorating disease symptoms. Thus, the animal- and cell-based models may be used to identify drugs, pharmaceuticals, therapies and interventions which may be effective in treating disease.

One aspect of the present invention concerns transgenic animals which are comprised of cells (of that animal) which contain a transgene of the present invention and which preferably (though optionally) express an exogenous TRIO protein in one or more cells in the animal. A TRIO transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a TRIO protein can be essential for many forms of lineage analysis and can additionally provide a means to assess the effects of, for example, lack of TRIO expression which might grossly alter development in small patches of tissue within an otherwise normal embryo. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject TRIO proteins. For example, excision of a target sequence which interferes with the expression of a recombinant TRIO gene, such as one which encodes an antagonistic homolog or an antisense transcript, can be designed to activate expression of that gene. This interference with expression of the protein can result from a variety of mechanisms, such as spatial separation of the TRIO gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death, migration and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of *Saccharomyces cerevisiae* (O'Gorman et al. (1991) Science 251:1351–1355; PCT publication WO 92/15694) can be used to generate in vivo site-specific genetic recombination systems.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant TRIO protein can be regulated via control of recombinase expression.

Use of the cre/loxP recombinase system to regulate expression of a recombinant TRIO protein requires the construction of a transgenic animal containing transgenes encoding both the Cre recombinase and the subject protein. Animals containing both the Cre recombinase and a recombinant TRIO gene can be provided through the construction of "double" transgenic animals. A convenient method for providing such animals is to mate two transgenic animals each containing a transgene, e.g., a TRIO gene and recombinase gene.

One advantage derived from initially constructing transgenic animals containing a TRIO transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic TRIO transgene is silent will allow the study of progeny from that founder in which disruption of TRIO mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the TRIO transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a TRIO transgene could remain silent into adulthood until "turned on" by the introduction of the trans-activator.

In one embodiment, gene targeting, which is a method of using homologous recombination to modify an animal's genome, can be used to introduce changes into cultured embryonic stem cells. By targeting a TRIO gene of interest e.g., in embryonic stem (ES) cells, these changes can be introduced into the germlines of animals to generate chimeras. The gene targeting procedure is accomplished by introducing into tissue culture cells a DNA targeting construct that includes a segment homologous to a target TRIO locus, and which also includes an intended sequence modification to the TRIO genomic sequence (e.g., insertion, deletion, point mutation). The treated cells are then screened for accurate targeting to identify and isolate those which have been properly targeted.

Methods of culturing cells and preparation of knock out constructs for insertion are known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) Current Topics in Devel. Biol. 20:357–371); and by Hogan et al. (Manipulating the Mouse Embryo: A Laboratory Manual, Cold Spring Harbor Laboratory Press, Cold Spring Harbor, N.Y. [1986]).

Introduction of the transgenic constructs nucleotide sequence into the embryo may be accomplished by any means known in the art such as, for example, microinjection, electroporation, calcium phosphate, or lipofection. Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264).

Other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a TRIO-gene can be controlled by recombinase sequences.

Animals containing more than one knockout construct and/or more than one transgene expression construct are prepared in any of several ways. A preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

Exemplification

The present invention is further illustrated by the following examples which should not be construed as limiting in any way. The contents of all cited references, including literature references, issued patents, published patent applications as cited throughout this application are hereby expressly incorporated by reference. The contents of Provisional Application Serial No. 60/014,214 are specifically incorporated by this reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., New York); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

Example 1

The LAR-D2 PTPase Domain Binds a Broadly Expressed Phosphoserineprotein

Methods

Figure 1A:
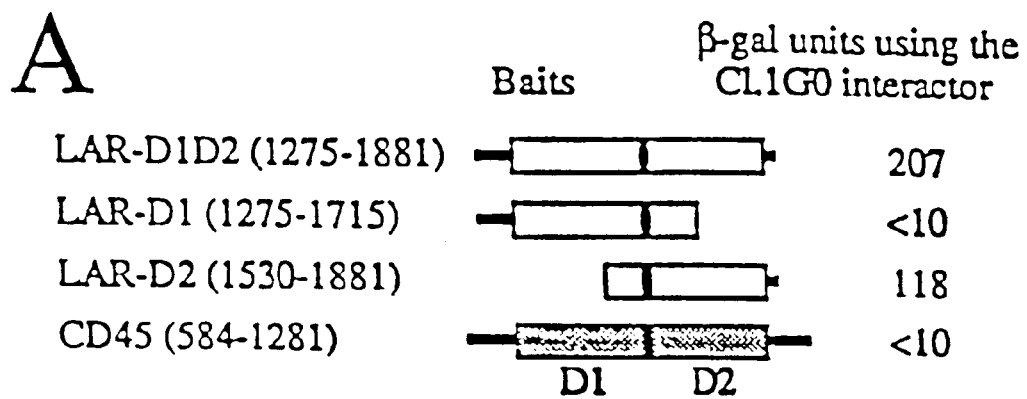
FIGS. 1A–1B show the identification of a LAR PTPase interacting protein, Cl.1G0. Panel A shows the mapping of sequences required for LAR and Cl.1G0 binding using the interaction-trap assay. Schematically shown are the regions of the LAR and CD45 cytoplasmic PTPase domains used as baits. Numbers in brackets indicate the amino acid residues included in the various fusion proteins. The D1 and D2 PTPase domains are indicated by open rectangles. Panel B shows that HA.Cl.1G0 and LAR coimmunoprecipitate. Molecular mass standards in kilodaltons (kDa) are shown at the left of the figure. At the right of the figure are indicated the positions of the cytoLAR and the HA.Cl.1G0 proteins.

Interaction-trap assay. Plasmid DNAs and yeast strains used for the interaction trap assay were provided by Dr. Roger Brent and colleagues (Massachusetts General Hospital, Boston, Mass.) and used essentially as described (Gyuris, J., et al. (1993) Cell 75, 791–803.). The human fibroblast cell WI-38 (ATCC CCL 75) cDNA library was used for the interaction-trap assay. The various LAR (Streuli, M., et al. (1988) J. Exp. Med. 168, 1523–1530.) and CD45 (Streuli, M., et al. (1987) J. Exp. Med. 166, 1548–1566.) regions fused to the LexA peptide are shown in FIG. 1A.

Northern blot analysis. Northern blot analysis was done using a human multiple tissue Northern blot (Clontech) which contains 2 μg of poly(A)+ selected RNA from different human tissues per lane, and was hybridized with a random primed [32P]-a-dCTP labeled TRIO cDNA probe (encoding aa 2249–2861 plus 140 bp of 3' non-translated sequence) according to the manufacturer's instructions.

Antibodies. To generate anti-TRIO mAbs, mice were immunized with E. coli-derived GST-TRIOD1 fusion protein. To this end, TRIO cDNA sequences encoding TRIO aa 2450–2861 were cloned into the pGEX.2T expression vector (Pharmacia); E. coli NM522 cells were transfected with the plasmid, and GST-TRIOD1 fusion protein was purified from bacterial lysates by Glutathione Sepharose 4B (Pharmacia) chromatography using standard methods, and then used as immunogen. HAT-resistant hybridomas derived from GST-TRIOD1 immunized mice were initially selected using ELISA, and then by immunoprecipitation studies. Anti-TRIO mAbs thus obtained were termed a-TRIO.56 (IgG1) and a-TRIO.68 (IgG1). The anti-hemagglutinin (HA) mAb 12CA5 was obtained from the Harvard University mAb Facility (Cambridge, Mass.), and anti-LAR sera was isolated from rabbits immunized with E. coli-derived, LAR intracellular region protein (aa 1275–1881).

Cells and Transfections. Simian COS-7 cells, human breast adenocarcinoma MCF7 and HeLa cells were cultured as described (Serra-Pagès, C., et al. (1995) EMBO J. 14, 2827–2838.). COS-7 cell transient transfections were done by the DEAE-dextran/DMSO method (Ausubel, F. M., et al. (1987–(1995)) Current Protocols in Molecular Biology, John Wiley & Sons, New York.).

Cell labeling and protein analysis. Cell proteins were metabolically labeled with [35S]methionine or [32P] orthophosphate as described (Serra-Pagès, C., et al.(1995) EMBO J. 14, 2827–2838.), except that for the [32P] orthophosphate labeling, cells were preincubated in media lacking FCS for 15 h prior to labeling. Preparation of cell extracts and immunoprecipitations were done as described (Serra-Pagès, C., et al. supra) using ~2 mg a-TRIO.56 or a-TRIO.68 mAb, 2 μg control isotype-matched mAb, or 1 ml anti-HA mAb 12CA5 ascites fluid. Immunoprecipitated proteins were analyzed using SDS-PAGE (6% gels) analysis with reducing conditions followed by autoradiography (18–72 h). The relative amounts of [32P]-labeled TRIO were determined by densitometric scanning of autoradiographs. Phosphoamino acid analysis was performed essentially as described (Boyle, W. J., et al. (1991) Methods Enzymol. 201, 110–149.).

Plasmid constructions and DNA sequencing. cDNA clones encoding TRIO were isolated from the human WI-38 cDNA library, as well as from fetal brain and heart cDNA libraries (Clontech Laboratories) using standard techniques, and sequenced using the dideoxy method of sequencing. The pMT.HA.Cl.1G0 (TRIO aa 2450–2861), pMT.HA.TRIOD2 (TRIO aa 1118–1919), and pMT.HA.TRIOD3 (TRIO aa 1849–2451) plasmids were constructed by inserting appropriate cDNA fragments into the pMT.HAtag expression vector (23). TRIOD.2 and TRIOD.3 contain 2 and 17 aa derived from vector sequences at their C-termini, respectively. pMT.cytoLAR encodes the LAR cytoplasmic region (aa 1275–1881) fused to the 30 N-terminal residues of DHFR encoded in the pMT.2 expression vector.

Exchange assays. The TRIOD2 and TRIOD3 proteins used for exchange assays were produced in COS-7 cells using pMT.HA.TRIOD2, and pMT.HA.TRIOD3 plasmid DNAs. As control, cells were transfected with a control pMT.HA plasmid. Following transfection, ~2×108 cells were resuspended in 2 ml of ice-cold suspension buffer (20 mM Tris-HCl (pH 8.0), 1 mM EDTA, 1 mM DTT, 0.5 mM PMSF, 10 mg/ml leupeptin, and 10 mg/ml aprotinin), and lysates were prepared using a Dounce homogenizer. Insoluble material was removed by centrifugation in a microfuge for 15 min at 4° C. Cdc42, rac, rho, and ras were purified from baculovirus infected cells as described (Malcom, K. C.,et al. (1994) J. Biol. Chem. 209, 25951–25954.), and kindly provided by Dr. Marc Symons (Onyx Pharmaceuticals, California). [3H]GDP loaded GTP binding proteins and exchange assays were performed essentially as described (Albright, C. F., et al. (1993) EMBO J. 12, 339–347.). Briefly, [3H]GDP loaded GTP binding proteins were prepared by incubating the purified proteins (0.5 mg) in 90 ml exchange buffer (50 mM Tris-HCl (pH 7.5), 50 mM NaCl, 5 mM EDTA, 1 mM DTT, and 1 mg/ml BSA) containing 7 mCi [3H]GDP (29.2 Ci/mmol; NEN/DuPont) for 20 min at 25° C. Following incubation, the reaction was quenched with 90 ml of stop exchange buffer (50 mM Tris-HCl (pH 7.5), 10 mM MgCl2, and 1 mM DTT), and then diluted with 1.5 ml of reaction stop buffer (50 mM Tris-HCl (pH 7.5), 1 mM GTP, and 2 mM MgCl2). 10 ml of COS cell lysate was added to 80 ml of [3H]GDP loaded GTP binding proteins and incubated at 25° C. for the indicated times. The reactions were quenched by adding 0.5 ml of stop buffer (50 mM Tris-HCl (pH 7.5) and 10 mM MgCl2) and immediately filtered through a nitrocellulose filter (BA85, 0.45 mm; Schleicher and Schuell); filters were then washed with stop buffer and the amount of radioactivity on the filters was determined.

Results

To isolate candidate proteins that interact with the LAR PTPase domains, a human WI-38 fibroblast (ATCC CCL75) cDNA library was screened using the interaction-trap assay and the cytoplasmic LAR-D1D2 bait (aa 1275–1881) as previously described (Serra-Pagès, C., et al. (1995) EMBO J. 14, 2827–2838; Gyuris, J., et al. (1993) Cell 75, 791–803.). Briefly, FIG. 1 shows the identification of a LAR PTPase interacting protein, Cl.1 G0. Panel A shows the mapping of sequences required for LAR and Cl.1G0 binding using the interaction-trap assay. Schematically shown are the regions of the LAR and CD45 cytoplasmic PTPase domains used as baits. Numbers in brackets indicate the amino acid residues included in the various fusion proteins. The D1 and D2 PTPase domains are indicated by open rectangles. Measurements of β-galactosidase (β-Gal) levels in liquid cultures were done in duplicate from two independent isolates, and the average values of β-gal units are shown. All of the fusion bait proteins, as well as the Cl.1G0 interactor protein were efficiently expressed in yeast as determined by immunoblotting experiments. HA.Cl.1G0 and LAR were found to coimmunoprecipitate. Shown in panel B is a SDS-PAGE analysis of proteins immunoprecipitated with a-HA mAb, 12CA5, or an a-LAR sera. COS-7 cells were transfected with the pMT.cytoLAR expression vector (lanes 1 and 4), pMT.HA.Cl.1G0 (lane 2), or with a mix of both the pMT.cytoLAR and pMT.HA.Cl.1G0 expression plasmids (lane 3). 18 h after transfection, cell proteins were metabolically labeled with [35S]methionine for 4 h. Following labeling, cell extracts were prepared and then immunoprecipitation analysis was performed using the anti-HA mAb (lanes 1–3) or anti-LAR sera (lane 4). Molecular mass standards in kilodaltons (kDa) are shown at the left of the figure. At the right of the figure are indicated the positions of the cytoLAR and the HA.Cl.1G0 proteins.

Two cDNA clones thus isolated, Cl.1G0 and Cl.2G0, were independent isolates derived from the same gene as determined by DNA sequence analysis. In addition to binding the LAR-D1D2 bait, the Cl.1G0 peptide also bound the LAR deletion bait, LAR-D2 (aa 1530–1881) which contains only the LAR-D2 PTPase domain, but did not bind the LAR deletion LAR-D1 bait (aa 1275–1715) or the CD45 bait (aa 584–1281) (FIG. 1A). Thus, the CL.1G0 fusion peptide specifically interacts with the LAR-D2 PTPase region.

Figure 1B:
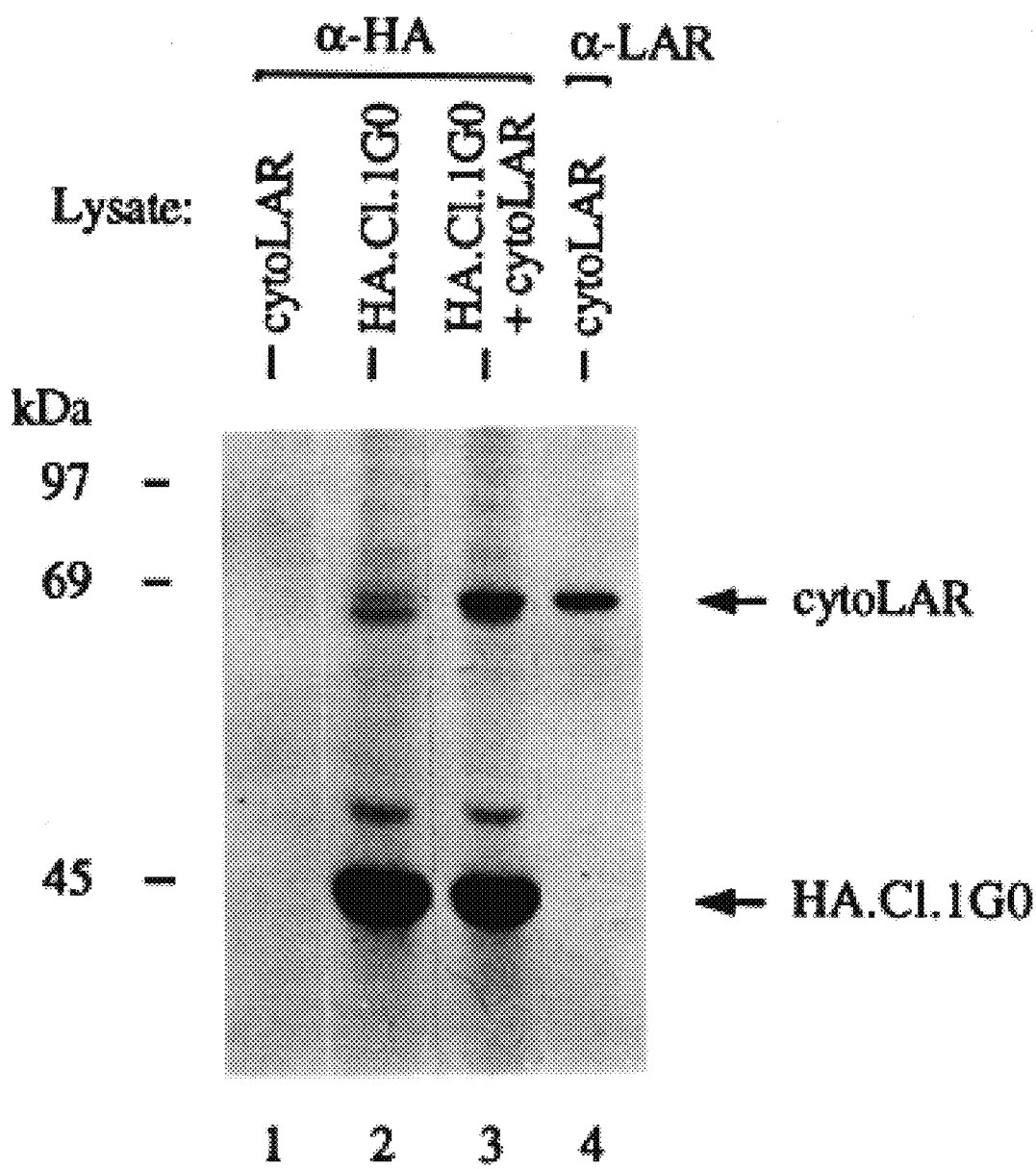

To determine if the Cl.1 G0 peptide also binds LAR in mammalian cells, a hemagglutinin (HA)-tagged Cl.1G0 peptide was transiently expressed in COS cells (HA-Cl.1 G0) together with the cytoplasmic region of LAR (cytoLAR; residues 1275–1881). In addition to immunoprecipitating the 44 kDa HA-Cl.1G0 peptide, the anti-HA mAb co-immunoprecipitated a 68 kDa protein that exactly co-migrated with cytoLAR immunoprecipitated using an anti-LAR sera (FIG. 1B). Furthermore, Western blot analysis using the anti-LAR sera confirmed that the 68 kDa protein present in the immunoprecipitates from the HA-Cl.1G0 plus cytoLAR co-tranfectants was cytoLAR (data not shown). Thus, the Cl.1G0 peptide binds cytoLAR in mammalian cells, as well as in the yeast interaction-trap assay.

Figure 2A:
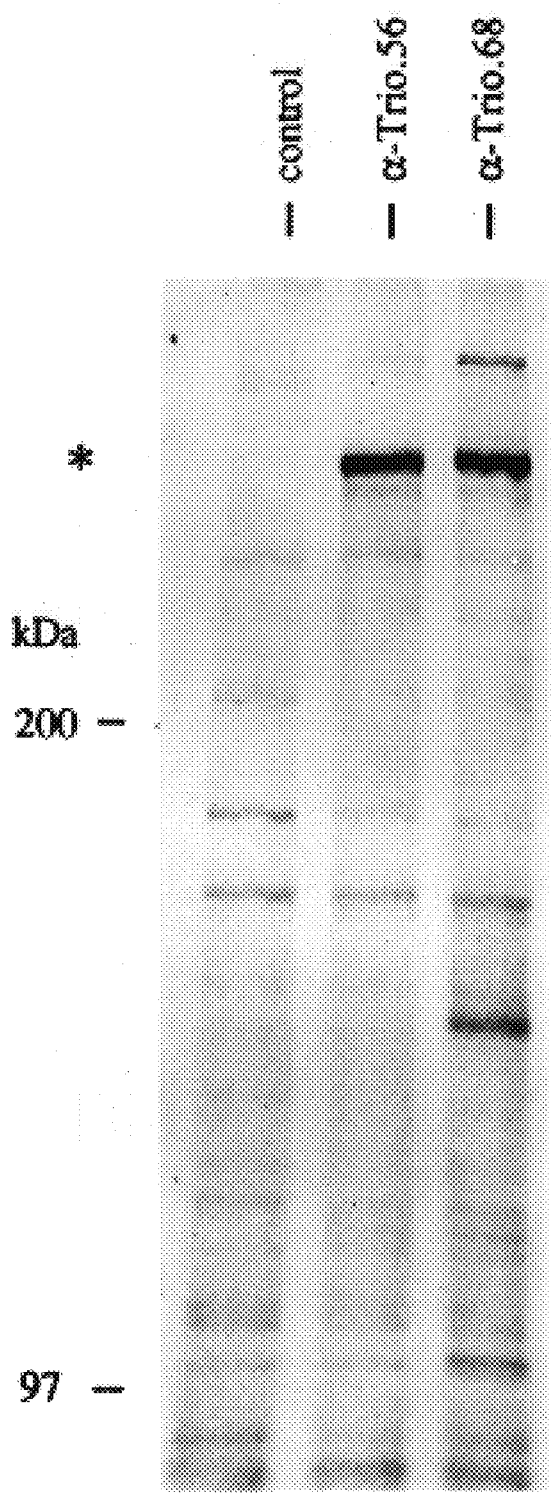

Two mAbs, termed anti-TRIO.56 and anti-TRIO.68, raised against a GST-Cl.1G0 fusion protein, both immunoprecipitated a large protein (>250 kDa) from [35S] methionine-labeled MCF7 cell lysates (FIG. 2A). This protein was termed TRIO (see below) and the Cl.1G0 peptide was redesignated TRIOD1. Coimmunoprecipitation studies of endogenous LAR and TRIO could not demonstrate an association of these proteins, and the anti-TRIO mAbs did not detect TRIO by immunofluorescence. Thus, the in vivo association between LAR and TRIO remains to be established.

A composit cDNA encoding a 2,861 amino acid protein, referred to herein as TRIO was isolated. The primary structure of TRIO was deduced by isolating and sequencing a series of overlapping TRIO cDNAs. The composite cDNA of 10.4 kb isolated contains an open reading frame encoding a protein of 2,861 aa with a calculated molecular mass of 323,897 (FIG. 4A), which is in agreement with the apparent size of the protein. SDS PAGE analysis yeilds an apparent molecular weight of >250 kD (see FIG. 2). Because the most N-terminal, in-frame methionine codon is not preceded by a termination codon, the numbering of the deduced TRIO amino acids may be modified. The protein sequence of TRIO is shown in SEQ ID No:2.

Example 2

Biochemical Characterization of TRIO

Immunoprecipitation analysis of TRIO from [32P] orthophosphate-labeled HeLa cell lysates demonstrated that TRIO is a phosphoprotein. Addition of the protein kinase C activator PMA, or the PTPase inhibitor pervanadate caused modest increases (3.3- and 2.8-fold, respectively) in the amount of 32P-labeled TRIO protein, as well as a slight decrease in the migration of TRIO isolated from the PMA-treated cells. FIG. 2 shows the biochemical characterization of TRIO. Panel A shows SDS-PAGE analysis of a-TRIO.56, a-TRIO.68 mAb, and isotype matched control mAb immunoprecipitated protein from [35S]methionine labeled human breast adenocarcinoma MCF7 cell lysates. Molecular mass standards in kilodaltons (kDa) are shown at the left of the figure. The position of the >250 kDa TRIO protein is indicated by an asterisk (*). Panel B shows SDS-PAGE analysis of a-TRIO.68 mAb and isotype-matched control mAb immunoprecipitated protein from [32P] orthophosphate-labeled HeLa cell lysates. Lysates were prepared from cells that were treated for 15 min with medium containing 10% FCS (media), 100 ng PMA/ml plus 10% FCS (+PMA), or 100 mM sodium pervanadate plus 10% FCS (+PV). On the bottom of the figure is shown the phosphoamino acid analysis of the 32P-labeled protein immunoprecipitated by the a-TRIO.68 mAb from medium-treated cells. The positions of the control, non-radiolabeled phosphorylated aa phosphoserine (P-Ser), phosphothreonine (P-Thr) and phosphotyrosine (P-Tyr) are indicated by ovals. The absence of tyrosine phosphorylation suggests that TRIO is not a substrate for the LAR PTPase. TRIO also did not significantly affect in vitro LAR PTPase activity (data not shown).

Example 3

Tissue Expression of TRIO

Northern blot analysis using a TRIO cDNA probe demonstrated that an ~10.5 kb TRIO mRNA was present in all eight human tissue samples tested (FIG. 3). Northern blot analysis of 2 mg of poly(A)+ RNA isolated from the human tissues indicated at the top of the figure using a radiolabeled TRIO cDNA probe. Size markers in kilobases (kb) are shown at the left of the figure. Audioradiography with an intensifying screen was for 2 days. Thus, TRIO appears to be a broadly expressed phosphoserine protein that binds the LAR-D2 PTPase domain.

Example 4

TRIO is a Multidomain Protein with Three Putative Enzymatic Functions

The primary structure of TRIO was deduced by isolating and sequencing a series of overlapping TRIO cDNAs. A composite cDNA of 10.4 kb thus isolated contains an open reading frame encoding a protein of 2,861 aa with a calculated molecular mass of 323,897 (FIG. 4A), which is in agreement with the apparent size of the protein (FIG. 2).

The multiple domains of TRIO are shown in FIG. 4. Panel A shows the TRIO 2,861 aa sequence deduced from cDNA cloning is shown using the standard one letter aa code. Numbers at the right indicate amino acid residues. Shown in panel B, the two TRIO GEF domains (TRIO GEF-D1 and -D2) are aligned with the dbl GEF and ost GEF domain sequences. Consensus invariant amino acids are in upper case and consensus amino acids present in dbl and ost and one of the two TRIO GEF sequences are in lower case. Numbers indicate amino acid residues used for the alignment. In panel C the TRIO PSK domain sequence is aligned with the kinase domains of DAP PSK and Dictyostelium MLCK. Consensus invariant amino acids are in upper case. Panel D shows the overall structure of TRIO is schematically shown with the relative length and positions of the four TRIO spectrin (SP)-like domains, two GEF domains, two pleckstrin homology (PH) domains, Ig-like domain, and the PSK domain. The horizontal line below the TRIO schematic indicates the relative length and position of the Cl.1G0 peptide.

The N-terminal region of TRIO is similar to the N-terminal regions of the dbs (Whitehead, I., et al. (1995) Oncogene 10, 713–721.), dbl (Ron, D., et al. (1988) EMBO J. 7, 2465–2473.), and ost (Horii, Y., et al. (1994) EMBO J. 13, 4776–4786.) GEFs. For example, the TRIO region spanning aa 3–208 of SEQ ID No:2 is approximately 31% identical to the dbs region spanning aa 69–281, and TRIO aa 126–208 of SEQ ID No: 2 are 36% identical to ost aa 10–93.

Following this N-terminal region of unknown function there are four domains (designated TRIO SP-D1 to -D4; aa 252–359, 479–585, 819–925, and 1050–1157, of SEQ ID Nos:16, 18, 20, and 22) that are 25–32% identical to the chicken a-spectrin 5 and 13 repeat sequences (Wasenius, V. et al. (1989) J. Cell Biol. 108, 79–93.). The sequences between these domains are weakly related to spectrin-repeats, suggesting that there might be 8 tandemly arranged spectrin-like repeats between residues 252 and 1157 of SEQ ID No:2. Spectrin repeats are approximately 106 aa long and found in a number of proteins, including the actin binding proteins spectrin, fodrin, a-actinin, and dystrophin (Dhermy, D. (1991) The spectrin super family. *Biol. Cell,* 71:249–254). These domains may play a role in connecting functional domains and/or mediate protein-protein interactions, and may direct the targeting of TRIO to the cytoskeleton and/or plasma membrane.

C-terminal to these repeats, there are two approximately 170 aa regions (aa 1237–1407 and 1914–2085 of SEQ ID No: 2) that are most similar to rho family GEF domains (Boguski, M. S. and McCormick, F. (1993) Nature 366, 643–654.). For instance, the TRIO GEF domain sequences (designated TRIO GEF-D1 shown in SEQ ID No:4 and TRIO GEF-D2 shown in SEQ ID No:6) are 44–49% identical with the dbl (Ron, D., et al. (1988) EMBO J. 7, 2465–2473) and ost GEF (Horii, Y., et al. (1994) EMBO J. 13, 4776–4786) domain sequences (FIG. 4B). Furthermore, TRIO GEF-D1 and -D2 contain essentially all of the conserved residues that define the three structurally conserved regions (SCR; FIG. 4B) in GEFs (Boguski, M. S. and McCormick, F. (1993) Nature 366, 643–654.).

C-terminal to each GEF domain there are regions with sequence similarity to pleckstrin homology (PH) domains, which are found in diverse signal transduction molecules (Musacchio, A., et al., (1993). The PH domain: a common piece in the structural patchwork of signalling proteins. TIBS, 18:343–348). The TRIO-PH1 (aa 1435–1534) and -PH2 (aa 2113–2214) domains are shown in SEQ ID No: 2. They are 25–37% identical to the PH domains found C-terminal to the dbl and ost GEF domains. PH domains are found adjacent to all functional rho/rac GEF domains, as well as in a number of other signal transduction proteins, and are expected to play a role in protein-protein interactions and/or membrane localization (Musacchio, A., et al. (1993) The PH domain: a common piece in the structural patchwork of signalling proteins. *TIBS,* 18:343–348, Pitcher, J. A., et al. (1995) Pleckstrin homology domain-mediated membrane association and activation of the b-adrenergic receptor kinase requires coordinate interaction with Gbg subunits and lipid. *J. Biol. Chem.,* 270:11707–11710).

At the TRIO C-terminal end (aa 2560–2816 of SEQ ID No: 2) there is a region that has all the sequence hallmarks of a PSK domain, suggesting that TRIO has kinase activity (Hanks, S. K. and Quinn, A. M. (1991) Meth. Enzymol. 200, 38–62). Of the 15 invariant or nearly invariant aa present in PSKs (Hanks and Quinn supra), all are conserved in TRIO (FIG. 4C). The TRIO PSK domain is 44% identical to the DAP kinase domain (Deiss, L. P., et al. (1995) Genes Devel. 9, 15–30) and 37% identical to *Dictyostelium myosin* light chain (MLC) PSK domain (Tan, J. L. and Spudich, J. A. (1991) J. Biol. Chem. 266, 16044–16049) (FIG. 4C). Thus, the PSK domain is most similar to calcium/calmodulin-dependent kinases, which similarly contain associated Ig-like domains, suggesting that calmodulin may play a role in the activation of TRIO.

Adjacent to the kinase domain there is an Ig-like domain (aa 2448–2541 of SEQ ID No: 2) that is 34% identical with an Ig-like domain present N-terminal of the chicken smooth muscle MLC kinase (MLCK) (Olson, N. J., et al. (1990) Proc. Natl. Acad. Sci. U.S.A. 87, 2284–2288.). The Ig-like domain may also play a role in protein-protein interactions. Other intracellular proteins, including smooth muscle MLCK (Olson, N. J., et al. (1990) Proc. Natl. Acad. Sci. U.S.A. 87, 2284–2288) and the *C. elegans* twitchin kinase (Benian, G. M., et al. (1989) Nature 342, 45–50), also contain Ig-like domains.

Example 5

The Two TRIO GEF Domains have Distinct Substrate Specificities for rac and rho

Figure 5A:
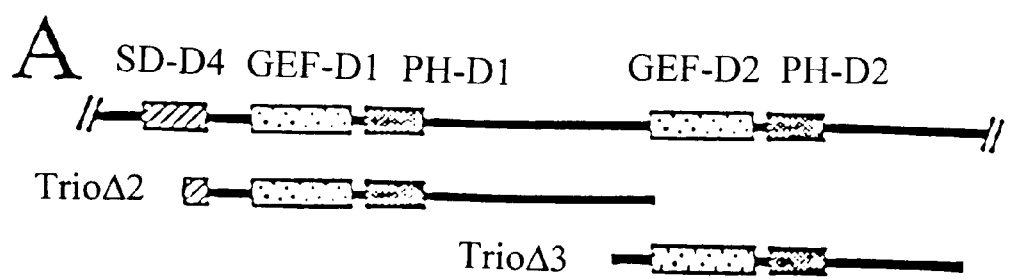
Figure 5B:
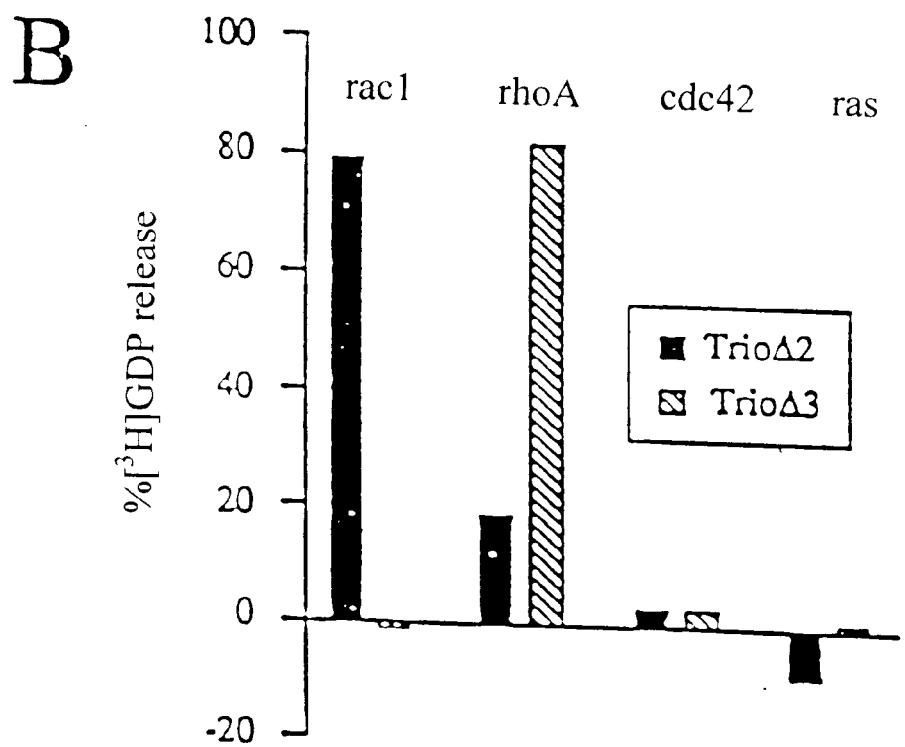
Figure 5C:
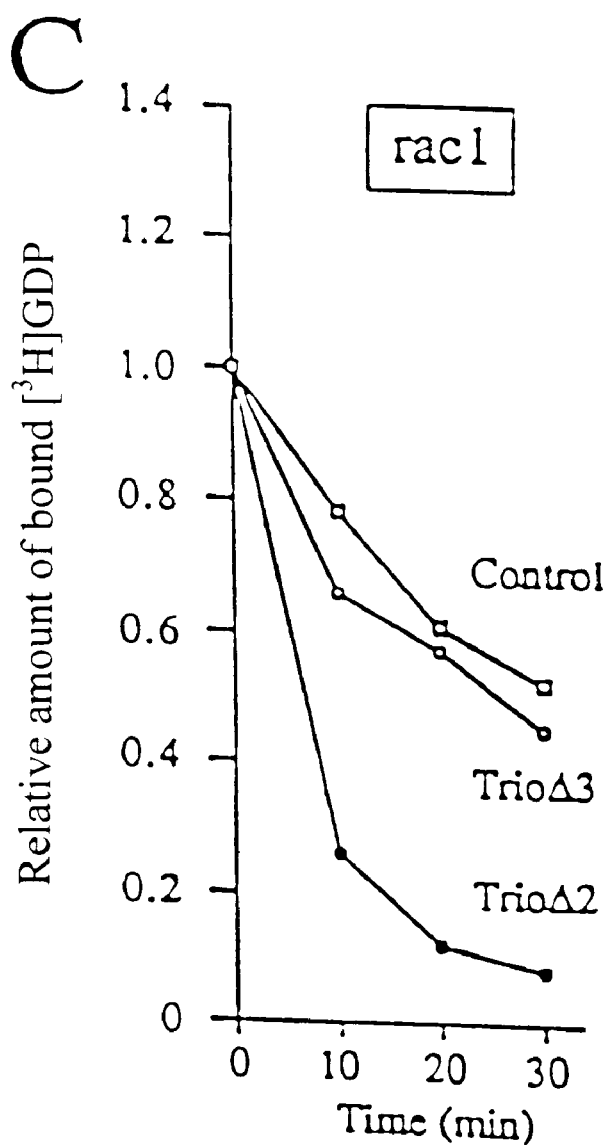
Figure 5D:
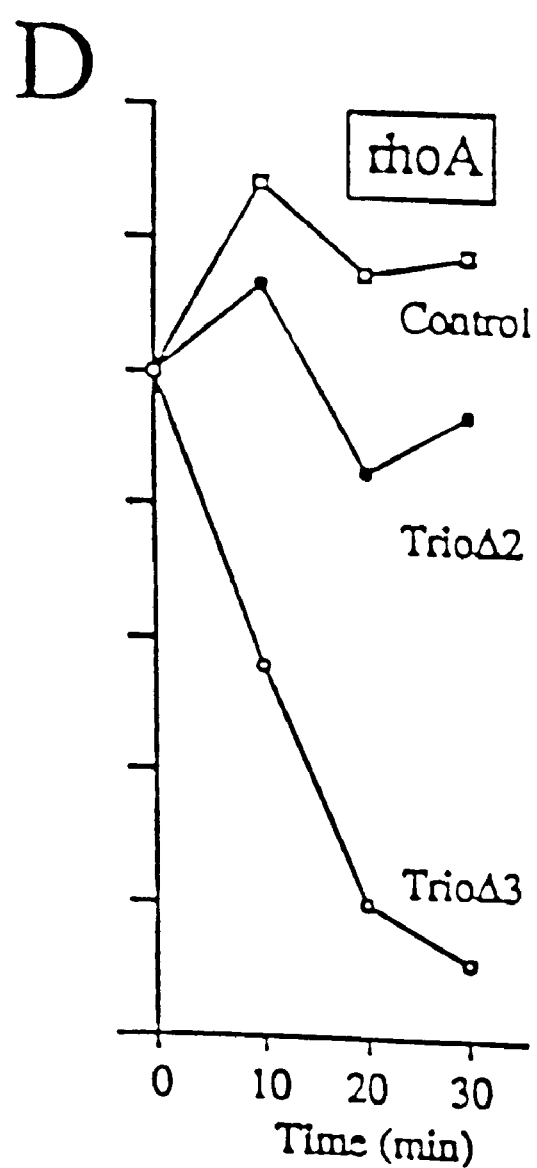

To determine whether the TRIO GEF-D1 and -D2 domains are functional GEFs, deletion mutants termed TRIOD2 (aa 1118–1919) and TRIOD3 (aa 1849–2451), were generated that encode either the TRIO GEF-D1 domain with the adjacent PH-D1 domain or the TRIO GEF-D2 domain with its adjacent PH-D2 domain (FIG. 5A). TRIOD2 and TRIOD3 were produced in COS cells as HA-fusion proteins. Lysates prepared from TRIOD2, TRIOD3, or control transfected cells were then incubated together with either [3H]GDP loaded rac1, rhoA, cdc42, or ras, and then the amount of [3H]GDP-bound protein remaining after 20 min was determined using a filter binding assay (Hart, M. J., et al (1991) Nature 354, 311–314; Albright, C. F., et al. (1993)EMBO J. 12, 339–347). TRIOD2 had significant GEF activity for rac1 (79% release compared to control), and limited or no activity (19% to –8%) with rhoA, cdc42 and ras (FIG. 5B). In contrast, TRIOD3 had significant activity with rhoA (82% release), and limited or no activity (3% to –1%) with rac1, cdc42, or ras (FIG. 5B). A time course analysis of [3H]GDP release using the TRIOD2 or TRIOD3 lysates with rac1 and rhoA substantiated the observation that TRIOD2 has rac-specific GEF activity, and TRIOD3 has rhoA-specific GEF activity (FIGS. 5C and D). These results demonstrate that the GEF-D1 and -D2 domains are functional GEF domains and that the GEF-D1 is a rac-specific GEF, and that GEF-D2 is a rho-specific GEF.

Example 6

TRIO is a Protooncogene

Expression of a TRIO deletion mutant (TRIOD2) which encodes the rac GEF activity causes cell transformation as assessed using the soft agar colony assay as described in the art.

Example 7

The Two TRIO GEF Domains Differently affect Cell Morphology

Methods

Preparation of TRIO Expressing Cell Lines

NIH 3T3 cells were grown in DMEM (Life Technologies) containing 10% FCS, 50 mg/ml gentamicin sulfate, and 2 mM L-glutamine. Cells were transfected by electroporation with linearized plasmid DNA using the Cell Porator Electroporation System (Life Technologies, Gaithersburg, Md.) essentially as described (Streuli et al., (1992). Expression of the receptor-linked protein tyrosine phosphatase LAR: proteolytic cleavage and shedding of the CAM-like extracellular region. *EMBO J.,* 11:897–907). NIH 3T3 cells were cotransfected with the pMT-2 based expression plasmids pMT.HA.TRIOD2, pMT.HA.TRIOD3 (the extent of the TRIO region encoded by these plasmids are schematically shown in FIG. 6; these TRIO deletion mutants contain a hemagglutinin (HA) tag sequence at their N-termini), or expression pMT.HA vector and pSP.SV.neo plasmid DNA which contains the neomycin resistance gene. Resulting clones were selected in medium supplemented with 0.5 mg/ml Geneticin (Life Technologies), and then maintained in medium supplemented with 0.25 mg/ml Geneticin. The resulting series of cell lines were designated NIH 3T3:TRIO-racGEF, NIH 3T3:TRIO-rhoGEF, and NIH 3T3:control. The expression levels of the TRIO deletion mutant proteins was determined by anti-HA-immunoprecipitation studies as previously described (Serra-Pages et al., (1995). *EMBO J.,* 14:2827–2838).

Transforming Activity of TRIO

The ability to grow in an anchorage-independent manner transformed phenotype of the stably transfected NIH 3T3 cells (NIH 3T3:TRIO-racGEF, NIH 3T3:TRIO-rhoGEF, and NIH 3T3:control) was assessed using the soft agar colony forming assay essentially as described in the art. Briefly, 1,000 cells were added to 1 ml DMEM media containing 20% v/v FCS and 0.33% (w/v) agar. After 18 d, the number of colonies $\geq 0.1$ mm in diameter were scored.

Cell Attachment/Spreading Assay

Cell attachment and spreading were assessed by phase contrast microscopy. NIH 3T3:TRIO-racGEF, NIH 3T3:TRIO-rhoGEF, and NIH 3T3:control cells were plated onto culture dishes ($10^6$ cells/cm$^2$), and allowed to attach. Both attached and unattached cells were quantified by washing the cells and counting the attached cells and the number of cells remaining in suspension. Representative fields of attached cells were documented by phase contrast photography. In addition to photographically documenting representative fields of attached cells, cell spreading was assessed by counting the number of attached spherical cells (i.e., cells attached but not spread) and the number of spreading/spread cells.

Immunofluorescence

Cells were stained for actin, tyrosine phosphorylated proteins (P-Try), or irrelevant antigen as previously described (Serra-Pages et al., (1995). *EMBO J.,* 14:2827–2838) using the anti-phosphotyrosine mAb 4G10 (Upstate Biotechnology), anti-actin mAb (Sigma), or isotype-matched control mAb. Cells were plated on glass coverslips and grown for several days prior to staining. For staining, cells were rinsed in PBS, fixed in 2% paraformaldehyde in PBS for 10 min, then permeabilized for 10 min in 0.5% Triton-X100 in PBS. Nonspecific antibody binding sites were blocked by a 30 min incubation in blocking buffer (2% normal goat serum in PBS). Cells were then incubated in blocking buffer supplemented with 0.1% sodium azide and 10 mg/ml each of the anti-actin and anti-P-Tyr mAbs, or the pair of isotype-matched control mAbs, for 30 min at room temperature. Following the incubation, the cells were washed with blocking buffer and then incubated in blocking buffer containing isotype-specific secondary antibody (goat anti-mouse IgG1-Texas Red and goat anti-mouse IgG2b-FITC (Southern Biotechnology Assoc., Birmingham, Ala.), as well as 0.5 mg/ml Hoechst dye #33258 (Sigma; to visualize DNA (blue)) for 30 min. at room temperature. Cells were washed with blocking buffer, and then slides were mounted in a polyvinyl alcohol medium and viewed on a Nikon FXA microscope equipped for epifluorescence. Photographs were taken on Fujichrome ASA 400 film.

Cell Motility Assay

Cell motility was assessed using a scratch-wound assay. Briefly, NIH 3T3:TRIO-racGEF, NIH 3T3:TRIO-rhoGEF, and NIH 3T3:control cells were plated onto culture dishes ($10^6$ cells/cm$^2$), allowed to attach and spread overnight, and then a region of the cell monolayer was removed by scratching using a rubber policeman. Following the scratching, the movement of cells into the wounded region was photographically recorded at various times indicated in FIG. 4 starting at the time of scratching (i.e., time 0). The plates were also marked in order to have a reference point for the phase contrast photography.

Results

Constitutively activated rac1 GTPase induces membrane ruffling and lamellipodia formation, whereas activated rhoA GTPase induces actin stress fiber formation and focal adhesion (FA) formation (Ridley and Hall, (1992). *Cell,* 70:389–399; Ridley et al., (1992). *Cell,* 70:401–410; Hotchin and Hall, (1995). *J. Cell Biol.,* 131:1857–1865; Kozma et al., (1995). *Mol. Cell. Biol.,* 15:1942–1952; Nobes and Hall, (1995). *Cell,* 81:53–62; Stowers et al., (1995). *Proc. Natl. Acad. Sci. USA,* 92:5027–5031; Chrzanowska-Wodnicka and Burridge, (1996). *J. Cell Biol.,* 133:1403–1415). To determine whether TRIO deletion mutants encoding the TRIO rac1-specific GEF or rhoA-specific GEF activities regulate cell morphology, stably transfected NIH 3T3 cell lines were established that express either the TRIO deletion mutant TRIO-racGEF, TRIO-rhoGEF, or vector-only control (the extent of the deletion mutations are schematically indicated in FIG. 6). In addition to the rac1GEF domain and rhoA GEF domain, the TRIO-racGEF and TRIO-rhoGEF deletion mutants also each encode a PH and a SH3 domain. The cell lines were designated NIH 3T3:TRIO-racGEF, NIH 3T3:TRIO-rhoGEF, and NIH 3T3:control.

Figures 7A, 7B, 7C, 7D:
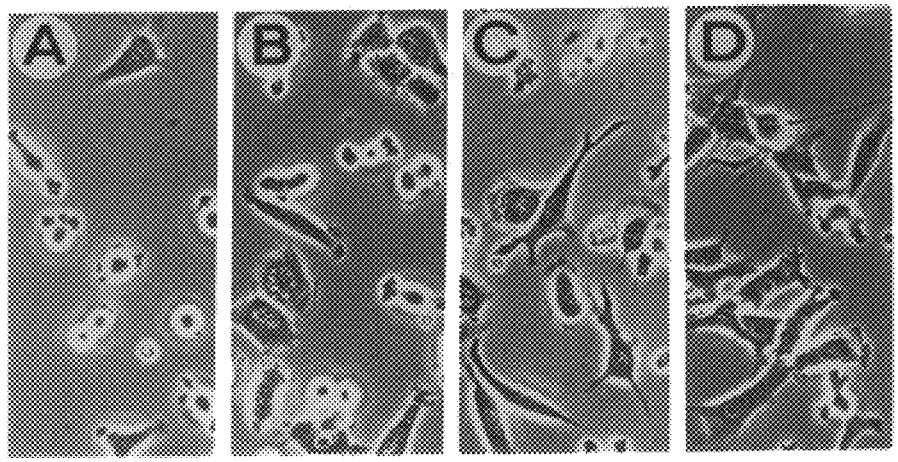
Figures 7I, 7J, 7K, 7L:
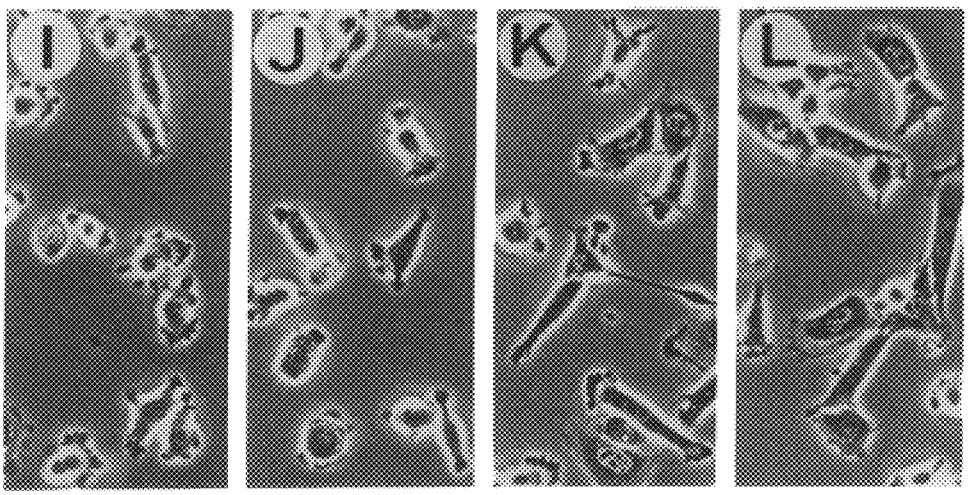

To ascertain whether expression of TRIO-racGEF or TRIO-rhoGEF affects cell attachment and/or spreading, the NIH 3T3:TRIO-racGEF, NIH 3T3:TRIO-rhoGEF, and NIH 3T3:control cells were plated onto culture dishes and there overall morphology was visualized by phase contrast microscopy at various time points following platting (FIG. 7). Seventy minutes after plating, the NIH 3T3:control (A), NIH 3T3:TRIO-racGEF (E), and NIH 3T3:TRIO-rhoGEF (I) cells all attached about equally well (>than 90% of the cells were attached to the dishes), suggesting that expression either TRIO-racGEF or TRIO-rhoGEF does not affect the ability of cells to attach. However, at 70 minutes virtually all of the NIH 3T3:TRIO-racGEF cells were spread out with extensive membrane ruffling (E), whereas only about half of the NIH 3T3:control cells were beginning to spread out (i.e., cells that are no longer spherical and become less refractive; FIG. 7A). The NIH 3T3:TRIO-rhoGEF cells also spread faster than the NIH 3T3:control cells (I), and contained extensive spike-like structures (I), which were not evident in the NIH 3T3 TRIO-racGEF or NIH 3T3 :control cells. At later time points (200 min and 270 min), the NIH 3T3:TRIO-rhoGEF cells (K and L) and NIH 3T3:control cells (C and D) became fully spread, whereas the NIH 3T3:TRIO-racGEF cells remained somewhat rounded, suggesting continued cell movement (G and H). Thus, TRIO-racGEF expression in NIH 3T3 cells causes enhanced efficiency of cell spreading and extensive membrane ruffling, whereas TRIO-rhoGEF expression increases the rate of cell spreading, and spreading is associated with spike-like protrusions. These observations demonstrate that the two TRIO GEF domains are both functional in vivo and that they differentially affect cell morphology.

To further characterize the cells expressing TRIO-racGEF or TRIO-rhoGEF, cells were stained for actin (green), phosphotyrosine (P-Tyr; red), and DNA (blue), and analyzed by fluorescence microscopy (FIG. 8). The NIH 3T3:TRIO-racGEF possess numerous membrane ruffles as revealed by anti-actin (green) staining and relatively few FAs as revealed by anti-P-Tyr staining (red) (FIG. 8B) compared to the NIH 3T3:control cells (FIG. 8A). In contrast, the NIH 3T3:rhoGEF cells contain significantly more actin stress fibers (green) and FAs (red and yellow: coincidence of green and red appears yellow; FIG. 8), and very few ruffles as compared to the control cells (FIG. 8A). Analysis with other FA markers such as vinculin confirmed the altered presence of FAs in the NIH 3T3-racGEF and NIH 3T3-rhoGEF cells compared to the NIH 3T3:control cells. The activities of TRIO-racGEF (i.e., rac1 activation) and TRIO-rhoGEF (i.e., rhoA activation) are consistent with previous results obtained by microinjecting constitutively active forms of rac1 and rhoA (Ridley and Hall, (1992). *Cell,* 70:389–399; Ridley et al., (1992). *Cell,* 70:401–410; Nobes and Hall, (1995). *Cell,* 81:53–62). Thus, it is possible that normally TRIO functions too regulate membrane ruffling, actin polymerization, and FA formation.

Example 8

TRIO-rhoGEF Expression Enhances Cell Locomotion

The locomotive motility of NIH 3T3 cell lines expressing TRIO-racGEF and TRIO-rhoGEF relative to control transfected NIH 3T3 cells was analyzed using a scratch-wound assay (FIG. 9). In this assay, cells were allowed to attach to tissue culture dishes for one day and then a region of the cell monolayer was removed. Following the scratching, the movement of the NIH 3T3:control (A–D), NIH 3T3:TRIO-racGEF (E–H), and NIH 3T3:TRIO-rhoGEF (I–L) cells into the wounded region of the monolayer was photographically recorded immediately following the scratching (A, E, and I), and at 6.5 h (B, F, and J), 12 h (C, G, and K) and 23 h (D, H, I) after the scratch/wounding (FIG. 9). While the NIH 3T3:TRIO-racGEF cells re-entered the wounded region at about the same rate as the NIH 3T3:control cells, the NIH 3T3:TRIO-rhoGEF cells re-entered the wounded region at least twice as fast as the NIH 3T3:control cells or NIH 3T3:TRIO-racGEF cells 23 h following the scratching (note the distance from the origin of the scratch (marked by arrows) of panel L compared to panels D and H). The increased locomotion of the NIH 3T3:TRIO-rhoGEF cells is already noticeable at 6.5 h post scratching (panel J), and clearly evident at 12 h (panel K). All three cell lines have similar proliferation rates so that the observed differences are not due to increased cell number of one relative to the others. Moreover, as the NIH 3T3:TRIO-rhoGEF cell front advances in a relatively uniform manner discernible already at 6.5 h following the scratching, we conclude that the observed difference between the various cell lines is due to enhanced cell locomotive motility of the NIH 3T3:TRIO-rhoGEF cells. These results indicate that increased levels of activated rhoA enhances NIH 3T3 cell locomotion.

Figure 9E:
Figure 9F:
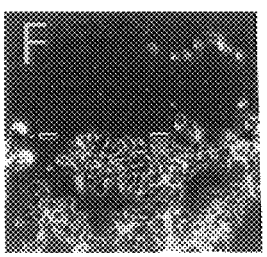
Figure 9G:
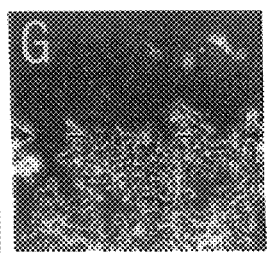
Figure 9H:
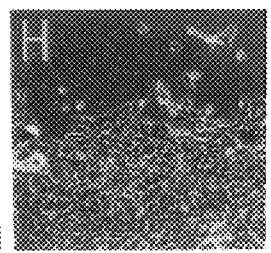
Figure 9I:
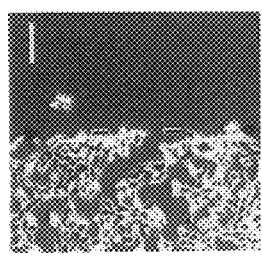
Figure 9J:
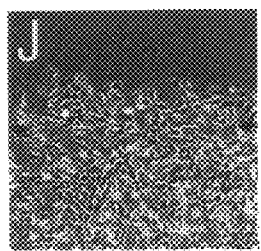
Figure 9K:
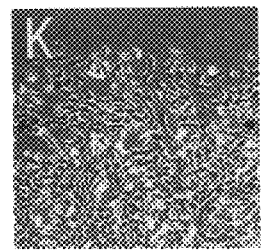
Figure 9L:
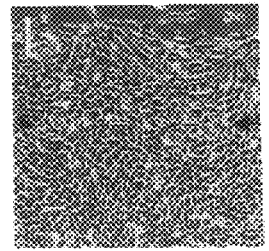
Figures 10A, 10B, 10C:
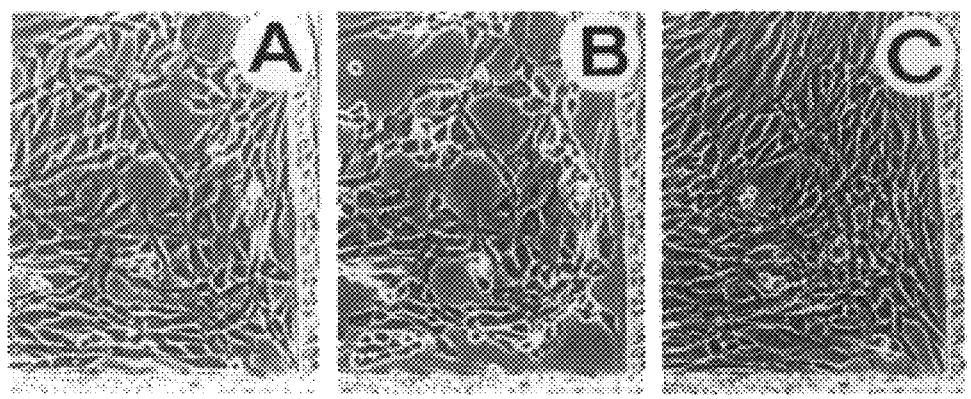
Figures 10D, 10E, 10F:
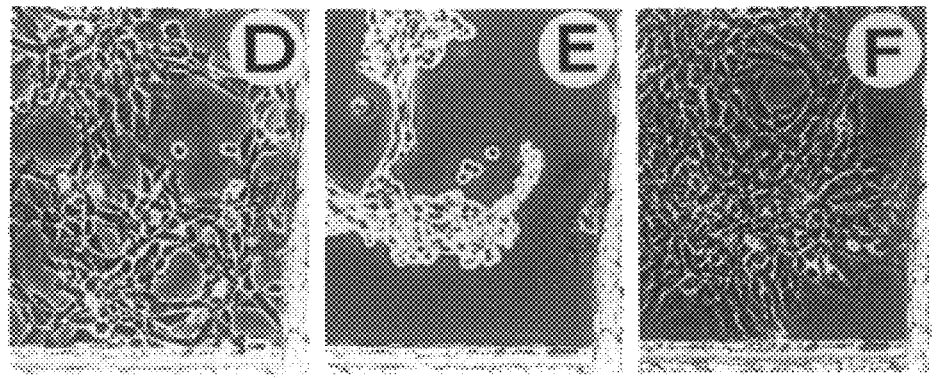
Figures 10G, 10H, 10I:
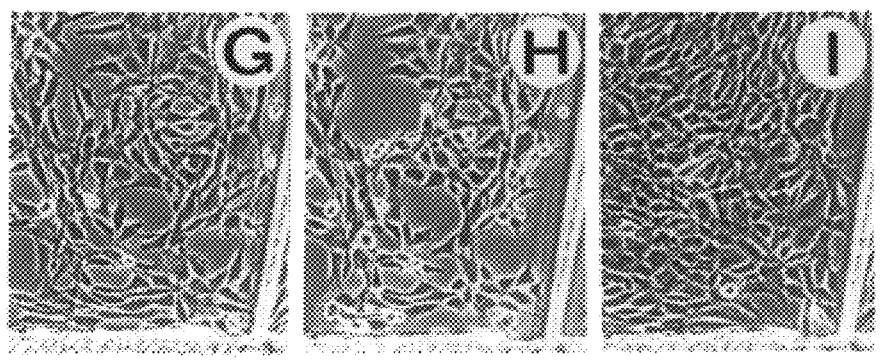

Although the NIH 3T3:TRIO-racGEF cells spread out very rapidly (see FIG. 7E), these cells were observed to aggregate following scratching of the monolayer in the scratch-wound assay (see FIG. 9E). All three cell lines, NIH 3T3:TRIO-racGEF, NIH 3T3:TRIO-rhoGEF, and NIH 3T3:control, form monolayers after 25.5 hours of incubation at 37° C. (FIGS. 10A, D, and G, respectively), but if the cells are cooled to ~21° C. (during photography), the NIH 3T3:TRIO-racGEF (E) cells, but not the NIH 3T3:control cells (B) or NIH 3T3:TRIO-rhoGEF (H) cells, rounded-up and formed cell aggregates. This change in NIH 3T3:TRIO-racGEF cell morphology was reversible, as these cells assumed a more spread-out morphology upon subsequent incubation at 37° C. (F). These results suggest that TRIO-racGEF expression confers temperature sensitivity to cell-matrix and/or cell-cell contacts.

Example 9

TRIO-racGEF Expression causes Anchorage-Independent Cell Growth

Rac and rho activities are essential for cell transformation by the ras oncogene (Khosravi-Far et al., (1995). *Mol. Cell. Biol.,* 15:6443–6453; Qiu et al., (1995). *Proc. Natl. Acad. Sci. USA,* 92:11781–11785), and many of the DH GEF family members were originally identified as oncogenes (Hart et al., 1991. *Nature,* 354:311–314; Hart et al., (1994). *J. Biol. Chem.,* 269:62–65; Horii et al., (1994). *EMBO J.,* 13:4776–4786; Michiels et al., (1995). *Nature,* 375:338–340; Zheng et al., (1995). *J. Biol. Chem.,* 270:9031–9034). To determine whether TRIO-racGEF or TRIO-rhoGEF expression causes anchorage-independent cell growth, the ability of the NIH 3T3:TRIO-racGEF, NIH 3T3:TRIO-rhoGEF, and NIH 3T3:control cells to form colonies in soft agar was assessed (Sawyers et al., (1992). *Cell,* 70:901–910; Qiu et al., (1995). *Proc. Natl. Acad. Sci. USA,* 92:11781–11785). Whereas the NIH 3T3:rhoGEF cells and NIH 3T3:control cells formed essentially no colonies in soft agar, the NIH 3T3:TRIO-racGEF cells formed numerous colonies in soft agar (Table 1). Thus, TRIO-racGEF expression enables cells to grow in an anchorage independent manner indicating that TRIO is a potential protooncogene.

TABLE 1

| Cell lines | Relative TRIO Expression level | Av. No. colonies (>0.1 mm diam.) | Clonability (# col./# input cells) |
|---|---|---|---|
| NIH 3T3:TRIO-racGEF (clone #1) | ++ | 42 | 4.2% |
| NIH 3T3:TRIO-racGEF (clone #2) | + | 60 | 6.0% |
| NIH 3T3:TRIO-rhoGEF (clone #1) | +++ | 1 | 0.1% |
| NIH 3T3:TRIO-rhoGEF (clone #2) | ++ | 0 | 0.0% |
| NIH 3T3:control (clone #1) | — | 1 | 0.1% |
| NIH 3T3:control (clone #2) | — | 0 | 0.0% |

Soft agar colony formation assay using NIH 3T3 cell lines expressing TRIO-racGEF, TRIO-rhoGEFTRIO, or vector only. Assays were done as essentially as described (Qiu et al., (1995). A role for Rho in Ras transformation. Proc. Natl. Acad. Sci. USA, 92: 11781–11785 and An essential role for rac in ras transformation. Nature, 374: 457–459), using 1,000 input cells; colonies > 0.1 mm in diameter were scored 18 days after plating. Relative TRIO expression levels were determined by immunoprecipitation analysis. Values represent the average of two independent experiments.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

What is claimed is:

1. An isolated nucleic acid molecule comprising a nucleotide sequence encoding TRIO.

2. An isolated nucleic acid molecule comprising a nucleotide sequence encoding a domain of a TRIO protein, wherein the domain: (i) comprises an amino acid sequence selected from the group consisting of: amino acids 1237–1407 of SEQ ID NO: 2, amino acids 1435–1534 of SEQ ID NO:2, amino acids 1914–2085 of SEQ ID NO:2, amino acids 2448–2541 of SEQ ID NO:2, amino acids 2560–2816 of SEQ ID NO:2, and (ii) has a TRIO bioactivity.

3. The isolated nucleic acid molecule of claim 1, wherein the nucleic acid molecule encodes a TRIO protein comprising a rac1 guanine nucleotide exchange factor (GEF) domain, a rhoA GEF domain, and a serine/threonine kinase domain.

4. The isolated nucleic acid molecule of claim 1, wherein the nucleic acid molecule encodes a TRIO protein that activates one or more of a rac GTPase and a rho GTPase.

5. The isolated nucleic acid molecule of claim 1, wherein the nucleic acid molecule encodes a TRIO protein that mediates actin remodeling in a cell.

6. A nucleic acid molecule which encodes a polypeptide with a TRIO bioactivity, wherein said nucleic acid encodes a polypeptide comprising a TRIO domain.

7. The isolated nucleic acid molecule of claim 1 which comprises a naturally-occurring nucleotide sequence.

8. The nucleic acid molecule of claim 1, wherein said nucleic acid molecule hybridizes to the nucleic acid sequence shown in SEQ ID NO:1 or a complement thereof under conditions of about 50% formamide in 6.0x sodium chloride/sodium citrate (SSC) at about 42° C. followed by a wash of 1% SDS in 2.0x SSC at 50° C. and a wash of 1% SDS in 2.0x SSC at 65° C.

9. An isolated nucleic acid molecule which specifically detects a TRIO nucleic acid molecule which encodes at least a portion of a TRIO protein domain under conditions of about 50% formamide in 6.0x sodium chloride/sodium citrate (SSC) at about 42° C. followed by a wash of 1% SDS in 2.0x SSC at 50° C. and a wash of 1% SDS in 2.0x SSC at 65° C., wherein said nucleic acid molecule hybridizes to a nucleotide sequence selected from the group consisting of: nucleotides 3775–3954 of the nucleotide sequence shown in SEQ ID NO:1 or a complement thereof, nucleotides 4284–4287 of the nucleotide sequence shown in SEQ ID NO:1 or a complement thereof, nucleotides 4372–4549 of the nucleotide sequence shown in SEQ ID NO:1 or a complement thereof, nucleotides 6403–6708 of the nucleotide sequence shown in SEQ ID NO:1 or a complement thereof, nucleotides 7990–8514 of the nucleotide sequence shown in SEQ ID NO:1 or a complement thereof.

10. The nucleic acid molecule of claim 9, wherein said nucleic acid molecule is at least about 100 nucleotides in length.

11. The nucleic acid molecule of claim 9, wherein said nucleic acid molecule hybridizes to nucleotides 6403–6708 of the nucleic acid sequence shown in SEQ ID NO:1 or a complement thereof.

12. The nucleic acid molecule of claim 1, wherein said nucleic acid molecule comprises the nucleotide sequence shown in SEQ ID NO:1 or a complement thereof.

13. The isolated nucleic acid molecule of claim 6 which encodes human TRIO.

14. The isolated nucleic acid molecule of claim 9, which is at least about 300 nucleotides in length.

15. An isolated nucleic acid molecule comprising the coding region of SEQ ID NO: 1 or a complement thereof.

16. An isolated nucleic acid molecule encoding the amino acid sequence of SEQ ID NO: 2.

17. An isolated nucleic acid molecule encoding a TRIO fusion protein.

18. A vector comprising the nucleic acid molecule of claim 1.

19. The vector of claim 18, which is a recombinant expression vector.

20. A host cell containing the vector of claim 19.

21. A method for producing TRIO protein comprising culturing the host cell of claim 20 in a suitable medium until TRIO protein is produced.

22. The method of claim 21, further comprising isolating TRIO protein from the host cell or the medium.

23. A method for detecting the presence of TRIO mRNA in a biological sample comprising contacting the biological sample with the nucleic acid molecule of claim 9 such that the presence of TRIO mRNA is detected in the biological sample.

24. The method of claim 23, wherein the agent detects TRIO mRNA.

25. The method of claim 23, wherein the nucleic acid molecule is labeled for detection.

* * * * *

UNITED STATES PATENT AND TRADEMARK OFFICE
CERTIFICATE OF CORRECTION

PATENT NO. : 5,994,070
DATED : November 30, 1999
INVENTOR(S) : Michel Streuli et al.

It is certified that error appears in the above-indentified patent and that said Letters Patent is hereby corrected as shown below: On the title page: Item [75]

Anne Debant the city "Padres le Lez" is spelled incorrectly. It should read "Prades le Lez".

Signed and Sealed this

Seventeenth Day of October, 2000

Attest:

Q. TODD DICKINSON

*Attesting Officer*     *Director of Patents and Trademarks*